United States Patent
Levitt et al.

(10) Patent No.: US 6,261,559 B1
(45) Date of Patent: Jul. 17, 2001

(54) METHODS OF TREATING ASTHMA WITH INTERLEUKIN-9 ANTIBODIES

(75) Inventors: Roy Clifford Levitt, Ambler; W. Lee Maloy, Landsdale; U. Prasad Kari, Hatfield; Nicholas C. Nicolaides, Media, all of PA (US)

(73) Assignee: Genaera Corporation, Plymouth Meeting, PA (US)

( * ) Notice: Subject to any disclaimer, the term of this patent is extended or adjusted under 35 U.S.C. 154(b) by 0 days.

(21) Appl. No.: 09/325,571

(22) Filed: Jun. 4, 1999

Related U.S. Application Data

(60) Continuation of application No. 08/874,503, filed on Jun. 13, 1997, now abandoned, which is a division of application No. 08/697,472, filed on Aug. 23, 1996, now abandoned.
(60) Provisional application No. 60/002,765, filed on Aug. 24, 1995.

(51) Int. Cl.[7] .................................................. C07K 16/24
(52) U.S. Cl. ..................................... 424/139.1; 424/141.1; 424/145.1; D24/110
(58) Field of Search ........................... 514/2, 8, 12, 885, 514/826; 424/85.1, 85.2, 130.1, 139.1, 145.1, 158.1, 141.1; D24/110

(56) References Cited

U.S. PATENT DOCUMENTS

| | | | |
|---|---|---|---|
| 4,427,660 | 1/1984 | Schiffman et al. | 424/177 |
| 4,703,004 | 10/1987 | Hopp et al. | 435/68 |
| 4,761,375 | 8/1988 | Clark | 388/806 |
| 5,116,951 | 5/1992 | Druez et al. | 530/395 |
| 5,132,109 | 7/1992 | Dugas et al. | 424/85.2 |
| 5,157,112 | 10/1992 | Van Snick et al. | 530/387.9 |
| 5,164,317 | 11/1992 | Hültner et al. | 435/240.2 |
| 5,180,678 | 1/1993 | Druez et al. | 436/501 |
| 5,208,218 | 5/1993 | Van Snick et al. | 514/8 |
| 5,246,701 * | 9/1993 | Dugas et al. | 424/85.8 |
| 5,414,071 | 5/1995 | Yang et al. | 530/351 |

FOREIGN PATENT DOCUMENTS

| | | |
|---|---|---|
| A2 0361284 | 4/1990 | (EP) . |
| WO90/14432 | 11/1990 | (WO) . |
| WO91/10738 | 7/1991 | (WO) . |
| WO91/14767 | 10/1991 | (WO) . |
| WO 92/05698 | 4/1992 | (WO) . |

OTHER PUBLICATIONS

Sevier et al. Clin Chem. vol. 27. No. 11, pp. 1797–1806, 1981.*

James R. Baker, Jr. and James L. Baldwin,"Allergy and Immunology," *J. of the American Medical Association*, vol. 275, No. 23, Jun. 19, 1996, pp. 1794–1795.

Larry Borish and Lanny J. Rosenwasser, "Continuing Medical Education: Update on cytokines," *J. of Allergy and Clinical Immunology*, vol. 97, No. 3, Mar. 1996, pp. 719–734.

Yves Collette, Hsun–Lang Chang, Chantal Cerdan, Herve Chambost, Michele Algarte, Claude Mawas, Jean Imbert, Arsene Burny and Daniel Olive, "Specific Th1 Cytokine Down–Regulation Associated with Primary Clinically Derived Human Immunodeficiency Virus Type 1 Nef Gene–Induced Expression," *J. of Immunology*, vol. 156, No. 1, Jan. 1, 1996, pp. 360–370.

Salvatore De Vita, Riccardo Dolcetti, Gianfranco Ferraccioli, Barbara Pivetta, Valli De Re, Annunziata Gloghini, Anna D'Agosto, Ettore Bartoli, Antonino Carbone, and Mauro Boiocchi, "Local Cytokine Expression in the Progression Toward B Cell Malignancy in Sjögren's Syndrome," *J. of Rheumatology*, vol. 22, No. 9, Sep. 1995, pp. 1674–1680.

James P. Di Santo, Ralf Kühn and Werner Müller, "Common Cytokine Receptor γ chain (γc)–Dependent Cytokines: Understanding in vivo Functions by Gene Targeting," *Immunological Reviews*, No. 148, Dec. 1995, pp. 19–34.

Iolo J. M. Doull, Sharon Lawrence, Mark Watson, Toresh Begishvili, Richard W. Beasley, Fiona Lampe, Stephen T. Holgate and Newton E. Morton, "Allelic Association of Gene Markers on Chromosomes 5q and 11q with Atopy and Bronchial Hyperresponsiveness," *American J. of Respiratory and Critical Care Medicine*, vol. 153, No. 4, Apr. 1996, pp. 1280–1284.

Jeffrey Fairman, Ilya Chumakov, A. Craig Chinault, Peter C. Nowell, and Lalitha Nagarajan, "Physical mapping of the minimal region of loss in 5q– chromosome," *Proc. Natl. Acad. Sci. USA*, vol. 92, No. 16, Aug. 1, 1995, pp. 7406–7410.

David S. Finbloom and Andrew C. Larner, "Introduction of Early Response Genes by Interferons, Interleukins, and Growth Factors by the Tyrosine Phosphorylation of Latent Transcription Factors," *Arthritis and Rheumatism*, vol. 38, No. 7, Jul. 1995, pp. 877–889.

J.P. Finnerty, C. Lee, S. Wilson, J. Madden, R. Djukanovic, S. T. Holgate, "Effects of theophylline on inflammatory cells and cytokines in asthmatic subjects: a placebo–controlled parallel group study," *The European Respiratory Journal*, vol. 9, No. 8, Aug. 1996, pp. 1672–1677.

(List continued on next page.)

*Primary Examiner*—Prema Mertz
(74) *Attorney, Agent, or Firm*—Morgan, Lewis & Bockius LLP

(57) ABSTRACT

A C to T DNA variation at position 3365 in exon 5 of the human Asthma Associated Factor 1 (AAF1) produces the predicted amino acid substitution of a methionine for a threonine at codon 117 of AAF1. When this substitution occurs in both alleles in one individual, it is associated with less evidence of atopic allergy including asthma, fewer abnormal skin test responses, and a lower serum total IgE. Thus, applicant has identified the existence of a non-asthmatic, non-atopic phenotype characterized by methionine at codon 117 when it occurs in both AAF1 gene products in one individual.

17 Claims, 29 Drawing Sheets

OTHER PUBLICATIONS

Suzanne Fishman, Kathryn Hobbs and Larry Borish, "Molecular Biology of Cytokines in Allergic Diseases and Asthma," *Immunology and Allergy Clinics of North America*, vol. 16, No. 3, Aug. 1996, pp. 613–642.

Akihiko Gotoh, Hiroyuki Takahira, Charlie Mantel, Sara Litz–Jackson, H. Scott Boswell and Hal E. Broxmeyer, "Steel Factor Induces Serine Phosphorylation of Stat3 in Human Growth Factor–Dependent Myeloid Cells Lines," *Blood*, vol. 88, No. 1, Ju. 1, 1996, pp. 138–145.

Alison Grove and Brian J. Lipworth, "Bronchodilator subsensitivity to salbutamol after twice daily salmeterol in asthmatic patients," *The Lancet*, vol. 346, No. 8968, Jul. 22, 1995, pp. 201–206.

H. J. Gruss, C. Scott, B. J. Rollins, M. A. Brach and F. Herrmann, "Human Fibroblasts Express Functional IL–2 Receptors Formed by the IL–2R α– and β–Chain Subunits," *J. of Immunology*, vol. 157, No. 2, Jul. 15, 1996, pp. 851–857.

Jeannette R. Hill, John A. Corbett, Aaron C. Baldwin and Michael L. McDaniel, "Nitric Oxide Production by the Rat Insulinoma Cell Line, RINm5F, Is Specific for IL–1: A Spectrophotometric IL–1 Bioassay," *Analytical Biochemistry*, vol. 236, No. 1, Apr. 5, 1996, pp. 14–19.

Stephen T. Holgate, Martin K. Church, Peter H. Howarth, E. Newton Morton, Anthony J. Frew and Ratko Djukanović, "Genetic and Environmental Influences on Airway Inflammation in Asthma," *Int. Archive of Allergy and Immunology*, vol. 107, May–Jul. 1995, pp. 29–33.

Stephen K. Horrigan, Carol A. Westbrook, Anne H. Kim, Mekhala Banerjee, Wendy Stock and Richard A. Larson, "Polymerase Chain Reaction—Based Diagnosis of Del(5q) in Acute Myeloid Leukemia and Myelodysplastic Syndrome Identifies a Minimal Deletion Interval," *Blood*, vol. 88, No. 7, Oct. 1, 1996, pp. 2665–2670.

Li Ya Kang and Yu–Chang Yang, "Activation of junB anc c–myc Primary Response Genes by Interleukin 9 in a Human Factor–Dependent Cell Line," *J. of Cellular Physiology*, vol. 163, No. 3, Jun. 1995, pp. 623–630.

Abdenaïm Kermouni, Emiel Van Roost, Karen C. Arden, Joris R. Vermeesch, Suzanne Weiss, Danièle Godelaine, Jonathan Flint, Christophe Lurquin, Jean–Pierre Szikora, Douglas R. Higgs, Peter Marynen, and Jean–Christophe Renauld, "The IL–9 Receptor Gene (IL9R): Genomic Structure, Chromosomal Localization in the Pseudoautosomal Region of the Long Arm of the Sex Chromosomes, and Identification of IL9R Pseudogenes at 9qter, 10pter, 16pter, and 18pter," *Genomics*, vol. 29, No. 2, Sep. 20, 1995, pp. 371–382.

A. Klimka, S. Barth, S. Drillich, W. Wels, J. van Snick, J–C. Renauld, H. Tesch, H. Bohlen, V. Diehl and A. Engert, "A deletion mutant of Pseudomonas exotoxin–A fused to recombinant human interleukin–9 (rhIL–9–ETA) shows specific cytotoxicity against IL–9–receptor–expressing cell lines," *Cytokines and Molecular Therapy*, vol. 2, No. 3, Sep. 1996, pp. 139–146.

M. Thirumala Krishna, Anoop J. Chauhan and Stephen T. Holgate, "Molecular Mediators of Asthma: Current Insights," *Hospital Practice*, vol. 31, No. 10, Oct. 15, 1996, pp. 115–130.

Roberto M. Lemoli, Miriam Fogli, Alessandra Fortuna and Sante Tura, "Interleukin–11 (IL–11) and IL–9 Counteract the Inhibitory Activity of Transforming Growth Factor β3 (TGF–β3) on Human Primitive Hemaptopoietic Progenitor Cells," *Haematologica*, vol. 80, No. 1, Jan.–Feb. 1995, pp. 5–12.

W. Conrad Liles and Wesley C. Van Voorhis, "Review: Nomenclature and Biologic Significance of Cytokines Involved in Inflammation and the Host Immune Response," *J. of Infectious Diseases*, vol. 172, No. 6, Dec. 1995, pp. 1573–1580.

F. J. Lopez–Valpuesta and R. D. Myers, "Cytokines and Thermoregulation: Interleukin–9–Injected in Preoptic Area Fails to Evoke Fever in Rats," *Brain Research Bulletin*, vol. 36, No. 2, 1995, pp. 181–184.

Paolo Macchi, Anna Villa, Silvia Giliani, Maria G. Sacco, Annalisa Frattini, Fulvio Porta, Alberto G. Ugazio, James A. Johnston, Fabio Candotti, John J. O'Shea, Paolo Vezzoni and Luigi D. Notarangelo, "Mutations of Jak–3 gene in patients with autosomal severe combined immune deficiency (SCID)," *Nature*, vol. 337, No. 6544, Sep. 7, 1995, pp. 65–68.

Ikuo Murohashi, Kazuhiro Endoh, Mei Feng, Katsuhiko Yoshida, Hiroko Hirota, Satoru Yoshida, Itsuroh Jinnai, Masami Bessho and Kunitake Hirashima, "Role of Stem Cell Factor in the In Vitro Growth of Blast Clonogenic Cells from Patients with Acute Myeloblastic Leukemia," *J. of Interferon and Cytokine Research*, vol. 15, No. 10, Oct. 1995, pp. 829–835.

Dirkje S. Postma, Eugene R. Bleecker, Pamela J. Amelung, Kenneth J. Holroyd, Jianfeng Xu, Carolien I.M. Panhuysen, Deborah A. Meyers and Roy C. Levitt, "Genetic Susceptibility to Asthma–Bronchial Hyperresponsiveness Coinherited With a Major Gene for Atopy," *The New England J. of Medicine*, vol. 333, No. 14, Oct. 5, 1995, pp. 894–900.

Hans–Christian Reinecker and Daniel K. Podolsky, "Human intestinal epithelial cells express functional cytokine receptors sharing the common γc chain of the interleukin 2 receptor," *Proc. Natl. Acad. Sci. USA*, vol. 92, Aug. 1995, pp. 8353–8357.

Daniel G. Remick, "Cytokines: A Primer for Plastic Surgeons," *Annals of Plastic Surgery*, vol. 35, No. 5, Nov. 1995, pp. 549–559.

Jean–Christophe Renauld, "Interleukin–9: Structural characteristics and biologic properties," *Cytokines: Interleukins and Their Receptors*, vol. 80, 1995, pp. 287–303.

Jean–Christophe Renauld, "Interleukin–9," *Human Cytokines: Handbook for Basic and Clinical Research*, 1996, pp. 1–18.

Jean–Christophe Renauld, Abdenaim Kermouni, Anne Vink, Jamila Louahed and Jacques Van Snick, "Interleukin–9 and its receptor: involvement in mast cell differentiation and T cell oncogenesis," *J. of Leukocyte Biology*, vol. 57, No. 3, Mar. 1995, pp. 353–360.

L. Rosenwasser, J. Dresback, D.J. Klemm, H. Inamura, M. Hermanoff, M. Tarkowski, J. Mascali and L. Borish, "Transcriptional Regulation of the Human IL–9 Gene in Asthma and Atopy," *J. of Investigative Medicine*, vol. 44, No. 3, Mar. 1996, p. 205A.

Leiv S. Rusten, Ingunn Dybedal, Heidi Kiil Blomhoff, Rune Blomhoff, Eriend B. Smeland and Sten Eirik W. Jacobsen, "The RAR–RXR as Well as the RXR–RXR Pathway Is Involved in Signaling Growth Inhibition of Human CD34+ Erythroid Progenitor Cells," *Blood,* vol. 87, No. 5, Mar. 1, 1996, pp. 1728–1736.

Ralf R. Schumann, Takayuki Nakarai, Hans–Jürgen Gruss, Marion A. Brach, Ute von Arnim, Carsten Kirschning, Leonid Karawajew, Wolf–Dieter Ludwig, Jean–Christophe Renauld, Jerome Ritz and Friedhelm Herrmann, "Transcript Synthesis and Surface Expression of the Interleukin–2 Receptor (α–, β–, and γ–Chain) by Normal and Malignant Myeloid Cells," *Blood,* vol. 87, No. 6, Mar. 15, 1996, pp. 2419–2427.

Xiano Jain Sun, Ling–Mel Wang, Yitao Zhang, Lynne Yenush, Martin G. Meyers Jr., Erin Glasheen, William S. Lane, Jacalyn H. Pierce and Morris F. White, "Role of IRS–2 in insulin and cytokine signalling," *Nature,* vol. 377, No. 6545, Sep. 14, 1995.

J. R. Vermeesch, A. Kermonl, J.C. Renauld and P. Marynen, "The IL–9 receptor gene is located in the pseudoautosomal region of the long arm of the sex chromosomes, is expressed from the X and Y chromosome and it murine homologue is located on an autosome," *Chromosome Research,* vol. 3, Sep. 1, 1995, p. 105.

Ziba Razi Wolf, Georg A. Holländer and Hans Reiser, "Activation of CD4+ T lymphocytes from interleukin 2–deficient mice by costimulatory B7 molecules," *Proc. Natl. Acad. Sci. USA.* vol. 93, No. 7, Apr. 2, 1996, pp. 2903–2908.

Y. Yamaoka, M. Kita, T. Kodama, N. Sawai, K. Kashima and J. Imanishi, "Expression of Cytokine mRNA in Gastric Mucosa with *Helicobacter pylori* Infection," *Scandinavian J. of Gastroenterology,* vol. 30, No. 12, Dec. 1995, pp. 1153–1159.

Makoto Yanagida, Hiromi Fukamachi, Kinya Ohgami, Tomoaki Kuwaki, Hiromi Ishii, Hiroya Uzumaki, Kenji Amano, Tomonobu Tokiwa, Hideki Mitsui, Hirohisa Saito, Yoji Iikura, Teruko Ishizaka and Tatsutoshi Nakahata, "Effects of T–Helper 2–Type Cytokines, Interleukin–3 (IL–3), IL–4, and IL–5, and IL–6 on the Survival of Cultured Human Mast Cells," *Blood,* vol. 86, No. 10, Nov. 15, 1995, pp. 3705–3714.

Tinggui Yin, Suzanne R. Keller, Frederick W. Quelle, Bruce A. Witthuhn, Monica Lik–Shing Tsang, Gusav E. Lienhard, James N. Ihle and Yu–Chung Yang, "Interleukin–9 Induces Tyrosine Phosphorylation of Insulin Receptor Substrate–1 via JAK Tyrosine Kinases," *J. of Biological Chemistry,* vol. 270, No. 35, Sep. 1, 1995, pp. 20497–20502.

Tinggui Yin, Liu Yang and Yu–Chung Yang, "Tyrosine Phosphorylation and Activation of JAK Family Tyrosine Kinases by Interleukin–9 in MO7E Cells," *Blood,* vol. 85, No. 11, Jun. 1, 1995, pp. 3101–3106.

Liang–Ji Zhou and Thomas F. Tedder, "A Distinct Pattern of Cytokine Gene Expression by Human CD83+ Blood Dendritic Cells," *Blood,* vol. 86, No. 9, Nov. 1, 1995, pp. 3295–3301.

Yuan Xiano Zhu, Li Ya Kang, Wen Luo, Chou–Chi H. Li, Liu Yang and Yu–Chung Yang, "Multiple Transcription Factors Are Required for Activation of Human Interleukin 9 Gene in T Cells," *J. of Biological Chemistry,* vol. 271, No. 26, Jun. 28, 1996, pp. 15815–15822.

H. Zola, M. Fusco, H. Weedon, P.J. Macardle, J. Ridings and D.M. Roberton, "Reduced expression of the interleukin–2–receptor γ chain on cord blood lymphocytes: relationship to functional immaturity of the neonatal immune response," *Immunology,* vol. 87, No. 1, Jan. 1996, pp. 86–91.

Zhu, Y. X. et al., "Identification of Critical Regulatory Regions in Human Interleukin 9 Gene Promoter," *Blood, J. Amer. Soc. Hematology,* vol. 86, No. 10, Supplemental 1 to Nov. 15, 1995 edition, dated Dec. 1995, p. 2150.

L.C. Borish, J.J. Mascali, M. Klinnert, M. Leppert, L.J. Rosenwasser, "Polymorphisms in the Chromosome 5 Gene Cluster," *J. of Allergy and Clinical Immunology,* vol. 93, No. 1, Part 1, Jan. 1994, p. 345.

William W. Busse, Robert L. Coffman, Erwin W. Gelfand, A.B. Kay and Lanny J. Rosenwasser, "Mechanisms of Persistent Airway Inflammation in Asthma," *Amer. J. of Respiratory and Critical Care Medicine,* vol. 152, No. 1, Jul. 1995, pp. 388–393.

L.J. Rosenwasser, J.K. Dresback, H. Inamura, and D.J. Klemm, "Transcriptional Regulation of the Human IL–4 Gene in Atopy and Asthma," *J. of Investigative Medicine,* vol. 43, Apr. 1995, p. 326.

L.J. Rosenwasser, S. Eisenberg, J. Dresback, D.K. Klemm and L. Borish, "Trancriptional Regulation of Human IL–4," *J. of Allergy and Clinical Immunology,* vol. 93, No. 1, Part 2, Jan. 1994, p. 599.

Roy C. Levitt et al., "Expression of airway hyperreactivity to acetylcholine as a simple autosomal recessive trait in mice," *FASEB,* vol. 2, pp. 2605–2608 (1988).

Roy C. Levitt et al., "A Locus Regulating Bronchial Hyperresponsiveness Maps to Chromosome 5q.," *Amer. J.* Human Genetics, vol. 55, No. 3, pp. 1120, Sep. 1994.

Brooke Taylor Mossman et al., "Advances in Molecular Genetics, Transgenic Models, and Gene Therapy for the Study of Pulmonary Diseases," *Am. J. Respir. Crit. Care Med.,* vol. 151, pp. 2065–2069, (1995).

D. A. Meyers et al., "Evidence for a Locus Regulating Total Serum IgE Levels Mapping to Chromosome 5," *Genomics,* 23:464–470 (1994).

Jean–Christophe Renauld et al., "Expression in Activated CD4+T cells, Genomic Organization, and Comparison with the Mouse Gene," *J. of Immunol.,* vol. 144, pp. 4235–4241, No. 11, Jun. 1, 1990.

Jean–Christophe Renauld et al., "Expression cloning of the murine and human interleukin 9 receptor cDNAs," *Proc. Natl. Acad. Sci. USA,* vol. 89, pp. 5690–5694, Jun. 1992.

Tinggui Yin et al., "JAK1 Kinase Form Complexes with Interleukin–4 Receptor and 4PS/Insulin Receptor Substrate–1–like Protein and Is Activated by Interleukin–4 and Interleukin–9 in T Lymphocytes," *J. Biol. Chem.,* vol. 269, No. 43, pp. 26614–26617 (1994).

International Search Report, dated Feb. 14, 1997.

* cited by examiner

HUMAN    105  YFSCEQPCNQTTAGNALTFLKSLLEIFQKEKMRGMRGKI
HUMAN    105  YFSCEQPCNQTMAGNALTFLKSLLEIFQKEKMRGMRGKI
MURINE   105  SFSCEKPCNQTMAGNTLSFLKSLLGTFQKTEMQRQKSRP

*FIG. 4*

```
           15           30           45           60
            *            *            *            *
TCT CGA GCA GGG GTG TCC AAC CTT GGC GGG GAT CCT GGA CAT CAA CTT CCT CAT CAA CAA
     Q   G   V   S   P   N   L   A   G   D   P   G   I   D   N   F   L   P   H   I   Q   N   K>

75           90          105          120
            *            *            *            *
GAT GCA GGA AGA TCC AGC TTC CAA GTG CCA CTG CAG TGC TAA TGT GAC CAG TTG TCT CTG
 M   Q   D   P   E   A   S   D   F   K   V   P   H   C   Q   S   C   *   N   V   T   D   Q   L   S   C   L   C>

135          150          165          180
            *            *            *            *
TTT GGG CAT TCC CTC TGA CAA CAA CTG CAC CAG ACC ATG CTT CAG TGA GAG ACT GTC TCA GAT
 L   G   I   P   S   *   M   Q   N   D   R   T   H   Q   Q   T   P   M   L   F   S   *   E   R   T   V   S   Q   M>

195          210          225          240
            *            *            *            *
GAC CAA TAC CAC CAT GCA AAC AAG ATA CCC ACT GAT TTT TTC CTG GGT GAA AAA ATC TCA AGT
 T   D   N   Y   T   M   Q   N   K   R   Y   P   L   I   F   D   S   F   C   R   V   K   K   S   Q   V>

255          270          285          300
            *            *            *            *
TGA AGT ACT AAA GAA CAA CAA GTG TCC ATA TTT CTG TGA GAG TCT TCT GGA ACA GCC ATG CAA CCA AAC
 *   S   K   N   T   K   E   N   Q   V   S   Y   P   F   S   L   *   E   S   L   L   E   T   Q   A   P   M   Q   P   N   Q   T>

315          330          345          360
            *            *            *            *
CAC AGG CAA GAA CGC GCT GAC ATT TCT GAA GAG TCT TCT GAA ATG AAG ATG AAA TAT TTT CCA AAT AGA AAA
 T   N   G   R   Q   N   A   L   D   F   L   T   K   L   E   S   L   L   E   K   I   F   Q   E   K>

375          390          405
            *            *            *
GAT GAG AGG GAT GAG AGG CAA GAT ATG AAG ATG AAA TAT TAT TTA TCC CAG CTG C
 M   R   G   M   E   R   D   Q   R   D   K   I   *   >
```

```
           15        30        45        60
            *         *         *         *
TCT CGA GCA GGG GTG TCC AAC CTT GGC GAT CCT GGA CAT CAA CTT CCT CAT CAA CAA
                Q   G   C   P   T   L   A   G   I   D   L   P   H   I   N   F   L   P   H   Q   N   K>

75        90       105       120
            *         *         *         *
GAT GCA GGA AGA TCC AGC TTC CAA GTG CCA CTG CAG TGC TAA TGT GAC CAG TCT CTG
 M   Q   E   D   P   A   S   F   Q   V   P   L   Q   C   *   N   V   D   Q   S   L   C>

135       150       165       180
            *         *         *         *
TTT GGG CAT TCC CTC TGA CAA CTG CAC CAG ACC ATG CTT CAG TGA GAG ACT GTC TCA GAT
 L   G   H   S   L   *   Q   L   H   Q   T   M   L   Q   *   E   R   L   S   Q   M>

195       210       225       240
            *         *         *         *
GAC CAT GCA AAC AAG ATA CCC ACT GAT TTT TTC CTG TGA GGT GAA AAA ATC AGT
 T   M   Q   N   K   I   R   Y   P   T   D   F   F   L   *   G   E   K   I   S   V>

255       270       285       300
            *         *         *         *
CAA TAC CAC CAT GCA AAC AAG ATA CCC ACT GAT TTT TTC CTG TGA ACA GCC CAA CCA AAC
 N   T   T   M   Q   N   K   I   R   Y   P   T   D   F   F   S   C   E   Q   P   N   Q   T>

315       330       345       360
            *         *         *         *
GAC AGT ACT AAA GAA CAA CAA GTG TCC GAA GAG TCT TCT GGA AAT TTT CCA GAA AGA AAA
 E   V   L   K   E   Q   Q   V   S   E   E   S   L   L   E   I   F   Q   E   K>

375       390       405
            *         *         *
CAT GGC AGG CAA CGC GCT GAC ATT TCT GAA AAG ATG AAA TAT TAT TCC CAG CTG C
 M   A   G   Q   R   A   D   I   S   E   K   M   K   Y   Y   S   Q   L>

GAT GAG AGG GAT GAG AGG CAA GAT ATG
 M   R   G   M   R   G   K   I   *   >
```

```
ATG AAA ACA GCT ATC GCA GTG GCA CTG GCT GGT TTC GCT ACC GTT GCG CAA
Met Lys Thr Ala Ile Ala Val Ala Leu Ala Gly Phe Ala Thr Val Ala Gln
                15*             30*             45*             60*

GCT GAC TAC AAG GAC GAT GAC AAG CTT GGT GCT AGA GAT AGA TCT
Ala Asp Tyr Lys Asp Asp Asp Lys Leu Gly Ala Arg Asp Arg Ser
         75*             90*             105*            120*

CTC GAG CAG CCA ACC TTG GAC AAG TCT AGA ATC GTT GAC AGA TCT
Leu Glu Gln Pro Thr Leu Asp Lys Ser Arg Ile Val Asp Arg Ser
         135*            150*            165*            180*

ATG GAG GAA TGT TCC AAG CTG TGC AAG ATC CTG GAC ATC AAC AAG
Met Glu Glu Cys Ser Lys Leu Cys Lys Ile Leu Asp Ile Asn Lys
         195*            210*            225*            240*

TTG GGG GAT TCT GCT AGT GTT AAT AAT GTG ACC AGT CTC TGT
Leu Gly Asp Ser Ala Ser Val Asn Asn Val Thr Ser Leu Cys
210*                    255*            270*            285*  300*

ACC AAT GAC TGC TGC TTC AGA AGA TGC GAG TCT AGT AGT ATG
Thr Asn Asp Cys Cys Phe Arg Arg Cys Glu Ser Ser Ser Met
         315*            330*            345*            360*

GAA GTA ATG CAA AGA TAC ATT CCA TAT TGT GAA CTG CGG GTT
Glu Val Met Gln Arg Tyr Ile Pro Tyr Cys Glu Leu Arg Val
         375*            390*            405*            420*

ACG AAT AAA AAC TTT CTG CAA ATT CAG GAA AAA CAG ACC
Thr Asn Lys Asn Phe Leu Gln Ile Gln Glu Lys Gln Thr
         435*            450*            465*  480*

ACG GCA GCG CTG ACA TTT CTT CAG GAA ATT TTC TTT CAG AAA GAA AAG
Thr Ala Ala Leu Thr Phe Leu Gln Glu Ile Phe Phe Gln Lys Glu Lys
         495*            510*            525*                 540*

ATG AGA GGG ATG GGC AAG ATA TGA AAG GGC TGT AAC CCA TGC CAA AAG
Met Arg Gly Met Gly Lys Ile ***  Lys Gly Cys Asn Pro Cys Gln Lys
         555*            570*    585*

TAG CGA AAC CAG CCA GTG CCA CTG CAA TCG CGA TAG CTG TCT TTT
```

KP-16    SER ASP ASN ALA THR ARG PRO ALA PHE SER GLU ARG LEU SER GLN MET THR ASN
(SEQ ID NO: 13)

KP-20    PHE SER ARG VAL LYS LYS SER VAL GLU VAL LEU LYS ASN ASN LYS ALA PRO TYR
(SEQ ID NO: 14)

KP-23    GLU GLN PRO ALA ASN GLN THR THR ALA GLY ASN ALA LEU THR PHE LEU LYS SER
(SEQ ID NO: 15)

| DOUBLE-AGENT™ CROSS-LINKER NUMBER | DOUBLE-AGENT™ CROSS-LINKER NUMBER | REACTIVE TOWEL | | | | | CLEARABLE BY | | | | LEDIA-TABLE | |
|---|---|---|---|---|---|---|---|---|---|---|---|---|
| | | -NH2 AMINOS | -SM SULFH-YDRYLS | CARBO-HYDRATES | NON-SELACTIVE (PHOTO-REACTIVE) | -COOM CORBOXYLS | THIOLS | BASE | PERIODOLE | HYDROXYLOMINO | YES | NO |
| 21510 | ABH | | | x | | | | | | | | x |
| 21551 | ANB-NOS | x | | | x | | | | | | | x |
| 27720 | APDP | | x | | x | | x | | | | x | |
| 20107 | APG | | x | | x | | | | | | | x |
| 21511 | ASIB | | | | x | | | | | | x | |
| 21512 | ASBA | | | | x | x | | | | | x | |
| 21564 | BASED | | | | | | | | | | x | |
| 21579 | BSA | x | | | | | x | | | | | x |
| 21319 | BMH | | x | | | | | | | | | x |
| 21554 | BSOCOES | x | | | | | | | | | | x |
| 21524 | DFDNB | x | | | | | | | | | | x |
| 20664 | DMA | x | | | | | | | | | | x |
| 20666 | DMP | x | | | | | | | | | | x |
| 20668 | DMS | x | | | | | | | | | | x |
| 21701 | DPDPB | x | | | | | x | | | | | x |
| 20592 | DSG | x | | | | | | | | | | x |
| 22585 | DSP | x | | | | | x | | | | | x |
| 21555 | DSS | x | | | | | | | | | | x |
| 21590 | DST | x | | | | | | | x | | | | x |
| 20665 | DTB | x | | | | | x | | | | | x |
| 21577 | DTSSP | x | | | | | x | | | | | x |
| 22980 | EDC | x | | | | | | | | | | x |
| 21565 | EGS | x | | | | x | | | | | | x |
| 22314 | GMBS | x | x | | | | | | | | | x |
| 21560 | HSAB | x | | | x | | | | | | | x |
| LC-SPDP | LC-SPDP | x | x | | | | x | | | | | x |
| 21651 | MBS | x | x | | | | | | | | | x |
| 22310 | M2C2H | | | x | x | | | | | | | x |
| 22304 | MPBH | x | | | x | | | | | | | x |
| 22302 | NHSASA | | x | | | | x | | | x | | |
| 27715 | | | | | | | | | | | | x |

FIG. 26(cont.)

| DOUBLE-AGENT™ CROSS-LINKER NUMBER | DOUBLE-AGENT™ CROSS-LINKER NUMBER | REACTIVE TOWEL | | | | | CLEARABLE BY | | | | LEDIA-TABLE | |
|---|---|---|---|---|---|---|---|---|---|---|---|---|
| | | -NH2 AMINOS | -SM SULFHYDRYIS | CARBO-HYDRATES | NON-GELACTIVE (PHOTO-REACTIVE) | -COOM CORBOXYLS | THIOLS | BASE | PERIODOLE | HYDROXYLOMINO | YES | NO |
| 22300 | PDPH | x | x | x | | | x | | | | | x |
| 20669 | PNPDTP | x | | | x | | | | | | | x |
| 21552 | SADP | x | | | x | | x | | | | | x |
| 33030 | SAED | x | | | x | | x | | | | | x |
| 21549 | SAND | x | | | x | | x | | | | | x |
| 22588 | SANPAH | x | | | x | | | | | | | |
| 27716 | SASD | x | | | | | x | | | | x | |
| 22340 | SDBP | x | | | | | | | | | | x |
| 22325 | SIAB | x | x | | | | | | | | | x |
| 22320 | SMCC | x | x | | | | | | | | | x |
| 22315 | SMBP | x | x | | | | | | | | | x |
| 21558 | SMPT | x | x | | | | x | | | | | x |
| 21557 | SPDP | x | x | | | | x | | | | | x |
| 21556 | Sulfo-BSOCOES | x | | | | | | x | | | | x |
| 20591 | Sulfo-DST | x | | | | | | | x | | | x |
| 21566 | Sulfo-EGS | x | | | | | | | | | | x |
| 22324 | Sulfo-GMBS | x | x | | | | | | | | | x |
| 21561 | Sulfo-HSAB | x | | | x | | | | | x | | x |
| 21650 | Sulfo-LC-SPDP | x | x | | | | x | | | | | x |
| 22312 | Sulfo-MBS | x | x | | | | | | | | | |
| 27725 | Sulfo-NHS-ASA | x | | | x | | | | | | x | |
| 27735 | Sulfo-NHSS-LC-ASA | x | | | x | | | | | | x | x |
| 21553 | Sulfo-SADP | x | | | x | | | | | | | x |
| 33075 | Sulfo-SAMCA | x | | | x | | x | | | | | x |
| 22389 | SulfoSANPAH | x | | | x | | | | | | | x |
| 21562 | Sulfo-SAPB | x | | | | | | | | | | x |
| 21327 | Sulfo-SIAB | x | x | | | | | | | | | x |
| 22322 | Sulfo-SMCC | x | x | | | | | | | | | x |
| 22317 | Sulfo-SMBP | x | x | | | | | | | | | x |
| 21568 | Sulfo-LC-SMPT | x | x | | | | | | | | | x |

1. 1505
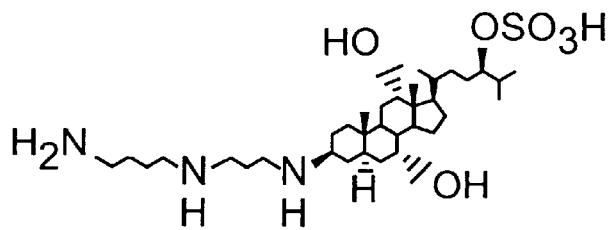
2. preSQLS-658 (NOT DETERMINED)
3. 1360
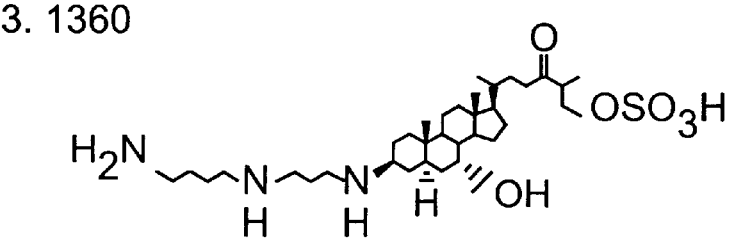
4. 1361
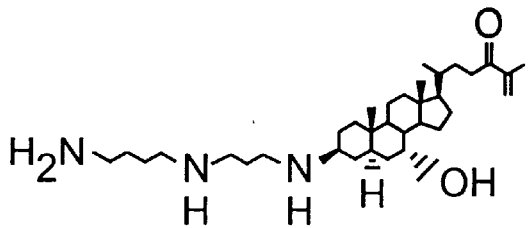
5. preSQHS-642 (NOT DETERMINED)
6. preSQHS-781 (NOT DETERMINED)
7. dessulfateSQ (NOT DETERMINED)
*FIG. 27*

METHODS OF TREATING ASTHMA WITH INTERLEUKIN-9 ANTIBODIES

CROSS-REFERENCE TO RELATED APPLICATION

This is a continuation of Application Ser. No. 08/874,503 filed Jun. 13, 1997, now abandoned which is a divisional of Application Ser. No. 08/697,472 filed Aug. 23, 1996, now abandoned which is based on provisional Application Serial No. 60/002,765, filed Aug. 24, 1995, all of which are herein incorporated by reference in their entirety as are all references and patents referred to in this application.

FIELD OF THE INVENTION

This invention relates to regulating IL-9 activity and treating atopic allergies and related disorders like asthma, based upon the relationship between IL-9 and its receptor.

BACKGROUND OF THE INVENTION

Inflammation is a complex process in which the body's defense system combats foreign entities. While the battle against foreign entities may be necessary for the body's survival, some defense systems improperly respond to foreign entities, even innocuous ones, as dangerous and thereby damage surrounding tissue in the ensuing battle.

Atopic allergy is an ecogenetic disorder, where genetic background dictates the response to environmental stimuli. The disorder is generally characterized by an increased ability of lymphocytes to produce IgE antibodies in response to ubiquitous antigens. Activation of the immune system by these antigens leads to allergic inflammation and may occur after ingestion, penetration through the skin, or after inhalation. When this immune activation occurs and pulmonary inflammation ensues this disorder is broadly characterized as asthma. Certain cells are critical to this inflammatory reaction and they include T cells and antigen presenting cells, B cells that produce IgE, and mast cells/basophils and eosinophils that bind IgE. These inflammatory cells accumulate at the site of allergic inflammation and the toxic products they release contribute to the tissue destruction related to the disorder.

While asthma is generally defined as an inflammatory disorder of the airways, clinical symptoms arise from intermittent air flow obstruction. It is a chronic disabling disorder that appears to be increasing in prevalence and severity[1]. It is estimated that 30–40% of the population suffer with atopic allergy, and 15% of children and 5% of adults in the population suffer from asthma.[1] Thus, an enormous burden is placed on our health care resources.

The mechanism of susceptibility to atopy and asthma remains unknown. Interestingly, while most individuals experience similar environmental exposures, only certain individuals develop atopic allergy and asthma. This hypersensitivity to environmental allergens known as "atopy" is often indicated by elevated serum IgE levels or abnormally great skin test response to allergens in atopic individuals as compared to nonatopics.[10] Strong evidence for a close relationship between atopic allergy and asthma is derived from the fact that most asthmatics have clinical and serologic evidence of atopy.[4-9] In particular, younger asthmatics have a high incidence of atopy.[10] In addition, immunologic factors associated with an increase in serum total IgE levels are very closely related to impaired pulmonary function.[3]

Both the diagnosis and treatment of these disorders are problematic.[1] The assessment of inflamed lung tissue is often difficult, and frequently the source of the inflammation cannot be determined. Without knowledge of the source of the airway inflammation and protection from the inciting foreign environmental agent or agents, the inflammatory process cannot be interrupted. It is now generally accepted that failure to control the pulmonary inflammation leads to significant loss of lung function over time.

Current treatments suffer their own set of disadvantages. The main therapeutic agents, β agonists, reduce the symptoms, i.e., transiently improve pulmonary functions, but do not affect the underlying inflammation so that lung tissue remains in jeopardy. In addition, constant use of β agonists results in desensitization which reduces their efficacy and safety.[2] The agents that can diminish the underlying inflammation, the anti-inflammatory steroids, have their own known list of disadvantages that range from immunosuppression to bone loss.[2]

Because of the problems associated with conventional therapies, alternative treatment strategies have been evaluated.[65-66] Glycophorin A,[64] cyclosporin,[65] and a nonapeptide fragment of IL-2,[63] all inhibit interleukin-2 dependent T lymphocyte proliferation and therefore, IL-9 production,[51] however, they are known to have many other effects.[2] For example, cyclosporin is used as a immunosuppressant after organ transplantation. While these agents may represent alternatives to steroids in the treatment of asthmatics,[63-66] they inhibit interleukin-2 dependent T lymphocyte proliferation and potentially critical immune functions associated with homeostasis. What is needed in the art is the identification of a pathway critical to the development of asthma that explains the episodic nature of the disorder and the close association with allergy that is downstream of these critical immune functions. Nature demonstrated that this pathway is the appropriate target for therapy since biologic variability normally exists at this pathway and these individuals are otherwise generally not immunocompromised or ill except for their symptoms of atopy.

Because of the difficulties related to the diagnosis and treatment of asthma, the complex pathophysiology of this disorder is under intensive study. Although this disorder is heterogeneous and may be difficult to define because it can take many forms, certain features are found in common among asthmatics. Examples of such traits include elevated serum IgE levels, abnormal skin test response to allergen challenge, bronchial hyperresponsiveness [BHR], bronchodilator reversibility, and airflow obstruction.[3-10] These expressions of these asthma related phenotypes may be studied as quantitative or qualitative measures.

Elevated IgE levels are also closely correlated with BHR, a heightened bronchoconstrictor response to a variety of stimuli.[4,6,8,9] BHR is believed to reflect the presence of airway inflammation,[6,8] and is considered a risk factor for asthma.[11-12] BHR is accompanied by bronchial inflammation and an allergic diathesis in asthmatic individuals.[13-21] Even in children with no symptoms of atopy and asthma, BHR is strongly associated with elevated IgE levels.[19]

A number of studies document a heritable component to atopy and asthma.[4,10,21] However, family studies have been difficult to interpret since these disorders are significantly influenced by age and gender, as well as many environmental factors such as allergens, viral infections, and pollutants.[22-24] Moreover, because there is no known biochemical defect associated with susceptibility to these disorders, the mutant genes and their abnormal gene products can only be recognized by the anomalous phenotypes they produce. Thus, an important first step in isolating and characterizing a heritable component is identifying the chromosomal locations of the genes.

Cookson et al. provided the first description of a genetic localization for inherited atopy.[25] These investigators described evidence for genetic linkage between atopy and a single marker on a specific chromosomal region designated 11q13.1. Later, they suggested evidence of maternal inheritance for atopy at this locus.[26] Although maternal inheritance [genetic imprinting] had been observed for atopy, it had never been explained previously. However, efforts to confirm this linkage have not been generally successful.[27-31]

Recently, the β subunit of the high-affinity IgE receptor was mapped to chromosome 11q, and a putative mutation associated with atopy has been described in this gene.[32,33] However, because of the difficulties by others of replicating this linkage, the significance of this gene and polymorphism remains unclear. While additional studies will be required to confirm whether this putative mutation causes atopy in the general population, data collected so far suggests this polymorphism is unlikely to represent a frequent cause of atopy.

Because serum IgE levels are so closely associated with the onset and severity of allergy and asthma as clinical disorders, attention has focused on studies of the genetic regulation of serum total IgE levels. While past studies have provided evidence for Mendelian inheritance for serum total IgE levels,[34-38] an indication of the existence of one regulatory gene, others have found evidence for polygenic inheritance of IgE, i.e., existence of several responsible genes.[39]

Artisans have found several genes that may be important in the regulation of IgE and the development or progression of bronchial inflammation associated with asthma on chromosome 5q. They include genes encoding several interleukins, such as IL-3, IL-4, IL-5, IL-9, IL-13, granulocyte macrophage colony stimulating factor [GM CSF], a receptor for macrophage colony stimulating factor [CSF-1R], fibroblast growth factor acidic [FGFA], as well as others.[40] Recent evidence from family studies suggests genetic linkage between serum IgE levels and DNA markers in the region of these candidate genes on chromosome 5q.[41,42] Together, these investigations suggest that one or more major genes in the vicinity of the interleukin complex on chromosome 5q regulates a significant amount of the observed biologic variability in serum IgE that is likely to be important in the development of atopy and asthma.

Linkage [sib-pair analyses] was also used previously to identify a genetic localization for BHR.[79] Because BHR was known to be associated with a major gene for atopy, chromosomal regions reported to be important in the regulation of serum IgE levels were examined.[42] Candidate regions for atopy have been identified by linkage analyses. These studies identified the existence of a major gene for atopy on human chromosome 5q31-q33.[42]

Therefore, to determine the chromosomal location of a gene[s] providing susceptibility to BHR, which would be coinherited with a major gene for atopy, experiments were carried out using linkage analyses between BHR and genetic markers on chromosome 5q.[42,79,82] Individuals with BHR were identified by responsiveness to histamine. Markers useful for mapping asthma-related genes are shown in FIG. 1.

Specifically, gene candidates for asthma, bronchial hyperresponsiveness, and atopy are shown [right] in their approximate location relative to the markers shown. The map includes the interleukin genes IL-4, IL-13, IL-5, and IL-3; CDC25, cell division cycle-25; CSF2, granulocyte-macrophage colony stimulating factor [GMCSF]; EGR1 early growth response gene-1; CD14, cell antigen 14; ADRB2, the β2-adrenergic receptor; GRL1, lymphocyte-specific glucocorticoid receptor; PDGFR, platelet-derived growth factor receptor. Bands 5q31-q33 extend approximately from IL-4 to D5S410. The distances reported are sex-averaged recombination fractions.

Affected sib-pair analyses demonstrated statistically significant evidence for linkage between BHR and D5S436, D5S658, and several other markers located nearby on chromosome 5q31-q33.[79] These data strongly supported the hypothesis that one or more closely spaced gene[s] on chromosome 5q31-q33 determine susceptibility to BHR, atopy, and asthma.[79,80,81,82]

Recently linkage has also been demonstrated between the asthma phenotype and genetic markers on chromosome 5q31-q33.[83] This region of the human genome was evaluated for linkage with asthma because of the large number of genes representing reasonable positional candidates for providing genetic susceptibility for atopy and BHR.

Linkage was demonstrated using the methods described above.[42,83] Specifically, 84 families were analyzed from the Netherlands with both sib-pair and LODs for markers from this same region of chromosome 5q previously shown to be linked to BHR and atopy.[42,83] An algorithm was used to categorize obstructive airways disease in the asthmatic probands and their families. This classification scheme was based, as described previously, on the presence or absence of BHR to histamine, respiratory symptoms, significant smoking history [>5 pack years], atopy as defined by skin test response, airway obstruction [FEV1% predicted<95% CI] and reversibility to a bronchodilator [>9% predicted].

Evidence was found for linkage between asthma and markers on chromosome Sq by affected sib pair analysis (N=10, P<0.05) and by maximum likelihood analysis with a dominant model for the asthma phenotype.[83]

Asthma was linked to D5S658 with a maximal LOD of 3.64 at $\theta=0.03$, using a dominant model [class 1 affected, class 2–4 uncertain, class 5 unaffected] with a gene frequency of 0.015 [prevalence of 3%]. A maximal LOD of 2.71 at $\theta=0.0$ was observed for D5S470 which is approximately 5cM telomeric, or away from IL-9, relative to D5S436.[83]

Subsequent to the original filing of this application, IL-9 or a gene nearby was suggested as likely to be important use atopy and asthma.[43] The IL-9 suggestion was based on a strong correlation in a randomly ascertained population between log serum total IgE levels and alleles of a genetic marker in the IL-9 gene.[43] This type of association with one or more specific alleles of a marker is termed "linkage disequilibrium", and generally suggests that a nearby gene determines the biologic variability under study.[44]

The IL-9 gene has been mapped to the q31-q33 region of chromosome 5.[40] Only a single copy of the gene is found in the human genome.[45,46] Structural similarity has been observed for the human and murine IL-9 genes.[45,46] Each gene consists of five exons and four introns extending across approximately four Kb of DNA. Expression of the gene appears to be restricted to activated T cells.[45,46]

The functions of IL-9 now extend well beyond those originally recognized. While IL-9 serves as a T cell growth factor, this cytokine is also known to mediate the growth of erythroid progenitors, B cells, mast cells, and fetal thymocytes.[45,46] IL-9 acts synergistically with IL-3 in causing mast cell activation and proliferation.[47] This cytokine also potentiates the IL-4 induced production of IgE, IgG, and IgM by normal human B lymphocytes.[48] IL-9 also potentiates the IL-4 induced release of IgE and IgG1 by murine B lymphocytes.[49] A critical role for IL-9 in the mucosal inflammatory response to parasitic infection has also been demonstrated.[50,51]

In addition to IL-9, chromosome 5q bears numerous other gene candidates including IL-3, IRF1, EGR1, ITK, GRL1, ADRB2, CSF1R, FGFA, ITGA2, CD14, PDGFR, CDC25, CSF2, IL-4, IL-5, IL-12B, and IL-13. These may all be important in atopic allergy and as potential targets for therapeutic development. Moreover, the art lacks any knowledge regarding how the sequence of IL-9 or the function of IL-9 specifically correlates with atopic allergy, asthma, or bronchial hyperresponsiveness. Without such knowledge, artisans would not know how or whether to use IL-9 to either diagnose or treat these disorders.

The art does provide that IL-9 is a novel cytokine having an apparent molecular weight of approximately between 20 to 30 kD as determined by sodium dodecyl sulfate polyacrylamide gel electrophoresis under reducing conditions. It is produced as a 144 amino acid protein, that is processed to a 126 amino acid glycoprotein. Yang et al.[85] disclose that the DNA sequence encoding IL-9 comprises approximately 630 nucleotides, with approximately 450 nucleotides in the proper reading frame for the protein.

It is also known in the art that multiple protein isoforms may be generated from a single genetic locus by alternative splicing. Alternative splicing is an efficient mechanism by which multiple protein isoforms may be generated from a single genetic locus. Alternative splicing is used in terminally differentiated cells to reversibly modify protein expression without changing the genetic content of the cells. These protein isoforms are preferentially expressed in different tissues or during different states of cell differentiation or activation. Protein isoforms may have different functions and Alms and White have cloned and expressed a naturally occurring splice variant of IL-4, formed by the omission of exon 2, thus called IL-4δ2.[86] It was observed that IL-4δ2 inhibits T-cell proliferation induced by IL-4.

However, the art lacks any knowledge about IL-9 protein isoforms which are formed by deletions of exons 2 and 3 or the regulatory functions exhibited by these truncated proteins. Specifically, their role in regulating the biological activity, namely, the down-regulation of IL-9 expression or activity is unclear. Moreover, the formation of such isoforms by alternative splicing has not been previously observed or used to provide variants of IL-9 which function as agonists or antagonists of the native cytokine.

The art also lacks any knowledge about the role of the IL-9 receptor with asthma-related disorders. It is known that IL-9 binds to a specific receptor expressed on the surface of target cells.[46,52,53] The receptor actually consists of two protein chains: one protein chain, known as the IL-9 receptor, binds specifically with IL-9 and the other protein chain is the chain, which is shared in common with the IL-2 receptor.[46] In addition, the human IL-9 receptor cDNA has been cloned.[46,52,53] This cDNA encodes a 522 amino acid protein which exhibits significant homology to the murine IL-9 receptor. The extracellular region of the receptor is highly conserved, with 67% homology existing between the murine and human proteins. The cytoplasmic region of the receptor is less highly conserved. The human cytoplasmic domain is much larger than the corresponding region of the murine receptor.[46]

The IL-9 receptor gene has also been characterized.[53] It is thought to exist as a single copy in the mouse genome and is composed of nine exons and eight introns.[53] The human genome contains at least four IL-9 receptor pseudogenes. The human IL-9 receptor gene has been mapped to the 320 kb subtelomeric region of the sex chromosomes X and y.[46] Nonetheless, despite these studies, the art lacks any knowledge of a relation between the IL-9 receptor and atopic allergy, asthma, or bronchial hyperresponsiveness.

Thus, the art lacks any knowledge of how the IL-9 gene, its receptor, and their functions, are related to atopic allergy, asthma, bronchial hyperresponsiveness, and related disorders. Therefore, there is a specific need in the art for genetic information on atopic allergy, asthma, bronchial hyperresponsiveness, and for elucidation of the role of IL-9 in the etiology of these disorders. There is also a need for elucidation of the role of the IL-9 receptor and the IL-9 receptor gene in these disorders. Furthermore, most significantly, based on this knowledge, there is a need for the identification of agents which are capable of regulating the interaction between IL-9 and its receptor for treating these disorders.

SUMMARY OF THE INVENTION

Applicant has satisfied the long felt need for a treatment for atopic allergy including asthma and related disorders by providing information demonstrating the role of IL-9 (also known as Asthma Associated Factor 1, or AAFI) in the pathogenesis of these disorders which information has led to compounds that are capable of regulating the activity of IL-9. Applicant has also demonstrated conserved linkage and synteny homologies between mice and humans for a gene that determines biologic variability in airway hyperresponsiveness. These relationships specifically identify IL-9 as a gene candidate. In addition, applicant has determined that IL-9 is critical to a number of antigen-induced responses in mice including bronchial hyperresponsiveness, eosinophilia and elevated cell counts in bronchial lavage, and elevated serum total IgE. These findings typify the allergic inflammation associated with asthma.

Furthermore, applicant has determined that a C to T nucleic acid variation at position 3365 in exon 5 of the human IL-9 gene produces the predicted amino acid substitution of a methionine for a threonine at codon 117 of IL-9. When this substitution occurs in both alleles in one individual, it is associated with less evidence of atopic allergy including asthma, fewer abnormal skin test responses, and a lower serum total IgE. Thus, applicant has identified the existence of a nonasthmatic, nonatopic phenotype characterized by methionine at codon 117 when it occurs in both IL-9 gene products in one individual. As an additional significant corollary, applicant has identified the existence of susceptibility to an asthmatic, atopic phenotype characterized by a threonine at codon 117. Thus, the invention includes purified and isolated DNA molecules having such a sequence as well as the peptides encoded by such DNA.

The biological activity of IL-9 results from its binding to the IL-9 receptor and the consequent propagation of a regulatory signal in specific cells. Therefore, IL-9 functions can be interrupted or regulated by the interaction of IL-9 agonists or antagonists with IL-9 or its receptor. Down regulation, i.e. reduction of the functions controlled by IL-9, is achieved in a number of ways. Administering agonists or antagonists that can interrupt the binding of IL-9 to its receptor is one key mechanism and such agonists and antagonists are within the claimed invention. Examples include administration of polypeptide products encoded by the DNA sequences of IL-9 or IL-9 receptor wherein the DNA sequences contain various mutations. These mutations may be point mutations, insertions, deletions, or spliced variants of IL-9 or its receptor.

A further embodiment of this invention includes the regulation of the activity of IL-9 by administering "agonists and antagonists." The skilled artisan will readily recognize that all molecules containing the requisite 3-dimensional structural conformation and which contain the residues essential or critical for receptor binding are within the scope of this invention. Specifically, residues 43–60 and 71–90 of the mature protein appear to be important for receptor binding. Applicant has shown that peptides KP-16 (residues 43–60) and KP-20 (residues 71–90) act as receptor antagonists. In addition, these residues in the native IL-9 molecule are predicted to form anti-parallel helical structures. The three dimensional structure of the protein suggests that specifically serine 52 and/or glutamic acid 53 interact with lysine 85, serine 56 interacts with lysine 82, and threonine 59 interacts with valine 78. The three dimensional coordinates of these anti-parallel helices and the related functional groups represent the requisite 3-dimensional conformation critical for receptor binding and compounds which simulate these relationships are within the scope of this invention.

The biological activity of the IL-9 receptor (also called Asthma Associates Factor 2, AAF2) can also be modulated by using soluble IL-9 receptor molecules. Such a molecule prevents the binding of IL-9 to the cell-bound receptor and acts as an antagonist for IL-9, and is also within the scope of this invention.

Polyclonal and monoclonal antibodies which block the binding of IL-9 to its receptor are also within the scope of this invention and are useful therapeutic agents in treating atopic allergy including asthma and related disorders.

Another embodiment of this invention relates to the use of isolated DNA sequences containing various mutations such as point mutations, insertions, deletions, or spliced mutations of IL-9 or the IL-9 receptor in gene therapy.

Expression of IL-9 and IL-9 receptor is also down-regulated by administering an effective amount of synthetic antisense oligonucleotide sequences. The oligonucleotide compounds of the invention bind to the mRNA coding for human IL-9 and IL-9 receptor thereby inhibiting expression of these molecules.

The structure of both IL-9 and the IL-9 receptor have been examined and analyzed in great detail and amino acid residues of IL-9 critical for receptor binding have been identified. Based on structural studies and the binding characteristics of this specific binding pair, this invention further includes small molecules tailored such that their structural conformation provides the residues essential for blocking the interaction of IL-9 with the IL-9 receptor. Such blockade results in modulation of the activity of the receptor and these molecules are, therefore, useful in treating atopic allergies.

Another embodiment of this invention is directed to the regulation of downstream signaling pathways necessary for IL-9 function. IL-9 induces tyrosine phosphorylation of Stat3 which appears to be unique to the IL-9 signaling pathway[58] and is useful as a target for inhibitors. Specific and nonspecific inhibitors of tyrosine kinase such as tyrophostins are, therefore, useful in downstream regulation of the physiological activity of IL-9, and are part of the invention.

In a further embodiment aminosterol compounds are also useful in treating atopic allergies and related disorders because they are also involved in blocking signal transduction of the IL-9 signal transduction pathway.

The products discussed above represent various effective therapeutic agents in treating atopic allergies, asthma and other related disorders.

This invention also includes the truncated polypeptides encoded by the DNA molecules described above. These polypeptides are capable of regulating the interaction of IL-9 with the IL-9 receptor.

Thus, applicant has identified the critical role of the IL-9 pathway in pathogenesis of atomic allergy, including bronchial hyperresponsiveness, asthma, and related disorders. More specifically, applicant has provided antagonists and methods of identifying antagonists that are capable of regulating the interaction between IL-9 and its receptor. Applicant also provides methods for regulating the activity of IL-9 by: 1) administering a compound having activity comparable to IL-9 containing methionine at codon 117 and the ability to bind to a receptor for IL-9 in an amount sufficient to down-regulate the activity of IL-9; and 2) by administering truncated protein products encoded by isolated nucleic acid sequences comprising deletions of any one or more of exons 1, 2, 3, 4, or 5.

Having identified the critical role of the IL-9 pathway in atopic allergy, bronchial hyperresponsiveness, and asthma, applicant also provides a method for the diagnosis of susceptibility to atopic allergy, asthma, and related disorders. Lastly, applicant provides a method for assaying the functions of IL-9 and its receptor to identify compounds or agents that may be administered in an amount sufficient to down-regulate either the expression or functions of IL-9 and the IL-9 receptor.

The accompanying figures, which are incorporated in and constitute a part of this specification, illustrate several embodiments of the invention and, together with the description, serve to explain the principle of the invention.

BRIEF DESCRIPTION OF THE DRAWINGS

FIG. 4: Alignment of amino acid sequences corresponding to exon 5 of the human and murine IL-9 genes. The first sequence is translated from the Thr allele of the human gene. The middle sequence is translated from the Met allele of the human gene. The final sequence is translated from the murine gene.

FIG. 7: Translated cDNA sequence of Thr117 version of IL-9.

FIG. 8: Translated cDNA sequence of Met117 version of IL-9.

FIG. 10: Sequence of pFlag expression construct for the Thr117 version of the cDNA from the region surrounding the site of ligation.

Figure 12:
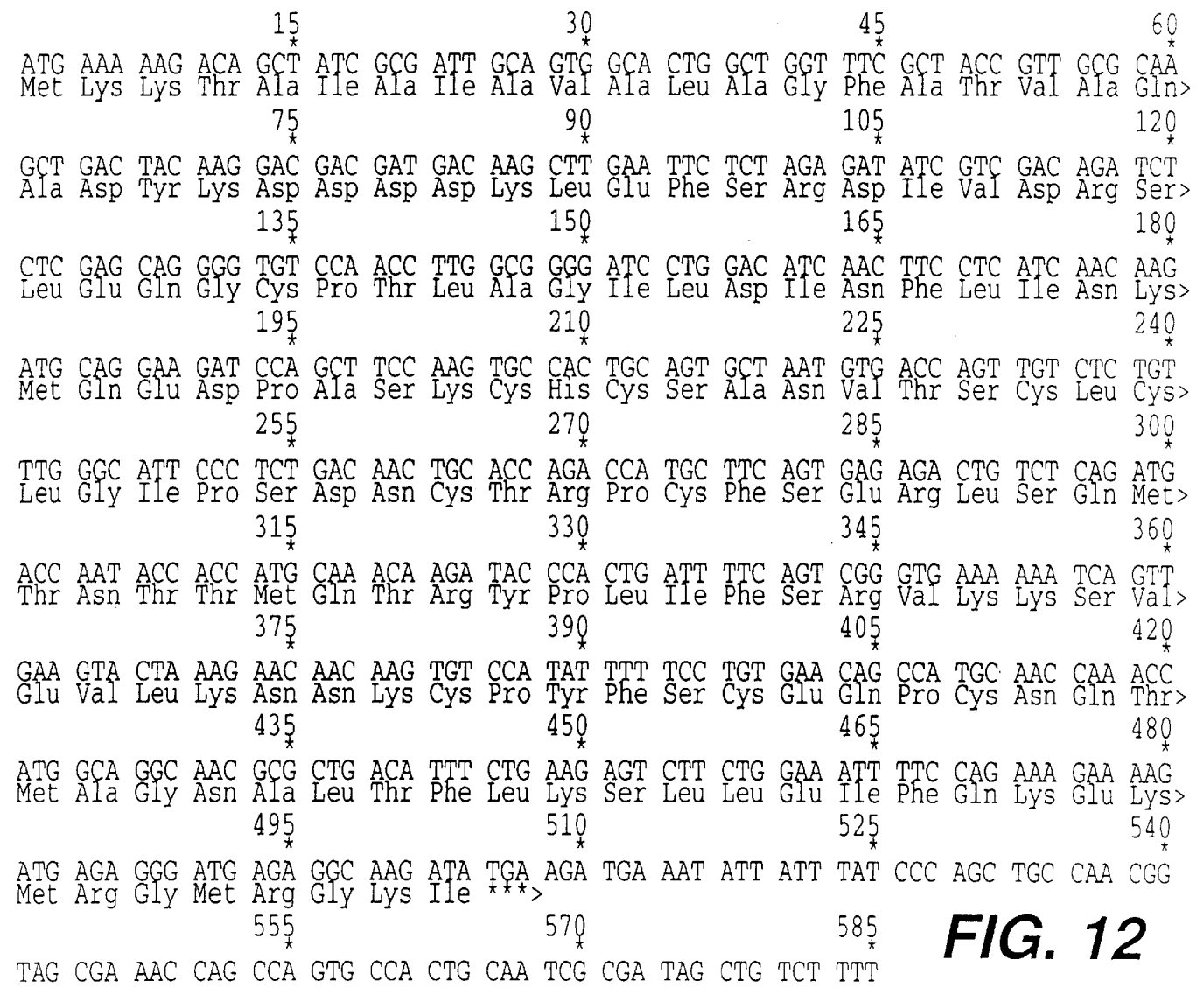

FIG. 12: Sequence of pFlag expression construct for the Met117 version of the cDNA from the region surrounding the site of ligation.

FIG. 14: Amino acid sequences for inhibitory peptides.

FIG. 26: An appendix of chemical moieties.

FIG. 27: Aminosterols isolated from the dog fish shark.

DETAILED DESCRIPTION OF THE INVENTION

Figure 1:
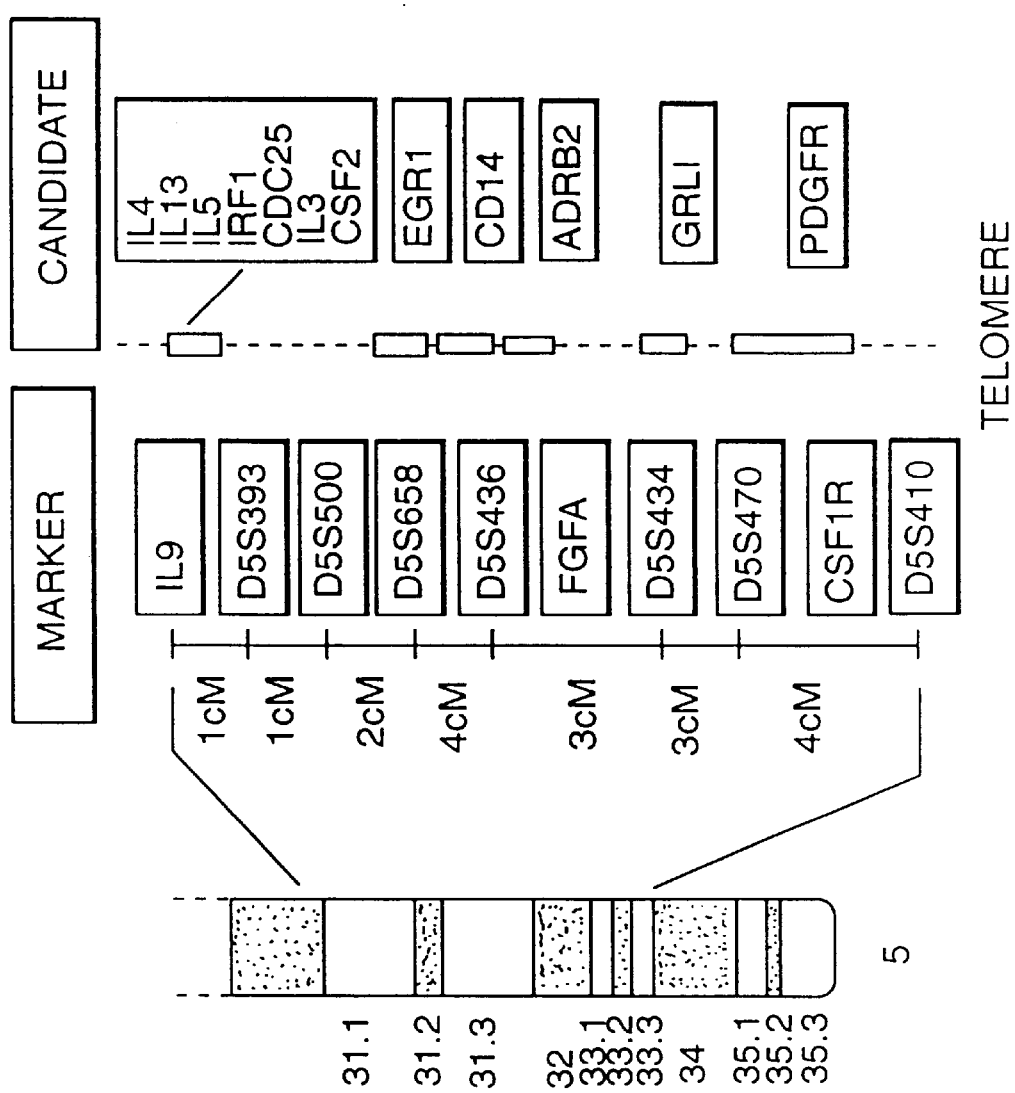
FIG. 1: Map showing the relative order and distance in centiMorgans [cM] between the polymorphic genetic markers useful for mapping asthma-related genes.

Applicant has resolved the needs in the art by elucidating an IL-9 pathway and compositions that affect that pathway that may be used in the diagnosis, prevention or treatment of atopic allergy including asthma and related disorders. Asthma encompasses inflammatory disorders of the airways with reversible airflow obstruction. Atopic allergy refers to atopy, and related disorders including asthma, bronchial hyperresponsiveness (BHR), rhinitis, urticaria, allergic inflammatory disorders of the bowel, and various forms of eczema. Atopy is a hypersensitivity to environmental allergens expressed as the elevation of serum total IgE or abnormal skin test responses to allergens as compared to controls. BHR refers to bronchial hyperresponsiveness, a heightened bronchoconstrictor response to a variety of stimuli.

By analyzing the DNA of families that exhibit asthma-related disorders, applicant has identified a polymorphism in the IL-9 gene that correlates with the biologic variability of serum total IgE as one measurable expression of atopy. The IL-9 gene (also known as Asthma Associated Factor 1 or AAF1) refers to the genetic locus of interleukin-9, a cytokine exhibiting a variety of functions involving the regulation of human myeloid and lymphoid systems. The IL-9 gene of the present invention is found in the q31-q33 region of human chromosome 5 and chromosome 13 in the mouse.

By polymorphism, applicant means a change in a specific DNA sequence, termed a "locus", from the prevailing sequence. In general, a locus is defined as polymorphic when artisans have identified two or more alleles encompassing that locus and the least common allele exists at a frequency of 1% or more.

The polymorphism of the present invention leads to an amino acid substitution at residue 117 of IL-9. Specifically, instead of the hydrophilic amino acid threonine, the IL-9 of the present invention exhibits the hydrophobic amino acid methionine (Met IL-9). On a genetic level, the polymorphism of the present invention is a substitution of a thymine residue for a cytosine residue at nucleotide position 3365 in the human IL-9 gene as it is described by Renauld and colleagues(1990) [GenBank accession numbers M30135 and M30136],[54] or at the comparable nucleotide position 4244 of the human IL-9 gene sequence reported by Kelleher et al.,(1991) [GenBank accession number M86593].[55]

Individuals with a threonine (Thr) at amino acid 117 of IL-9 in either one or both of their alleles (Thr/Thr or Thr/Met) generally exhibit susceptibility to an asthmatic or atopic allergic phenotype, and these genotypes are characterized by higher mean serum total IgE levels in the populations studied. In contrast, those individuals with a methionine (Met) at codon 117 of IL-9 in both alleles (Met/Met) exhibit a lack of asthma, fewer abnormal skin test responses, and a lower serum total IgE. Thus, the Met/Met genotype of IL-9 appears to protect against asthma or atopic allergy.

Accordingly, the invention provides a purified and isolated DNA molecule comprising a nucleotide sequence encoding human interleukin 9 containing methionine at position 117 (Met IL-9), or a fragment thereof. The invention also includes degenerate sequences of the DNA as well as sequences that are substantially homologous. The source of the IL-9 of the invention is human. Alternatively, the DNA or fragment thereof may be synthesized using methods known in the art. It is also possible to produce the compound by genetic engineering techniques, by constructing DNA by any accepted technique, cloning the DNA in an expression vehicle and transfecting the vehicle into a cell which will express the compound. See, for example, the methods set forth in Sambrook et al., *MOLECULAR CLONING: A LABORATORY MANUAL*, 2d ed. Cold Spring Harbor Laboratory Press [1985].

Airway hyperresponsiveness is found in virtually all asthmatics and in some strains of inbred mice (DBA/2).[84] Airway hyperresponsiveness is a risk factor for the development of asthma in humans and is used in animal models of asthma as a physiologic measure to assess the efficacy of treatment for asthma. These data along with human[79] and murine genetic mapping results (see Examples 1 and 2) suggest a critical role for the murine IL-9 gene product in the airway response of the mouse. In particular, the hyperresponsive DBA/2(D2) mice differ from the C57BL/6(B6) hyporesponsive mice[84] in their expression of steady state levels of IL-9 (See Example 14, FIG. 26). Furthermore, pretreatment with blocking antibodies to IL-9/IL-9 receptor can optionally provide complete protection from antigen induced airway hyperresponsiveness and inflammation in mice demonstrating a critical regulatory role for IL-9 in these immune responses. Thus, these data demonstrate that although different molecular changes produce biologic variability in airway responsiveness in humans and mice, these changes arise in the same gene(s) (IL-9/IL-9R) that regulate this pathway. Taken together, these observations confirm the critical role of IL-9 and the IL-9 receptor in airway hyperresponsiveness, asthma, and atopic allergy. Moreover, these data demonstrate that agents of the convention, which block the interaction of IL-9 with its receptor, protect against an antigen induced response such as those detailed above.

Further evidence defining the critical role of IL-9 in the pathogenesis of atopic allergy, bronchial hyperresponsivenss, asthma, and related disorders derives directly from the applicants observation that IL-9 is critical to a number of antigen induced responses in mice. When the functions of IL-9 are down regulated by antibody pretreatment prior to aerosol challenge with antigen, the animals can be completely protected from the antigen induced responses. These responses include: bronchial hyperresponsiveness, eosinophilia and elevated cell counts in bronchial lavage, histologic changes in lung associated with inflammation, and elevated serum total IgE. Thus, the treatment of such responses, which are critical to the pathogenesis of atopic allergy and which characterize the allergic inflammation associated with asthma, by the down regulation of the functions of IL-9, are within the scope of this invention.

Applicant also teaches the regulation of the activity of IL-9 by administering "agonists and antagonists" to the IL-9 receptor. The skilled artisan will readily recognize that all molecules containing the requisite 3-dimensional structural conformation and which contain the residues essential or critical for receptor binding are within the scope of this invention. Applicant has shown that peptides KP-16 (IL-9 residues 43–60) and KP-20 (IL-9 residues 71–90) (produced using standard peptide automated synthesis techniques, for example, the Applied Biosystems Model 431A Peptide Synthesizer) act as IL-9 antagonists. Specifically, applicant demonstrates that residues 43–60 and 71–90 of the mature protein appear to be important for receptor binding. In addition, these residues include most of exon 4 (amino acids 44–88) and are predicted to form anti-parallel helical structures. The three dimensional structure of the protein suggests that specifically serine 52 and/or glutamic acid 53 interact with lysine 85, serine 56 interacts with lysine 82, and threonine 59 interacts with valine 78. The three dimensional coordinates of these parallel helices and the related functional groups represent the requisite 3-dimensional conformation critical for receptor binding and compounds that simulate these relationships are within the scope of this invention.

The demonstration of an IL-9 sequence associated with an asthma-like phenotype, and one associated with the lack of an asthma-like phenotype, indicates that the lungs' inflammatory response to antigen is dependent on IL-9, and therefore, that down regulating the function of IL-9 should protect against the antigen induced response. Furthermore, applicant also provides methods of diagnosing susceptibility to atopic allergy and related disorders and for treating these disorders based on the relationship between IL-9 and its receptor.

A receptor is a soluble or membrane bound component that recognizes and binds to molecules, and the IL-9 receptor (also known as Asthma Associated Factor 2 or AAF2) of the invention is the component that recognizes and binds to IL-9. The functions of the IL-9 receptor consist of binding an IL-9-like molecule and propagating its regulatory signal in specific cells.[57-60] An interruption of that function will lead to a down regulation, i.e., reduction, of either the expression of IL-9 or of the functions controlled by IL-9. Accordingly, by virtue of this interaction between IL-9 and the IL-9 receptor, certain functions of the organism are modulated or controlled. For a general discussion of receptors, see Goodman and Gilman's *The Pharmacologic Basis of Therapeutics* (Seventh Edition, MacMillan Publishing Company, N.Y. USA, 1985).

One diagnostic embodiment involves the recognition of variations in the DNA sequence of IL-9. One method involves the introduction of a nucleic acid molecule (also known as a probe) having a sequence complementary to the IL-9 of the invention under sufficient hybridizing conditions, as would be understood by those in the art. In one embodiment, the sequence will bind specifically to the Met117 IL-9 or to Thr117 IL-9, and in another embodiment will bind to both Met117 IL-9 and Thr117 IL-9. Another method of recognizing DNA sequence variation associated with these disorders is direct DNA sequence analysis by multiple methods well known in the art.[77] Another embodiment involves the detection of DNA sequence variation in the IL-9 gene associated with these disorders.[73-77] These include the polymerase chain reaction, restriction fragment length polymorphism (RFLP) analysis and single stranded conformational analysis. In a preferred embodiment, applicant provides specifically for a method to recognize, on a genetic level, the polymorphism in IL-9 associated with the Thr and Met alleles using a StyI RFLP as described herein. In other embodiments Nla, Pfim1, PflM1, and Nco1 RFLPs may be used to distinguish these two alleles of IL-9 genes.

Another embodiment involves treatment of atopic allergy and related disorders. In a preferred embodiment, the applicant provides a method of administering a compound having activity comparable to Met IL-9 and the ability to bind to an IL-9 receptor in an amount sufficient to down regulate the activity of IL-9. A compound having activity comparable to Met IL-9 is a compound that functions similarly but not necessarily identically. Thus, it may bind to the IL-9 receptor but without the same physiological effects. Examples include amino acid sequences of IL-9 containing various point mutations and/or deletions and sequences substantially homologous thereto. For example, such a compound may interrupt the binding of Thr IL-9 to the IL-9 receptor as measured by techniques known in the art. The invention also encompasses functionally effective fragments of the above amino acid sequences. In one such technique, the Thr IL-9 may be considered a "ligand" for the IL-9 receptor, and binding between the two may be assessed by ligand-binding assays which are well known in the art as set forth in *Goodman and Gilman's The Pharmacologic Basis of Therapeutics* (Seventh Edition, MacMillan Publishing Company, N.Y. USA, 1985).

In another embodiment, the compound may resemble the Met allele of IL-9 in structure. Thus, such a compound may incorporate a methionine in codon 117 of IL-9 or may incorporate another hydrophobic amino acid. Thus, included within the scope of this invention are IL-9 variants comprising substitutions of Thr at position 117 by amino acids selected from the group consisting of alanine, valine, leucine, isoleucine, proline, phenylalanine, tryptophan, and methionine. Alternatively, the compound of the invention may exist as a fragment of IL-9 with a structural composition similar to Met IL-9. In another embodiment of the invention, the compound may retain functions comparable to Met IL-9, but may not resemble Met IL-9 in structure. For example, the composition of the compound may include molecules other than amino acids. This example is merely illustrative and one of ordinary skill in the art would readily recognize that other substitutions and/or deletion analogs of IL-9 resulting in effective antagonists are also within the scope of this invention. As discussed above all molecules containing the requisite 3-dimensional structural conformation and which contain the residues essential or critical for receptor binding are within the scope of this invention.

Specific assays may be based on IL-9's known regulation, in part, of the proliferation of T lymphocytes, IgE synthesis, and release from mast cells.[54-60] Another assay involves the ability of human IL-9 to specifically induce the rapid and transient tyrosine phosphorylation of multiple proteins in MO7e cells.[57] Because this response is dependent on the expression and activation of the IL-9 receptor, it represents a simple method or assay for the characterization of potentially valuable compounds. The tyrosine phosphorylation of Stat3 transcriptional factor appears to be specifically related to the actions of IL-9,[58] and this response represents a simple method or assay for the characterization of compounds within the invention. Still another method to characterize the function of IL-9 and IL-9-like molecules involves the well known murine TS1 clone and the D10 clone available from ATCC used to assess human IL-9 function with a cellular proliferation assay.[59] The Met IL-9 that forms a part of the invention may be viewed as a "weak agonist" of the IL-9 receptor. Such weak agonists are another preferred embodiment of the invention. The term agonist, according to this invention, includes compounds that mimic at least some of the effects of endogenous compounds by interacting or binding with a receptor. Agonists that interact or bind to the IL-9 receptor on the surface of certain cells initiate a series of biochemical and physiological changes that are characteristic of this cytokine's actions.[45-51,54-60] To identify other weak agonists of the invention, one may test for binding to the IL-9 receptor or for IL-9-like functions as described herein and in the cited literature.[2,45-51,54-60]

The present invention also includes antagonists of IL-9 and its receptor. Antagonists are compounds that are themselves devoid of pharmacological activity but cause effects by preventing the action of an agonist. To identify an antagonist of the invention, one may test for competitive binding with a known agonist or for down-regulation of IL-9-like functions as described herein and in the cited literature.[2,45-51,54-60]

The binding of either the agonist or antagonist may involve all known types of interactions including ionic forces, hydrogen bonding, hydrophobic interactions, van der Waals forces, and covalent bonds. In many cases, bonds of multiple types are important in the interaction of an agonist or antagonist with a receptor.

In a further embodiment, these compounds may be analogs of IL-9. IL-9 analogs may be produced by point mutations in the isolated DNA sequence for the gene, nucleotide substitutions, and/or deletions which can be created by methods that are all well described in the art.[62] This invention also includes spliced variants of IL-9 and discloses isolated nucleic acid sequences of interleukin-9, which contain deletions of one or more of its five exons. The term "spliced variants" as used herein denotes a purified and isolated DNA molecule encoding human IL-9 comprising at least one exon. There is no evidence of naturally expressed spliced mutants in the art. Thus, the present invention provides an isolated nucleic acid containing exons 1, 4 and 5 of human IL-9. Other variants within the scope of this invention include sequences comprising exons 1, 2, 3, 4, and 5; exons 1, 2, 3, and 4; exons 1, 2, 4, and 5 and exons 1, 3, 4, and 5. It must be understood that these exons may contain various point mutations.

Specific examples of antagonistic peptides derived from IL-9 include KP-16 (SEQ. ID No. 13) and KP-20 (SEQ. ID NO. 14) which are derived from exon 4. Exon 4 encodes 44 amino acids while the peptides mentioned above contain 16 and 20 amino acids respectively and they do not overlap. These peptides exhibit considerable inhibitory activity both individually and when assayed in combination. Additionally, KP-23 (SEQ ID NO. 15) and KP-24 (SEQ ID NO 16) are derived from exon 5 and also exhibit similar activity. Splice variants of IL-9 can be formed by deletion of any one or more of the IL-9 exons 1 through 5. As shown above, peptides derived from these exons show regulatory capability and, accordingly, are useful in treating atopic allergies, including asthma.

It is known in the art that, in multienzyme systems, the first or regulatory enzyme can be activated or inhibited by the end product of the multi-enzyme system. When the concentration of the end product increases over the steady state concentration, the end product will act as a specific activator or inhibitor of the regulatory enzyme in the sequence. Such feedback mechanism is also relevant to the IL-9 system and it is observed that the various polypeptides of this invention are capable of exerting such activation or inhibitory control on the activity of the IL-9 receptor and possibly the expression or function of other cytokines and their receptors that play a role in the pathogenesis of asthma.

The invention also includes modifications of agonists or antagonists that can be made using knowledge that is routine to those in this art. For example, the affinity of a compound for a receptor is generally closely related to the chemical structure of the compound. Thus, structure-activity relationships may be used to modify the agonists and antagonists of the invention. For example, the techniques of crystallography/X-ray diffraction and NMR may be used to make modifications of the invention.

For example, one can create a three dimensional structure of human IL-9 that can be used as a template for building structural models of deletion mutants using molecular graphics. These models can then be used to identify and construct a mutant IL-9 molecule with affinity for the IL-9 receptor comparable to IL-9, but with a lower biologic activity. What is meant by lower biologic activity is 2 to 100,000 fold less than IL-9, preferably 100 to 1,000 fold less than IL-9.

In still another embodiment, these compounds also may be used as dynamic probes for receptor structure and to develop receptor antagonists using IL-9 dependent cell lines.

In addition, this invention also provides compounds that prevent the synthesis or reduce the biologic stability of IL-9 or the IL-9 receptor. Biologic stability is a measure of the time between the synthesis of the molecule and its degradation. For example, the stability of a protein, peptide or peptide mimetic[89] therapeutic may be prolonged by using D-amino acids, or shortened by altering its sequence to make it more susceptible to enzymatic degradation.

In another embodiment, the agonists and antagonists of the invention are antibodies to IL-9 and the IL-9 receptor. The antibodies to IL-9 and its receptor may be either monoclonal or polyclonal made using standard tecnniques well known in the art (See Harlow & Lane's *Antibodies—A Laboratory Manual* (Cold Spring Harbor Laboratory, 1988). They can be used to block IL-9 from binding to the receptor. In one embodiment the antibodies interact with IL-9. In another embodiment the antibodies interact with the IL-9 receptor. The IL-9 used to elicit these antibodies can be any of the IL-9 varients discussed above.

Antibodies are also produced from peptide sequences of IL-9 or the IL-9 receptor using standard techniques in the art (see Protocols in Immunology, Chapt. 9, Wiley). The peptide sequences from the murine IL-9 receptor that can be used to produce blocking antisera have been identified as: GGQKA-GAFTC (residues 1–10)(SEQ ID NO:19); LSNSIYRIDCH-WSAPELGQESR (residues 11–32)(SEQ ID NO:20); and CESYEDKTEGEYYKSHWSEWS (residues 184–203 with a Cys residue added to the N-terminus for coupling the peptide to the carrier protein) (SEQ ID NO:21). In addition. an epitope that binds to a blocking antibody directed to the human IL-9 receptor has been identified as residues 8–14 of the mature human IL-9 receptor. (TCLTNNI)(SEQ ID NO:22) and two epitopes that bind to blocking antibodies directed to human IL-9 have also been identified as residues 50–67 (CFSERLSQMTNTTMQTRY) (SEQ ID NO:23) and residues 99–116 (TAGNALTFLKSLLEIFQK) (SEQ ID NO:16) The human epitopes as well as the human peptides that correspond to the peptides that produce blocking antibodies in the murine sequences are most likely to be useful for the production of therapeutic antibodies.

In still another embodiment, the compounds of the invention may be coupled to chemical moieties, including proteins that alter the functions or regulation of the IL-9 pathway for therapeutic benefit in atopic allergy and asthma.[61] These proteins may include in combination other cytokines and growth factors including[67] L-4, IL-5, IL-3, IL-2, IL-13, and IL-10 that may offer additional therapeutic benefit in atopic allergy and asthma. In addition, the IL-9 of the invention may also be conjugated through phosphorylation and conjugated to biotinylate, thioate, acetylate, iodinate, and any of the crosslinking reagents shown in FIG. 27 (Pierce).

In a further embodiment, the invention includes the down regulation of IL-9 expression or function by administering soluble IL-9 receptor molecules that bind IL-9. Renauld et al.[59] have shown the existence of a soluble form of the IL-9 receptor. This molecule can be used to prevent the binding of IL-9 to cell bound receptor and act as an antagonist of IL-9. Soluble receptors have been used to bind cytokines or other ligands to regulate their function.[87] A soluble receptor is a form of a membrane bound receptor that occurs in solution, or outside of the membrane. Soluble receptors may occur because the segment of the molecule which commonly associates with the membrane is absent. This segment is commonly referred to in the art as the transmembrane domain of the gene, or membrane binding segment of the protein. Thus, in one embodiment of the invention, a soluble receptor may represent a fragment or an analog of a membrane bound receptor. In another embodiment of the invention, the structure of the segment that associates with the membrane may be modified (e.g. DNA sequence polymorphism or mutation in the gene) so the receptor is not inserted into the membrane, or the receptor is inserted, but is not retained within the membrane. Thus, a soluble receptor, in contrast to the corresponding membrane bound form, differs in one or more segments of the gene or receptor protein that are important to its association with the membrane.[52,53]

These compounds may be known forms of a soluble IL-9 receptor that act to bind IL-9. Alternatively, these compounds may resemble known forms of the IL-9 receptor, but may exist as fragments. In another embodiment of the invention, the compound may retain functions comparable to soluble IL-9 receptor, but may not resemble soluble IL-9 receptor in composition. For example, the composition of the compound may include molecules other than amino acids. Thus, these compounds will bind IL-9 and prevent IL-9 from acting at its cell surface receptor.

A further embodiment of the invention relates to antisense or gene therapy. It is now known in the art that altered DNA molecules can be tailored to provide a specific selected effect, when provided as antisense or gene therapy. The native DNA segment coding for IL-9 receptor, has, as do all other mammalian DNA strands, two strands; a sense strand and an antisense strand held together by hydrogen bonding. The mRNA coding for the receptor has a nucleotide sequence identical to the sense strand, with the expected substitution of thymidine by uridine. Thus, based upon the knowledge of the receptor sequence, synthetic oligonucleotides can be synthesized. These oligonucleotides can bind to the DNA and RNA coding for the receptor. The active fragments of the invention, which are complementary to MRNA and the coding strand of DNA, are usually at least about 15 nucleotides, more usually at least 20 nucleotides, preferably 30 nucleotides and more preferably may be 50 nucleotides or more. The binding strength between the sense and antisense strands is dependent upon the total hydrogen bonds. Therefore, based upon the total number of bases in the MRNA, the optimal length of the oligonucleotide sequence may be easily calculated by the skilled artisan.

The sequence may be complementary to any portion of the sequence of the mRNA, i.e., it may be proximal to the 5'-terminus or capping site, or downstream from the capping site, between the capping site and the initiation codon and may cover all or only a portion of the non-coding region or the coding region. The particular site(s) to which the antisense sequence binds will vary depending upon the degree of inhibition desired, the uniqueness of the sequence, the stability of the antisense sequence, etc.

In the practice of the invention, expression of the IL-9 receptor is down-regulated by administering an effective amount of synthetic antisense oligonucleotide sequences described above. The oligonucleotide compounds of the invention bind to the MRNA coding for human IL-9 or IL-9 receptors thereby inhibiting expression (translation) of these proteins. See Gruss et al., "Interleukin 9 is expressed by primary and cultural Hodgkin and Reed-Sternberg cells." Cancer Res. 52:1026–31 (Feb. 15, 1992)

The isolated DNA sequences containing various mutations such as point mutations, insertions, deletions, or spliced mutations of IL-9 are useful in gene therapy as well.

In addition to the direct regulation of the IL-9 receptor, this invention also encompasses methods of downstream regulation which involve inhibition of signal transduction. In particular, a further embodiment of this invention is drawn to inhibition of tyrosine phosphorylation. It is known in the art that highly exergonic phosphoryl-transfer reactions are catalyzed by various enzymes known as kinases. In other words, a kinase transfers phosphoryl groups between ATP and a metabolite. IL-9 induces tyrosine phosphorylation of multiple proteins; it is known in the art that in addition to the activation of JAK1 and JAK3 tyrosine kinases, IL-9 also induces tyrosine phosphorylation of Stat3.[58] Phoshorylation of Stat3 is unique to the IL-9 signal transduction pathway and hence is a perfect target for inhibitors.[58] This invention includes within its scope tyrphostins which are specific inhibitors of protein tyrosine kinases. Thus, tyrphostins (obtained for example from Calbiochem) and other similar inhibitors of these kinases are useful in the modulation of signal transduction and are useful in the treatment of atopic allergies and asthma.

In still another aspect of the invention, it was surprisingly, found that aminosterol compounds are also useful in the inhibition of signal transduction due to IL-9 stimulation. Aminosterol compounds which are useful in this invention are described in U.S. patent application, Ser. No. 08/290,826 and its related applications 08/416,883 and 08/478,763 as well as in 08/483,059 and its related application 08/483,057, 08/479,45S, 08/479,457, 08/475,572, 08/476,855, 08/474,799 and 08/487,443, which are specifically incorporated herein by reference.

In addition, the invention includes pharmaceutical compositions comprising the compounds of the invention together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectionable solutions. Suitable pharmaceutical carriers are described in Martin, E. W., *Remington's Pharmaceutical Sciences*, specifically incorporated herein by reference.

The compounds used in the method of treatment of this invention may be administered systemically or topically, depending on such considerations as the condition to be treated, need for site-specific treatment, quantity of drug to be administered, and similar considerations.

Topical administration may be used. Any common topical formation such as a solution, suspension, gel, ointment, or salve and the like may be employed. Preparation of such topical formulations as are well described in the art of pharmaceutical formulations as exemplified, for example, by *Remington's Pharmaceutical Science*, Edition 17, Mack Publishing Company, Easton, Pa. For topical application, these compounds could also be administered as a powder or spray, particularly in aerosol form. The active ingredient may be administered in pharmaceutical compositions adapted for systemic administration. As is known, if a drug is to be a administered systemically, it may be confected as a powder, pill, tablets or the like, or as a syrup or elixir for oral administration. For intravenous, intraperitoneal or intralesional administration, the compound will be prepared as a solution or suspension capable of being administered by injection. In certain cases, it may be useful to formulate these compounds in suppository form or as an extended release formulation for deposit under the skin or intermuscular injection. In a preferred embodiment, the compounds of this invention be administered by inhalation. For inhalation therapy the compound may be in a solution useful for administration by metered dose inhalers, or in a form suitable for a dry powder inhaler.

An effective amount is that amount which will down regulate either the expression of IL-9 or the functions controlled by IL-9. A given effective amount will vary from condition to condition and in certain instances may vary with the severity of the condition being treated and the patient's susceptibility to treatment. Accordingly, a given effective amount will be best determined at the time and place through routine experimentation. However, it is anticipated that in the treatment of asthma-related disorders in accordance with the present invention, a formulation containing between 0.001 and 5 percent by weight, preferably about 0.01 to 1%, will usually constitute a therapeutically effective amount. when administered systemically, an amount between 0.01 and 100 mg per kg body weight per day, but preferably about 0.1 to 10 mg/kg, will effect a therapeutic result in most instances.

Applicant also provides for a method to screen for the compounds that down regulate the expression of IL-9 or the functions controlled by IL-9. One may determine whether the functions expressed by IL-9 are down-regulated using techniques standard in the art.[57-60] In a specific embodiment, applicant provides for a method of identifying compounds with functions comparable to Met IL-9. Thus, in one embodiment, serum total IgE may be measured using techniques well known in the art[42] to assess the efficacy of a compound in down regulating the functions of IL-9 in vivo.

In another embodiment, bronchial hyperresponsiveness, bronchoalveolar lavage, and eosinophilia may be measured using techniques well known in the art[42] to assess the efficacy of a compound in down regulating the functions of IL-9 in vivo. In yet another embodiment, the functions of IL-9 may be assessed in vitro. As is known to those in the art, human IL-9 specifically induces the rapid and transient tyrosine phosphorylation of multiple proteins in MO7e cells. The tyrosine phosphorylation of Stat3 transcriptional factor appears to be specifically related to the actions of IL-9. Another method to characterize the function of IL-9 and IL-9-like molecules that depends on the "stable expression" of the IL-9 receptor uses the well known murine TS1 clones to assess human IL-9 function with a cellular proliferation assay.[59]

The invention also includes a simple screening assay for saturable and specific ligand binding based on cell lines that express the IL-9 receptor.[46,59] The IL-9 receptor is expressed in on a wide variety of cell types, including K562, C8166-45, B cells, T cells, mast cells, neutrophils, megakaryocytes (UT-7 cells),[53] the human megakaryoblastic leukemia cell lines MO7e[57], TF1,[59] macrophages, fetal thymocytes, the human kidney cell line 293,[53] and murine embryonic hippocampal progenitor cell lines.[46,52,53] In another embodiment, soluble IL-9 receptor may be used to evaluate ligand binding and potential receptor antagonists.

The practice of the present invention will employ the conventional terms and techniques of molecular biology, pharmacology, immunology, and biochemistry that are within the ordinary skill of those in the art. See, for example, Sambrook et al., *MOLECULAR CLONING: A LABORATORY MANUAL*, 2d ed. Cold Spring Harbor Laboratory Press [1985], or Ausubel et al., *CURRENT PROTOCOLS IN MOLECULAR BIOLOGY*, John Wiley & Sons, Inc. [1994].

Nonetheless, we offer the following basic background information. The body's genetic material, or DNA, is arranged on 46 chromosomes, which each comprises two arms joined by a centromere. Each chromosome is divided into segments designated p or q. The symbol p is used to identify the short arm of a chromosome, as measured from the centromere to the nearest telomere. The long arm of a chromosome is designated by the symbol q. Location on a chromosome is provided by the chromosome's number (i.e., chromosome 5) as well as the coordinates of the p or q region (i.e., q31-q33). In addition, the body bears the sex chromosomes, X and Y. During meiosis, the X and Y chromosomes exchange DNA sequence information in areas known as the pseudoautosomal regions.

DNA, deoxyribonucleic acid, consists of two complementary strands of nucleotides, which include the four different base compounds, adenine [A], thymine [T], cytosine [C], and guanine [G]. A of one strand bonds with T of the other strand while C of one strand bonds to G of the other to form complementary "base pairs," each pair having one base in each strand.

A sequential grouping of three nucleotides [a "codon"] codes for one amino acid. Thus, for example, the three nucleotides CAG codes for the amino acid Glutamine. The 20 naturally occurring amino acids, and their one letter codes, are as follows:

| | | |
|---|---|---|
| Alanine | Ala | A |
| Arginine | Arg | R |

| | | |
|---|---|---|
| Asparagine | Asn | N |
| Aspartic Acid | Asp | D |
| Asparagine or Aspartic acid | Asx | B |
| Cysteine | Cys | C |
| Glutamine | Gln | Q |
| Glutamine Acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acids comprise proteins. Amino acids may be hydrophilic, i.e., displaying an affinity for water, or hydrophobic, i.e., having an aversion to water. Thus, the amino acids designated as G, A, V, L, I, P, F, Y, W, C and M are hydrophobic and the amino acids designated as S, Q, K, R, H, D, E, N and T are hydrophilic. In general, the hydrophilic or hydrophobic nature of amino acids affects the folding of a peptide chain, and consequently the three dimensional structure of a protein.

DNA is related to protein as follows:

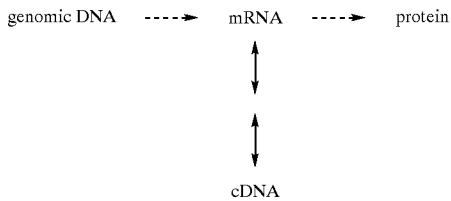

Genomic DNA comprises all the DNA sequences found in an organism's cell. It is "transcribed" into messenger RNA ["mRNA"]. Complementary DNA ["cDNA"] is a complementary copy of mRNA made by reverse transcription of mRNA. Unlike genomic DNA, both mRNA and cDNA contain only the protein-encoding or polypeptide-encoding regions of the DNA, the so-called "exons." Genomic DNA may also include "introns," which do not encode proteins.

In fact, eukaryotic genes are discontinuous with proteins encoded by them, consisting of exons interrupted by introns. After transcription into RNA, the introns are removed by splicing to generate the mature messenger RNA (mRNA). The splice points between exons are typically determined by consensus sequences that act as signals for the splicing process. Splicing consists of a deletion of the intron from the primary RNA transcript and a joining or fusion of the ends of the remaining RNA on either side of the excised intron. Presence or absence of introns, the composition of introns, and number of introns per gene, may vary among strains of the same species, and among species having the same basic functional gene. Although in most cases, introns are assumed to be nonessential and benign, their categorization is not absolute. For example, an intron of one gene can represent an exon of another. In some cases, alternate or different patterns of splicing can generate different proteins from the same single stretch of DNA. In fact, structural features of introns and the underlying splicing mechanisms form the basis for classification of different kinds of introns.

As to the exons, these can correspond to discrete domains or motifs, as for example, functional domains, folding regions, or structural elements of a protein; or to short polypeptide sequences, such as reverse turns, loops, glycosylation signals and other signal sequences, or unstructured polypeptide linker regions. The exon modules of the present combinatorial method can comprise nucleic acid sequences corresponding to naturally occurring exon sequences or naturally occurring exon sequences which have been mutated (e.g. point mutations, truncations, fusions).

Returning now to the manipulation of DNA, DNA can be cut, spliced, and otherwise manipulated using "restriction enzymes" that cut DNA at certain known sites and DNA ligases that join DNA. Such techniques are well known to those of ordinary skill in the art, as set forth in texts such as Sambrook, et al., *MOLECULAR CLONING: A LABORATORY MANUAL*, 2d ed. Cold Spring Harbor Laboratory Press [1985] or Ausubel et al., *CURRENT PROTOCOLS IN MOLECULAR BIOLOGY*, John Wiley & Sons, Inc. [1994].

DNA of a specific size and sequence can then be inserted into a "replicon," which is any genetic element, such as a plasmid, cosmid, or virus, that is capable of replication under its own control. A "recombinant vector" or "expression vector" is a replicon into which a DNA segment is inserted so as to allow for expression of the DNA, i.e., production of the protein encoded by the DNA. Expression vectors may be constructed in the laboratory, obtained from other laboratories, or purchased from commercial sources.

The recombinant vector [known by various terms in the art] may be introduced into a host by a process generically known as "transformation." Transformation means the transfer of an exogenous DNA segment by any of a number of methods, including infection, direct uptake, transduction, F-mating, microinjection, or electroporation into a host cell.

Unicellular host cells, known variously as recombinant host cells, cells, and cell culture, includebacteria, yeast, insect cells, plant cells, mammalian cells and human cells. In particularly preferred embodiments, the host cells include *E.coli*, Pseudonas, Bacillis, Streptomyces, Yeast, CHO, R1-1, B-W, LH, COS-J, COS-7, BSC1, BSC40, BMT10, and S69 cells. Yeast cells especially include Saccharomyces, Pichia, Candida, Hansenula, and Torulopis.

As those skilled in the art recognize, the expression of the DNA segment by the host cell requires the appropriate regulatory sequences or elements. The regulatory sequences vary according to the host cell employed, but include, for example, in prokaryotes, a promoter, ribosomal binding site, and/or a transcription termination site. In eukaryotes, such regulatory sequences include a promoter and/or a transcription termination site. As those in the art well recognized, expression of the polypeptide may be enhanced, i.e., increased over the standard levels, by careful selection and placement of these regulatory sequences.

In other embodiments, promoters that may be used include the human cytomegalovierus (CMV) promoter, tetracycline inducible promoter, simian virus (SV40) promoter, moloney murine leukemia long terminal repeat (LTR) promoter, glucocorticoid inducible murine mammary tumor virus (MMTV) promoter, Herpes thymidine kinase promoter, murine and human β-actin promoters, HTLV1 and HIV IL-9 5' flanking region, human and mouse IL-9 receptor 5' flanking region, bacterial tac promoter and drosophila heat shock scaffold attachment region (SAR) enhancer elements.

The DNA may be expressed as a polypeptide of any length such as peptides, oligopeptides, and proteins.

Polypeptides also include translational modifications such as glycosylations, acetylations, phosphorylations, and the like.

Another molecular biologic technique of interest to the present invention is "linkage analysis." Linkage analysis is an analytic method used to identify the chromosome or chromosomal region that correlates with a trait or disorder.[44] Chromosomes are the basic units of inheritance on which genes are organized. In addition to genes, artisans have identified "DNA markers" on chromosomes. DNA markers are known sequences of DNA whose identity and sequence can be readily determined. Linkage analysis methodology has been applied to the mapping of disease genes, for example, genes relating to susceptibility to asthma, to specific chromosomes.[42,44]

Other embodiments of the invention will be apparent to those skilled in the art from consideration of the specification and practice of the invention disclosed. It is intended that the specifications and examples be considered exemplary only with a true scope of the invention being indicated by the claims.

METHODS

In conducting the experiments described in the Examples below, applicant used the following methods:

Patient Populations

Asthma families were recruited from two sources.[27,42,79-83,88] In each case patients were genotyped with respect to the polymorphism at position 3365 of the human IL-9 gene [GenBank accession number M30136].

A third population of 74 individuals was ascertained randomly with respect to asthma and atopy from the East Coast of the United States. The frequency of the Met substitution at codon 117 was used as an unbiased estimate of the prevalence of this variant in the general population.

A fourth population of 49 individuals was ascertained randomly with respect to asthma and atopy from the Philadelphia, Pennsylvania area. Total serum IgE were assayed by enzyme-linked immunosorbent test [ELISA, Genzyme, Cambridge, Mass.]. DNA was extracted from the WBC in peripheral blood from each individual. Analyses of genetic markers (genotyping) and candidate genes were performed on the genomic DNA extracted. Once again, the frequency of the Met substitution at codon 117 was used as an unbiased estimate of the prevalence of this variant in the general population.

Oligonucleotide Primers.

All primers were designed using OLIGO 4.0. Characterization of the IL-9 gene was carried out using primers surrounding each of the 5 exons of the reported sequence. The primer sequences surrounding each exon were: exon 1 [upper] [5' GCT CCA GTC CGC TGT CAA 3'] and [lower] [5' CTC CCC CTG CAG CCT ACC 3'][product size 150 bp]; exon 2 [upper] [5' CGG GGC TGA CTA AAG GTT CT 3'] and [lower] [5' GTT CTT AAA GAG CAT TCA CT 3'] [product size 99 bp]; exon 3 [upper] [5' ATT TTC ACA TCT GGA ATC TTC ACT 3'] and [lower][5' AAT CCA AGG TCA ACA TTA TG 3'][product size 113 bp]; exon 4 [upper] [5' TTT CTT TGA ATA AAT CCT TAC 3'] and [lower] [5' GAA ATC ACC AAC AGG AAC ATA 3'][product size 206 bp]; and exon 5 [upper] [5'ATC AAC TTT CAT CCC CAC AGT 3'] and [lower] [5'GGA TAA ATA ATA TTT CAT CTT CAT 3']. Each exon was examined first by a single strand conformational polymorphism assay [SSCP].[72,77] The primers for exon 5 produced a 160 bp product after polymerase chain reaction [PCR] amplification which was also examined by direct solid phase sequence analysis.[72,77] The upper primer was synthesized with a 5' biotin label and, following amplification, the PCR product was captured by a streptavidin-linked paramagnetic bead [Dynal] and characterized by Sanger sequencing as described elsewhere.[77] Sequence polymorphisms were distinguished from artifact by repeated analyses.

SSCP Analysis.

SSCP, a method for detection of polymorphisms on the basis of changes in migration of single-stranded DNA exposed to an electric field,[72] was carried out as set forth in Schwengel et al., (1994) at room temperature with and without 10% glycerol using 6% polyacrylamide gel electrophoresis at a cross-linking monomer concentration of 2.67%.[77] Four $\mu$l of PCR product was mixed with 5 $\mu$l 2× stop buffer [95% formamide, 20 mM EDTA, 0.05% BPB, 0.05% xylene cyanol], and 1 $\mu$l 0.5% SDS and 50 $\mu$M EDTA, denatured at 85–90° C. for 8 minutes, and then immediately placed on ice. Electrophoresis was carried out at 12 watts for approximately 24 hours for glycerol containing gels and 12 hours for non-glycerol gels. The gels were then dried and exposed to Kodak XAR® film.

DNA Sequencing.

Direct DNA sequencing of the PCR products was accomplished using solid phase techniques after verifying the presence of the correct size PCR product on a 1% agarose gel stained with ethidium bromide as set forth in Schwengel et al., 1994.[77] Twenty $\mu$l of PCR product was incubated with 40 $\mu$l of Dynabeads® m-280 [Dynal] for 15 minutes. The beads were washed and diluted as suggested by the manufacturer. Each sample was subsequently washed with B&W buffer containing 10 mM tris-HCl pH 7.5, 1 mM EDTA, 2 M NaCl, denatured with 0.1 N NaOH, and then washed with 0.1 N NaOH, B&W buffer, and 10 mM Tris-HCl pH 8 and 1 mM EDTA[TE]. The pellet of beads was resuspended with 10 $\mu$l of H2O.

Sanger sequencing reactions were carried out using Sequenase [United States Biochemical Co.]. $^{35}$S-dATP or $^{33}$P-dATP was incorporated into the sequencing reactions, and the products were electrophoresed through either 5% or 6% polyacrylamide gels containing 7 M urea. Gels were dried without fixing and exposed to X-ray film. Alleles were determined by comparing the genotypes of parents and offspring. Infrequent artifacts were easily distinguished from true sequence polymorphisms by repetition.

DNA was available and extracted from peripheral leukocytes. Genomic DNA was diluted to a concentration of 200 $\mu$g/ml for amplification.[27,42] Simple sequence repeats [SSR] including DXYS154 were selected from the Genome Data Base [GDB; Welch library, Johns Hopkins University, Baltimore, Md.]. Genotyping of the sKK-1 marker was carried out using the following primers sKK-1U [5' CAA ATC TGA AGA GCA AAC TAT 3'] and sKK-1L [5' TTA AAA AAT TCA TTT CAG TAT TCT 3'] which produce a 90 bp product. Each SSR product was amplified by PCR[72] and sized according to methods previously described.[27,42] Sample handling was carried out as described by Weber et al. with minor modifications.[71,27,42] Genotypes were determined from two independent readings of each autoradiograph. Individuals genotyping the families were blinded to the clinical data.

RFLP Analysis.

As a result of the C to T polymorphism at position 3365, a StyI restriction fragment length polymorphism [RFLP] was produced at position 52 of the IL-9 exon 5 PCR product. To test for the presence of this DNA sequence variant the lower primer from exon 5 was end-labeled prior to PCR amplification. The PCR product was then digested with StyI producing two fragments 108 bp [labeled] and 52 bp

[unlabeled] in length. This RFLP was used along with SSCP to confirm the presence of this polymorphism in families and individuals.

Linkage Analyses and Data Management.

Linkage analyses were performed using affected sib-pair methods [SIBPAL, S.A.G.E.],[78] an established approach for the investigation of the genetic basis of complex traits, such as BHR, atopy, and asthma. Affected sib-pairs are usually tested first, since a proportion of unaffected sib-pairs may still be gene carriers but do not express the trait. In contrast to LOD score methods where the model of inheritance [dominant, recessive, etc.] must be specified exactly, analysis by sib-pair methods makes no explicit assumptions in this regard. Thus, in sib-pair analyses the parents' clinical information is not used in testing for linkage. The pertinent observation in these methods is how often two affected offspring share copies of the same parental marker allele.[44] If the same copy of a parental marker allele is observed in different offspring, they are said to be inherited "identical by descent." Linkage is suggested when affected sib-pairs are identical by descent for a marker allele significantly more often than expected by chance [50%]. When the same marker allele is transmitted with the disease gene in different offspring, this implies that the marker locus is linked, or must be located close enough on the same chromosome, to the disease gene so they cosegregate during meiosis. The trait is then mapped by knowing the chromosomal localization of the marker.

Linkage in humans may also be established by the method of likelihood ratios. This method involves comparison of the probability that observed family data would arise under one hypothesis, for instance, linkage between two DNA markers, to the probability that it would arise under an alternative hypothesis, typically, nonlinkage. The ratio of these probabilities is called the odds ratio for one hypothesis relative to the other. By convention, mammalian geneticists prefer the log of the odds ration, or the LOD score. Generally, linkage is considered proved when the odds in favor of linkage versus nonlinkage become overwhelming, or reach 1,000:1 [LOD=3]. Linkage is rejected when the odds drop to 100:1 against this hypothesis [LOD=–2]. The maximum likelihood estimate is the recombination fraction where the likelihood ratio is largest. LODs from multiple pedigrees are thus added until the score grows to 3 [signifying 1,000:1 odds] or falls to –2 [indicating 100:1 odds].

All clinical and genotype data is managed using EXCELL® on a MacIntosh® or Sun Microsystems® computer. Statistical analyses were preformed using JMP [SAS Institute, Inc. Cary, N.C.]. The Wilcoxon/Kruskal-Wallis Tests [rank sums] was used to test whether individuals who were homozygous [Met/Met], heterozygous [Met/Thr], or homozygous [Thr/Thr] at codon 117 differ in their serum total IgE. All P-values are two-tailed except affected sib-pair analyses, where a one-tailed test was used because only an increased sharing of alleles was expected.

Having provided this background information, applicant now describes preferred aspects of the invention.

EXAMPLE 1

Linkage Analysis Between BHR and Murine Chromosome 13

As an aid in dissecting the complex genetic determinants of BHR, applicant has developed murine models that differ in their genetic susceptibility to various bronchoconstrictor stimuli. Inbred animal models using recombinant inbred strains [BXD] can facilitate ongoing studies in humans to determine the number of genes regulating susceptibility to BHR, the magnitude of their affect, and their precise chromosomal location. In particular, localizing in an animal model a gene determining susceptibility to a critical risk factor for asthma may aid in the positional cloning of this gene in humans.

Figure 2:
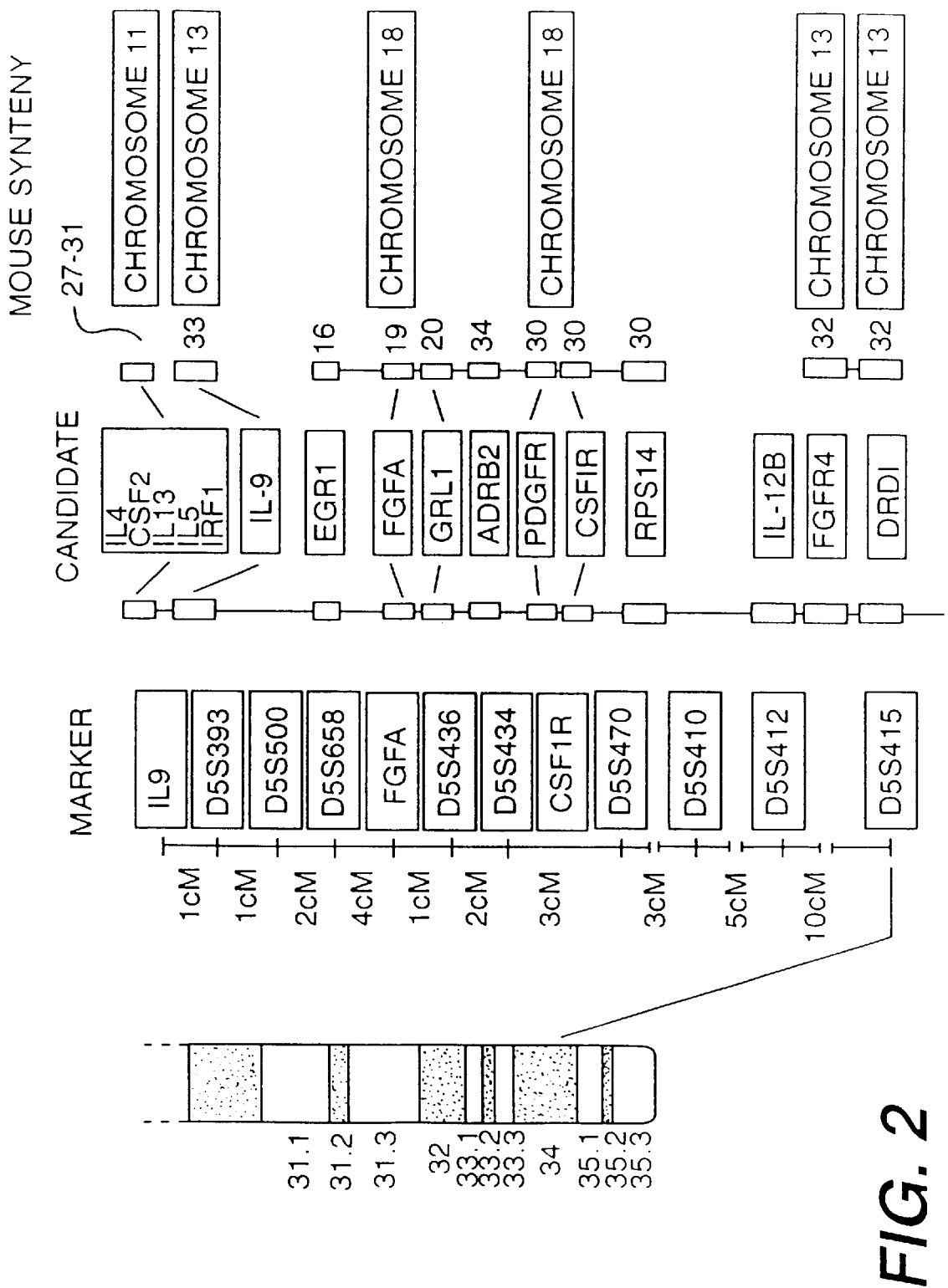
FIG. 2: Illustration of the genetic map of human chromosome 5q31-q33 and syntenic regions in the mouse.

Although the gene[s] predisposing to BHR and atopy had not yet been identified prior to this invention, chromosome 5q31-q33 was known to be syntenic with portions of mouse chromosomes 11, 13, and 18. FIG. 2 illustrates the syntenic regions containing numerous positional candidates that may potentially play a role in airway inflammation associated with BHR, atopy, and asthma. Specifically, the region of human chromosome 5q31-q33 demonstrating significant evidence for linkage with BHR is homologous to portions of mouse chromosomes 11, 13, and 18 which contain numerous candidate genes.[84]

In particular, IL-9 or a nearby gene have recently been suggested as likely candidates on the basis of linkage disequilibrium between log serum total IgE levels and a marker in this gene using a randomly ascertained population.[43]

Figure 3:
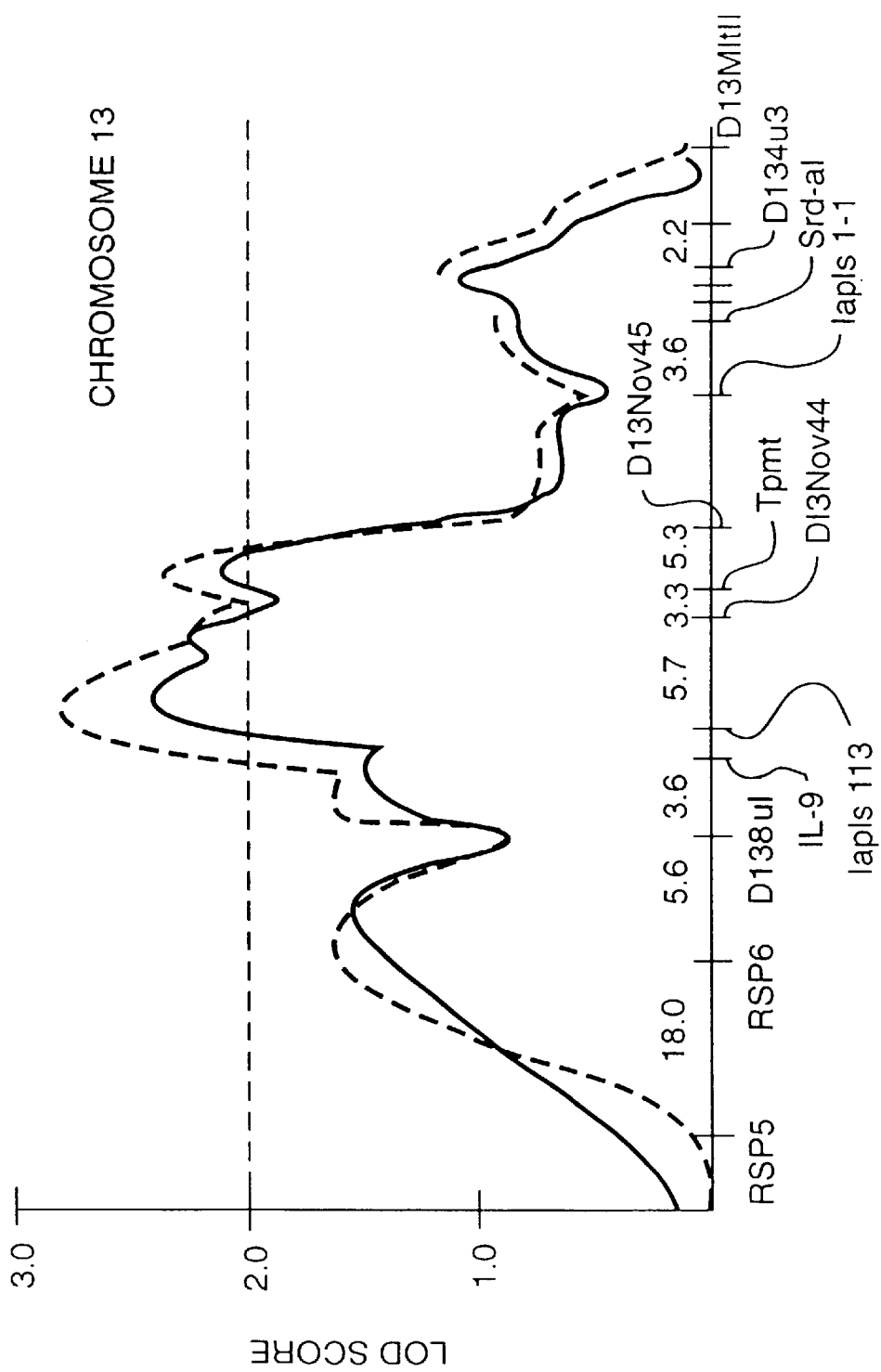
FIG. 3: The LOD score curve on mouse chromosome 13 for atracurium-induced airway responsiveness in mice with increased susceptibility to bronchoconstrictor stimuli.

Despite comparisons with four candidate intervals, evidence for linkage was found for only one region, designated Aib 1 [atracurium induced bronchoconstriction 1]. FIG. 3 provides the results. Specifically, FIG. 3 sets forth the LOD score curve on mouse chromosome 13 for atracurium-induced airway responsiveness in 24 BXD RI strains which are derived from the hyporesponsive C57BL/6J and the hyperresponsive DBA/2J progenitor strains [solid line]. The LOD score curve resulting from the selective genotyping of 20 BXD strains is also shown [dashed line]. BXD strains -2, -6, -18, and -32 were not used in the second analysis since they were intermediate in phenotype displaying a mean response greater than 1 standard deviation below the DBA/2 and above the C57BL/6 mean responses. The bronchoconstrictor response to atracurium, 20 mg/kg given intravenously, was assessed by the change in peak inspiratory pressure integrated over time [4 min], termed the airway pressure time index [APTI]. Atracurium-induced APTI was measured in 2–8 animals per RI strain. Marker data were obtained from the RWE data base in the Map Manager data analysis program. The genetic distance [cM] between markers is indicated on the abscissa. LOD scores were calculated by the MAPMAKER/QTL linkage program. A QTL was detected in this region and termed atracurium-induced bronchoconstriction-1 [Aib1].

FIG. 3 indicates that this quantitative trait locus [QTL] is located on the midportion of murine chromosome 13 and attained this interval a maximum likelihood log of the odds [LOD] of 2.42. Forty-four percent of the total variance in atracurium-induced bronchoconstriction was explained at Aib1 when all of the markers in the BXD map were analyzed. The LOD for chromosome 13 increased to 2.85 when QTL analyses were run after excluding the four strains [BXD-2, -6, -18, and -32] that were intermediate responders to atracurium. The known positional candidates in the linked region of chromosome 13 include: D1 dopamine receptor [Drdl], fibroblast growth factor receptor 4 [Fgfr4], lymphocyte antigen-28 [Ly28], thiopurine methyltransferase [Tpmt], and IL-9.

Because the applicant was specifically testing for linkage to four candidate regions in the mouse, based on previous mapping data in the human, the data presented here are highly significant. As stated in the classic paper by Lander and Botstein,[67] a false positive rate for linkage will result if the LOD threshold (T) is chosen so that T=½(log10 e)(Z α/n)2 (where n is equal to the number of intervals tested). Typically a minimum LOD of 3.3 is required as evidence of linkage.[67] However, this threshold is based on the assumption that one is searching the entire genome. These same authors point out that a LOD of 0.83 is sufficient when only one region is examined. In this case, with four candidate regions, a P value (α) of 0.0125 for each region is required to obtain a true P≦0.05, when one corrects for multiple independent comparisons. Adopting a 5% error rate that even a single false positive finding will occur, as suggested by Soller and Brody,[68] and solving the equation ½(log10 e)(Z α/n)$^2$, yields a LOD threshold of at least 1.36. A maximal LOD of 1.48 was obtained for the Il-9 gene candidate. Restricting the acceptable false positive error rate to ≦0.1%, increases the LOD threshold to 2.36. Thus, the maximal LOD generated of 2.42 for the candidate interval on chromosome 13 (Aib1) is highly significant.

These LOD threshold data provide evidence of a conserved linkage for BHR in humans and mice. BHR in humans links to the region on chromosome 5q containing a number of growth factors and cytokines including the IL-9 gene and the Aib1 locus maps to the IL-9 region of murine chromosome 13.

EXAMPLE 2

Identification of an IL-9 Gene Polymorphism

Applicant demonstrated conserved linkage between the mouse and humans for BHR. These data suggest that variation in the functions of this gene or DNA sequence may be important in regulating bronchial responsiveness in the mouse. Using the methods described above, a unique product of the correct size was identified by gel electrophoresis for each of the exons of human IL-9 after PCR. A single polymorphism was identified by SSCP in exon 5 of the human IL-9 gene. Direct DNA sequence analysis demonstrated a C to T nucleotide substitution at position 3365 [GenBank accession number M30136] of the human IL-9 gene as the cause of the novel SSCP conformer. This DNA sequence change predicts a nonconservative substitution of a methionine [hydrophobic] for a threonine [hydrophilic] at amino acid 117 of the IL-9 protein.

Exon 5 codes for this segment of the protein which is within the most highly conserved interval of human IL-9 as compared to the mouse IL-9 sequence (see FIG. 4).

Individuals were genotyped from various populations to examine the frequency of these alleles by direct analyses of the nucleotide substitution in the coding sequence of human IL-9. Two of 394 individuals from a group of asthmatic families were homozygous [Met/Met] at codon 117 [0.5%]. There were 91 [23.1%] heterozygous, and 301 [76.4%] homozygous [Thr/Thr] individuals. The true prevalence for this IL-9 variant is likely to be significantly higher because the Italian population of families was ascertained through symptomatic patients with asthma. From a separate ethnically diverse population ascertained randomly with respect to atopy and asthma, there were 1 of 49 individuals homozygous for [Met/Met] at codon 117 [2.0%]. There were 11 [22.4%] heterozygous, and 37 [75.5%] homozygous [Thr/Thr] individuals. The prevalence of the Met/Thr heterozygotes was 18.9% in a fourth population ascertained randomly with respect to atopy and asthma. Thus, approximately 20% of the population are likely to represent carriers of the T allele at position 3,365 as compared to the reported sequence [GenBank accession number M30136]. Because it is well known in the art that the frequency of any allele in the population is p2+2pq+q2, then, approximately 4% of the population is expected to be Met/Met homozygous at codon 117 of IL-9.

Figure 5:
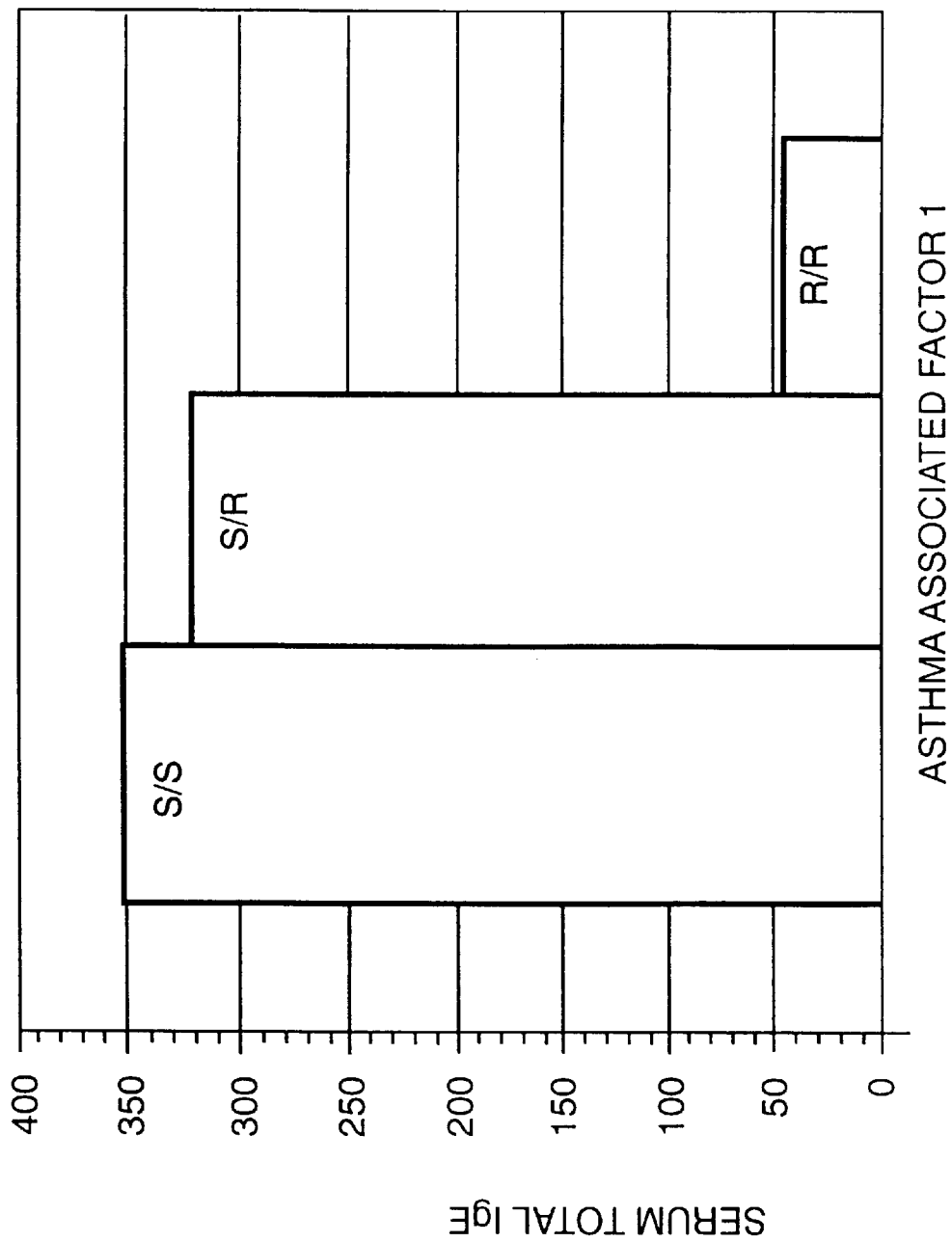
FIG. 5: Histogram of the correlation between human IL-9 gene alleles and serum total IgE titers measured in international units. S/S denotes Thr/Thr individuals, S/R denotes Thr/Met individuals and R/R denotes Met/Met individuals.

Overall, serum total IgE averaged 44.5 I.U. for homozygous individuals [Met/Met], which was significantly different from those who were homozygous wild type [Thr/Thr] [351.7I.U.], or heterozygous [Met/Thr] [320.9 I.U.]. See FIG. 5. The homozygous protected individuals [Met/Met] failed to demonstrate evidence of atopic allergy except for a single positive skin test in one individual. These data indicate that this novel DNA polymorphism, when inherited in the homozygous state, is associated with protection from atopic allergy, including lower serum total IgE.

Figure 6:
FIG. 6: Illustration the simple sequence repeat polymorphism at the IL-9 locus.
Figure 9:
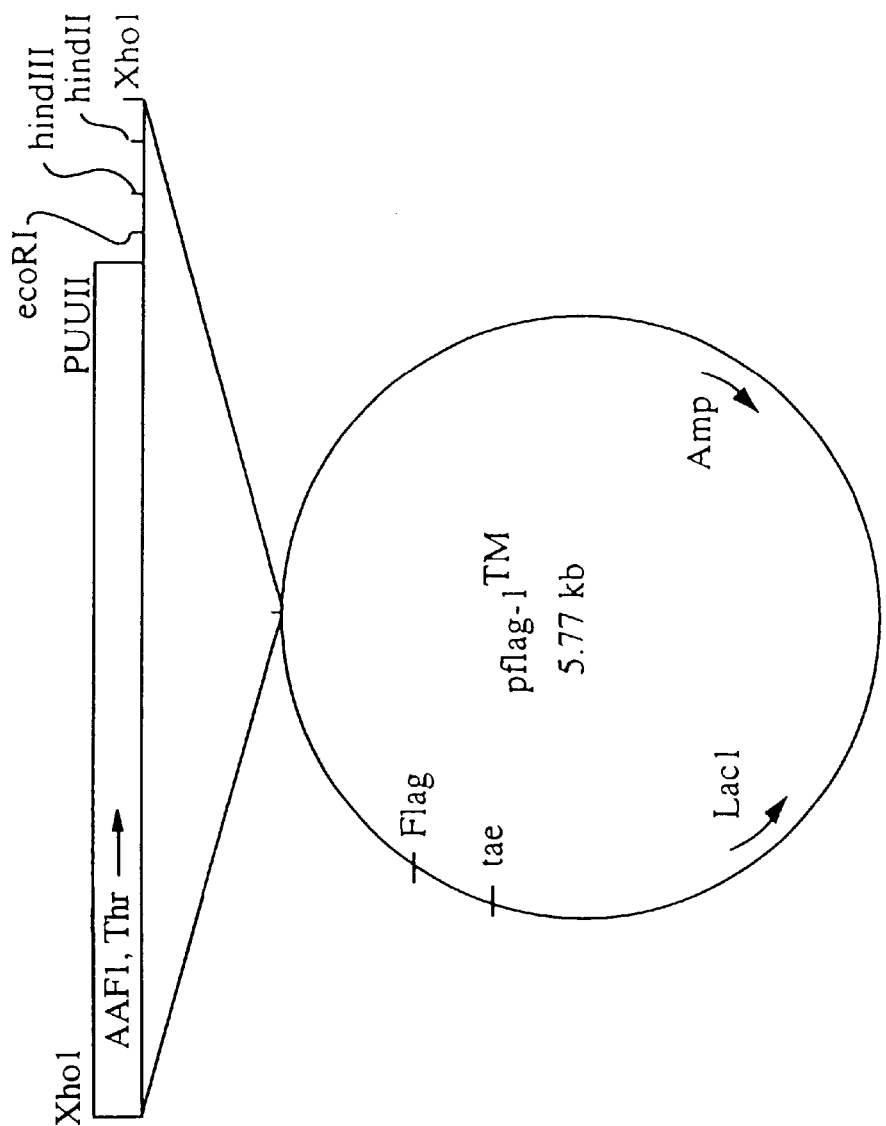
FIG. 9: Map of pFlag expression construct with Thr117.
Figure 11:
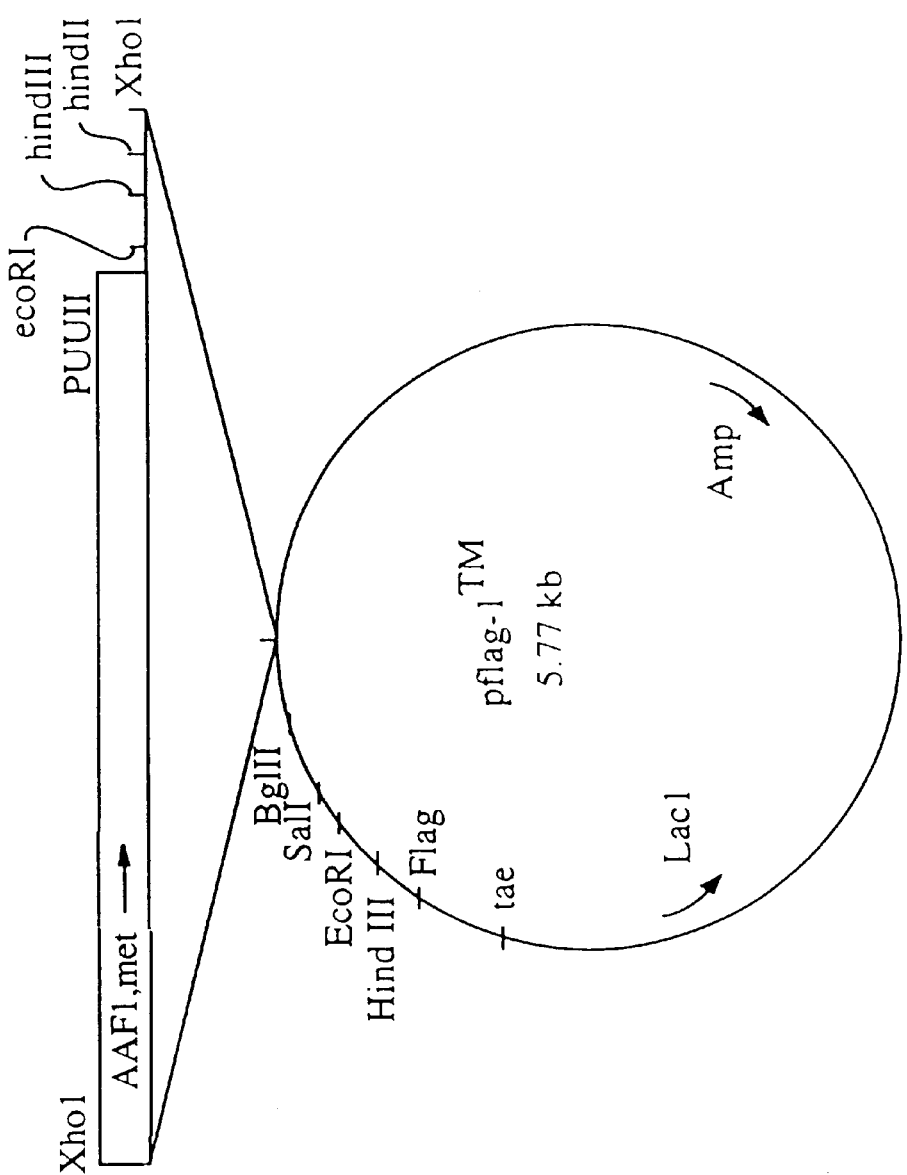
FIG. 11: Map of pFlag expression construct with Met117.

FIG. 6 illustrates the PCR amplification of the IL-9 simple sequence repeat polymorphism. This marker is compared with genotype for these individuals for the restriction fragment length polymorphism produced by the nucleotide polymorphism at position 3,365 as compared to the reported sequence [GenBank accession number M30136]. Two families are shown. The individuals in lanes 1 and 2 are the parents (Thr/Met) of individuals in lanes 3 (Met/Thr) and 4 (Met/Met); lanes 5 (Thr/Thr) and 6 (Met/Met) are parents for offspring in lanes 7 (Met/Thr) and 8 (Met/Thr). The smallest allele for the IL-9 simple sequence repeat polymorphism (the lowest band in each figure is 248 nucleotides in length) is in complete linkage disequilibrium with the Met117 allele (nucleotide substitution at position 3,365 as compared to the reported sequence [GenBank accession number M30136]) in these individuals and in all individuals from populations tested world wide. This was true in both the Italian and all random ascertained ethnically diverse individuals studied, and therefore, this marker may be used diagnostically to detect the presence of the Met117 allele. These data are most consistent with the hypothesis that this variant is widely distributed in populations worldwide and arose before many of these populations separated.

EXAMPLE 3

IL-9 Receptor Expression and Ligand Binding Assay

Purified recombinant Thr IL-9, Met IL-9, and compounds potentially resembling Met IL-9 in structure or function are radiolabelled using the Bolton and Hunter reagent as described in Bolton A E, and Hunter W M, Biochem J. 133:529–539(1973). This material is labeled to high specific activity of 2,300 cpm/fmol or greater. Human K562 and MO7e cells are grown and resuspended at 30° C. in 0.8 ml of Dulbecco's modified Eagle's medium supplemented with 10% (vol/vol) fetal bovine serum, 50 mM 2-mercaptoethanol, 0.55 mM L-arginine, 0.24 mM L-asparagine, and 1.25 mM L-glutamine. K562 or MO7e cells are used as is or after transfection with the IL-9 receptor gene as described below. Plasmid DNA containing the full length IL-9 receptor is cloned into pRC/RSV plasmid (In Vitrogen, San Diego) and purified by centrifugation through CsCl2. Plasmid DNA (50 micrograms) is added to the cells in 0.4 cm cuvettes just before electroporation. After a double electric pulse (750V/74 ohms/40 microFaradays and 100 V/74 ohms/2100 microFaradays) the cells are immediately diluted in fresh medium supplemented with IL-9. After 24 h the cells are washed and incubated in G418 (2.5 mg/ml, GIBCO) with either no ligand, or various concentrations of 125I-labeled ligand at 20° C. for 3 h. An excess of unlabeled ligand is used in parallel experiments to estimate nonspecific binding. The cells are then washed, filtered, and collected for counting. Specific incorporation is calculated by Scatchard analysis. Similar competitive assays are run using 125I-labeled Thr117 IL-9 and various amounts of putative cold ligands to assess specific binding.

Soluble IL-9 receptor including amino acids 44 to 270 (R&D Systems) was incubated with different forms of human recombinant IL-9. Varying amounts of FlagMet117 and FlagThr117 (described in Example 7) were incubated in PBS at room temperature for 30 minutes with 0.5 µgs of soluble receptor. EBC buffer (50 mM Tris pH 7.5; 0.1 M NaCl; 0.5% NP40) was added (300 µl) was added along with 1 µg of anti-FLAG monoclonal antibody (IBI) and incubated for 1 hour on ice. Forty microlitres of protein A sepharose solution was added to each sample and mixed for 1 hour at 4° C. Samples were centrifuged for 1 minute 11,000×G and pellets were washed 4 times with 500 µl of EBC. Pellets were dissolved in 26 µl of 2×SDS buffer, boiled for 4 minutes, and electrophoresed through an 18% SDS polyacrylamide gel. Western blots were performed as described in Example 15 except the blots were probed with an anti-IL-9 receptor antibody (R&D Systems).

Figure 25:
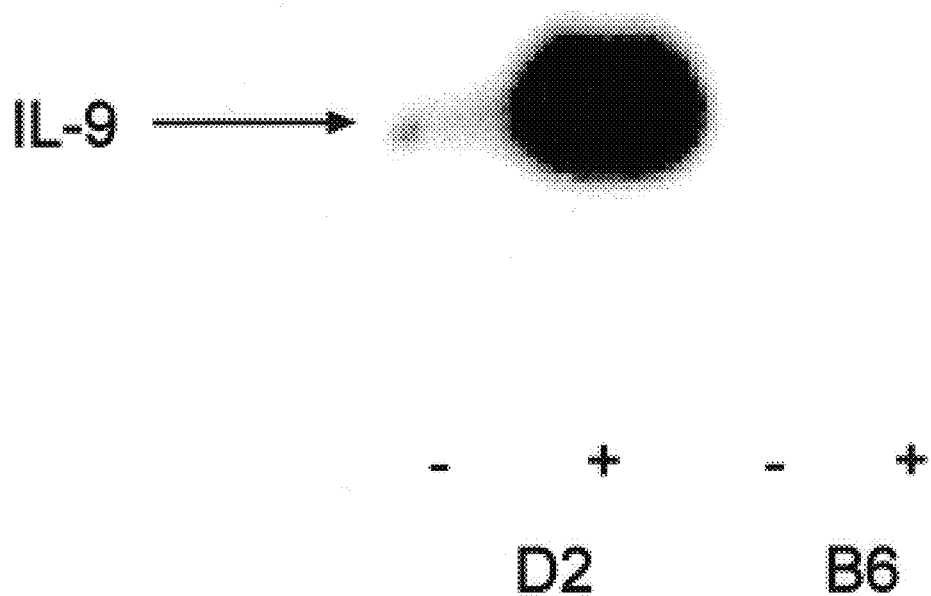
FIG. 25: Steady state levels of IL-9 in unstimulated and stimulated murine splenocytes.

FIG. 25 demonstrates the binding of the IL-9 recombinant proteins soluble IL-9 receptor. Lane 1 is molecular weight markers, lane 2 is the IL-9 FlagMet117 incubated with the receptor, lane 3 is the IL-9 FlagThr117 incubated with the receptor. These data demonstrate that both forms of the recombinant IL-9 protein are bound to the soluble receptor. Moreover, these data along with those of Example 2 (where hetrozygotes do not differ in serum Ig-E from homozygous Thr117 individuals) are consistent with the IL-9 Met117 form representing a weak agonist.

EXAMPLE 4

IL-9 Receptor Expression and Ligand Functional Assay in K562, C8166-45, and MO7e cells Recombinant Thr117 IL-9, Met117 IL-9, and compounds potentially resembling Met IL-9 in structure or function were purified and prepared for use in Dulbecco's modified Eagle's medium. K562, C8166-45 or MO7e cells are used as is or after transfection with the IL-9 receptor gene as described in Example 3. After 24 h of deprivation from growth factors the cells are incubated without (control) or with variable amounts of purified Thr117 IL-9, Met117 IL-9, and compounds potentially resembling Met117 IL-9 in structure or function. Cellular proliferation is assessed by measuring acid phosphotase activity. Briefly, quadruplicate samples of MO7e cells are cultured in flat-bottom microtiter plates (150 or 200 microliter wells) with or without ligand for 72 to 96 hours at 37 degrees C. Acid phosphatase is measured as suggested by the manufacturer (Clontech, Palo Alto, Calif.). All experiments are repeated at least twice.

EXAMPLE 5

Cell Isolation and Culture

Human peripheral blood mononuclear cells {PBMC} were isolated from healthy donors by density gradient centrifugation using endotoxin tested Ficoll-Paque PLUS according to the manufacturer (Pharmacia Biotech, AB Uppsala Sweden). PBMC ($5 \times 10^6$), mouse spleen cells ($5 \times 10^6$), or $5 \times 10^6$ MO7e cells were cultured in 7 ml of RPMI-1640 (Bethesda Research Labs (BRL), Bethesda, Md.) supplemented to a final concentration of 10% with either isogenic human serum or heat-inactivated FBS. Cells were cultured for 24 hrs at 37° C. either unstimulated, or stimulated with either PMA 5 µg/ml/ PHA 5 µg/ml, or PHA 5 µg/ml/rhIL2 50U (R&D Systems, Minneapolis, Minn.).

EXAMPLE 6

RNA Isolations, RT-PCR, Cloning and Sequencing of RT-PCR Products

Total cellular RNA was extracted after 24 hrs from cultured PBMC, mouse spleen cells, and MO7e cells using RNA PCR corekit (Perkin-Elmer Corp, Foster City, Calif.) according to the supplier. One µg of RNA from each source was denatured for 5 minutes at 65° C. and then reverse transcribed into cDNA using a 20 µl reaction mixture (RNA PCR corekit, Perkin-elmer Corp, Foster City, Calif.) containing 50U of MuMLV Reverse Transcriptase, 1U/µl RNAse Inhibitor, 2.5 mM oligo d(T)16 primer, 1 mM each of dATP, dCTP, dGTP, dTTP, 50 mM KCl, 10 mM Tris-HCL, pH 7.0, 25 mM MgCl2. The reaction mixture was pipetted into thermocycler tubes, placed in a PCR thermal cycler and subjected to 1 cycle (15 minutes at 42° C., 5 minutes at 99° C., and 5 minutes at 4° C.). A mock reverse transcription reaction was used as a negative control.

Then this mixture was added to a second tube containing 2 mM MgCl2, 50 mM KCl, 10 mM Tris-HCl, pH 7.0, 65.5 µl of DI water, 2.5U Amplitaq DNA polymerase, and 1 µl (20 µM) each of oligonucleotides representing human cDNA IL-9 exon 1 (forward) and exon 5 (reverse), for a final volume of 100 µl. The reaction mixture was subjected to the following PCR conditions: 120 seconds at 98° C., then 30 cycles at: 30 seconds at 94° C.; 40 seconds at 55° C.; 40 seconds at 72° C. Finally, the reaction mixture was cycled one time for 15 minutes at 72° C. for extension.

PCR products representing hIL-9 cDNA were subjected to gel electrophoresis through 1.5% agarose gels and visualized using ethidium bromide staining. Products of a mock reverse transcriptase reaction, in which $H_2O$ was substituted for RNA, and used as negative control amplification in all experiments.

The PCR oligonucleotide primer pairs used in these experiments to amplify cDNA include: human interleukin 9 (hIL-9) exon 1 forward 5'-TCT CGA GCA GGG GTG TCC AAC CTT GGC G-3' (SEQ ID NO: 1) and exon 5 reverse 5'GCA GCT GG ATA AAT AAT ATT TCA TCT TCA T-3' (SEQ ID NO: 2); mouse interleukin 9 (mIL-9) exon 1 forward 5'-TCT CGA GCA GAG ATG CAG CAC CAC ATG GGG C-3' (SEQ ID NO: 3) and mouse exon 5 reverse 5'-GCA GCT GGT AAC AGT TAT GGA GGG GAG GTT T-3' (SEQ ID NO: 4); XhoI and PvuII restriction enzyme recognition sequences are underlined in the human and mouse IL-9 primers, PCR products were subcloned into the TA Cloning vector (Invitrogen, San Diego, Calif.). Amplification of the mouse cDNA gave a 438 bp product and amplification of the human cDNA gave a 410 bp product.

Complementary DNAs for human IL-9 and murine mIL-9 were generated and amplified by RT-PCR using IL-9 exon 1 and 5 specific primers containing digestion sites for XhoI and PvuII restriction endonucleases. Amplification products for hIL-9 and mIL-9 were isolated from 2.5% agarose gels using silica(Sambrook, J. et al. (1989) *Molecular Cloning: A Laboratory Manual* Cold Spring Harbor Laboratory Press, New York) (incorporated herein by reference in its entirety). After recovery, the cDNA products were ligated into the TA Cloning vector (Invitrogen Corp., San Diego, Calif.) and then used to transform INVαF' competent cells, according to the manufacturer's instructions. Plasmids containing hIL-9 and mIL-9 cDNA inserts were isolated by conventional techniques (Sambrook, J. et al. (1989) *Molecular Cloning: A Laboratory Manual* Cold Spring Harbor Laboratory Press, New York). After amplification the DNA sequence including and surrounding each insert was analyzed for PCR-induced or cloning-induced errors.

hIL-9 and mIL-9 cDNA inserts were sequenced by the dideoxy-mediated chain termination method (Sanger et al. (1977) Proc. Natl. Acad. Sci. USA 74:5463), using the M13 (−20) forward primer (5'-GTA AAA CGA CGG CCA GT-3') (SEQ ID NO: 17) and Sequenase™ (USB), and analyzed by gel electrophoresis (Sambrook, J. et al. (1989) *Molecular cloning: a laboratory manual* Cold Spring Harbor Laboratory Press, New York). hIL-9 and mIL-9 cDNA inserts without cloning and/or Taq polymerase-induced sequence errors (see translated cDNA sequences FIGS. 7 and 8) were subcloned into expression vectors (see FIGS. 9–12) or used to create missense mutations and deletion mutants.

EXAMPLE 7

Cloning and Expression of IL-9 Constructs in Vitro
General Cloning Methods for Constructs hIL-9 was subcloned into procaryotic expression vectors. The TA2AAF1 met and thr vectors were digested by EcoRI and the 0.420 kB fragment (containing an XhoI site at the 5' end of the hIL9 cDNA) was cloned into the EcoRI site contained with the polylinker of pBluescript (PBS) (Stratagene). Clones in the sense orientation to the T3 promoter were then digested with XhoI (the fragment contained a 5' XhoI site from the IL-9 cDNA insert from TA vectors and a 3' XhoI site from the PBS polylinker) and inserts were subcloned into the XhoI sites of the procaryotic expression vectors pGEX and pFLAG.

Cloning and expression of IL-9 constructs in the pGEX-4T-1 glutathione s-transferase gene fusion vector For the expression, purification, and detection of IL-9 protein, IL-9 cDNA inserts were subcloned into the XhoI site within the multiple cloning cassette of the 4.9 Kb pGEX-4T-1 glutathione s-transferase gene fusion vector (Pharmacia Biotech, Piscataway, N.J.) by standard techniques. Briefly, TA clones containing intact IL-9 cDNA sequences, and the pGEX-4T-1 vector were digested for one hour at 37° C. using XhoI and PvuII restriction endonuclease in the presence of 1×React 2 buffer (New England Biolabs, Beverly, Mass.) (total volume 50 μl). Products were electrophoresed in a 1.5% preparative agarose gel with 10 μg/ml ethidium bromide. The appropriate sized DNA band was excised, the agarose was melted at 45° C. for 10 minutes in 3 volumes of NaI stock solution. A silica matrix solution in DI $H_2O$ (Geneclean II, LaJolla, Calif.) was added to the solution at 5 μl per 5 μg of DNA and 1 μl per 0.5 μg of DNA above 5 μg. The slurry was incubated at 4° C. and occasionally shaken during 30 minutes. The slurry was then pelleted via microcentrifugation, washed 3 times in low-salt buffer and resuspended in 10 μl of DI $H_2O$ to elute the DNA from the silica. A final microcentrifugation provided the 10 μl solution containing purified DNA.

Products were resuspended in 50 μl of DI $H_2O$ and precipitated by the addition of 2 volumes of ethanol and 1/10 volume 3M sodium acetate. Samples were centrifuged at RT at 14,000 rpm for 10 minutes, air dried under negative pressure and resuspended in an appropriate volume of DI $H_2O$. Ligations and transformations of DH5α bacteria (GIBCO/BRL, Gaithersburg, Md.) with mIL-9 and hIL-9 cDNA inserts in the pGEX-4T-1 vector were performed using standard techniques.

To confirm that the hIL-9 cDNA inserts contained in the pGEX-4T-1 vector were of the correct nucleotide sequence, plasmids containing candidate IL-9 cDNA were sequenced via the dideoxy-mediated chain termination method using the aforementioned mIL-9 and hIL-9 cDNA-specific oligonucleotides (exon 1 forward, exon 5 reverse primers).

Recombinant fusion proteins were obtained from large scale cultures. The overnight culture of transformed *E. coli* (50 ml) was inoculated into fresh LB/amp broth. The culture was incubated for 4 hr at 37° C. with vigorous shaking, isopropyl β-D-thiogalactopyranoside was then added to a final concentration of 1 mM, and the culture was incubated for an additional 1.5 h. The cells were harvested by centrifugation at 500×g at 4° C. and recombinant variants were purified by making use of affinity chromatography on glutathione-sepharose 4B column (Pharmacia) for GST-fusion proteins. Some variants were expressed as inclusion bodies and were purified from insoluble inclusion bodies by the procedure described by Marston (1987 The purification of eukaryotic polypeptides expressed in *E.coli* in Clover D. M. ed. *DNA cloning: A practical approach*, IRL Press, Oxford, 59–88). Briefly, the cells were lysed with lysozyme followed by treatment with deoxycholic acid. Contaminating nucleic acids were removed by treatment with DNase I. The insoluble material was washed once with 2 M urea and finally solubilized in lysis buffer (50 mM Tris-Cl, pH 8.0, 1 mM EDTA, 100 mM NaCl) containing 8 M urea. The solubilized components from the inclusion bodies were dialyzed stepwise against decreasing concentrations of urea (starting with 8, 6, 4 and 2 M of urea) in lysis buffer to allow for refolding of the denatured protein. Finally, the sample was dialyzed against 2 M urea and 2.5% β-mercaptoethanol (β-ME) and centrifuged at 10,000 g for 15 min. The fusion protein was finally dialyzed against 0.01 M Tris-Cl, pH 8.0. Fusion proteins expressed in pGEX-4T vector were cleaved with 100 U of Thrombin for 6 hr at 37° C. and recovered in flow through fractions after chromatography on glutathione-Sepharose 4B column. Final purification was achieved by chromatography on Sephadex G-100 column (100×1.5 cm), packed and equiliberated with 0.05 M ammonium bicarbonate buffer.

Cloning and Expression of IL-9 Constructs in the pFLAG-1™ Expression Vector

For the expression, purification and detection of human IL-9 protein, IL-9 cDNA inserts were subcloned into the Xho2 site of the multiple cloning site (XhoI) of the 5.37 Kb Flag vector. FLAG technology is centered on the fusion of a low molecular weight (1kD), hydrophilic, FLAG marker peptide to the N-Terminus of a recombinant protein expressed by the pFLAG-1™ Expression Vector(1) (obtained from IBI Kodak). Each bacterial colony was grown in LB broth containing 50 μg ampicillin per ml until the optical density at 590 nm reached 0.6. IPTG was then added to a final concentration of 1 mM, and the cultures incubated for an additional 1 hr to induce protein synthesis. The cells were harvested by centrifugation, and the cell pellet was boiled in 50 μl of Laemmli buffer (Laemmli, 1970) for 10 min and electrophoresed on 10% polyacrylamide gels. The Anti-FLAG™ M1 monoclonal antibody was used for specific and efficient detection of the FLAG fusion protein on western (see FIG. 13) slot or dot blots throughout its expression, affinity purification, and FLAG marker removal. The FLAG fusion protein was rapidly purified under mild, non-denaturing conditions in a single step by affinity chromatography with the murine Anti-FLAG™ IgG M1 monoclonal antibody covalently attached to agarose. Following affinity purification the fusion protein may be used after removal from the affinity column or the authentic protein may be recovered in biologically active form by specific and efficient proteolytic removal of the FLAG peptide with enterokinase. Final purification was achieved by chromatography on Sephadex G-100 column (100×1.5 cm), packed and equiliberated with 0.05 M ammonium bicarbonate buffer. The promoters described above in this example may also be used with FLAG technology.

SDS-PAGE and Imrnmunoblot Analysis

Figure 13:
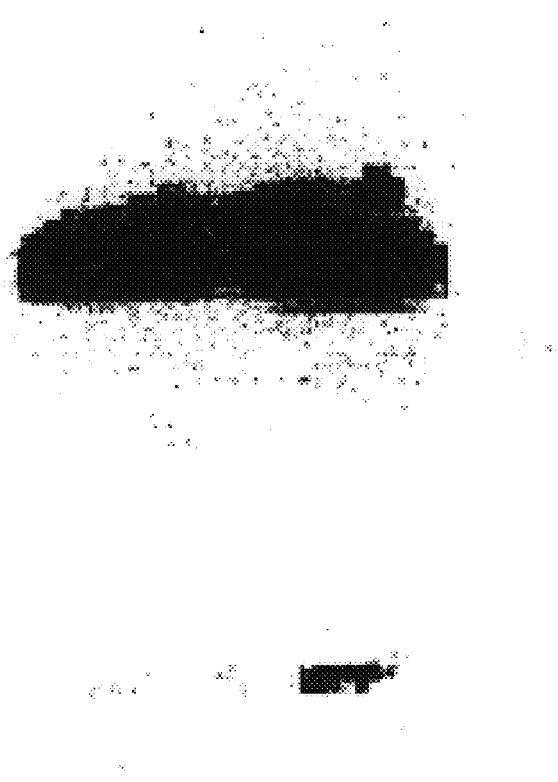
FIG. 13: Western blot of recombinant IL-9 proteins

SDS-PAGE was performed by the method of Laemmli (Laemmli U.K. (1970) Nature 227, 680–685)(incorporated herein by reference in its entirety) by using a 12.5% polyacrylamide gel in a mini-gel system (SE 280 vertical gel unit, Hoefer). For immunoblot analysis, the proteins separated by SDS-PAGE were transferred to nitrocellulose membranes by using the TE 22 Mighty small transfer unit (Hoefer) in 25 mM Tris-glycine buffer, pH 8.3, containing 15% methanol (Towbin H., et al., (1979) Proc. Natl. Acad. Sci. U.S.A. 76, 4350–4354). The unoccupied binding sites on the membrane were blocked by incubating for 1 h with 20 mM Tris-HCl buffer, pH 8.0, containing 2% bovine serum albumin. The membranes were then incubated with 1:200 dilution of antibodies overnight at 4° C. The membranes were washed and treated with 1:2000 diluted goat anti-rabbit IgG conjugated with either peroxidase or alkaline phosphotase for 1 h. After washing, the bound antibodies were visualized by addition of the super-substrate chemiluminescent reagent (Pierce) or the 4-chloro-1-naphthol color developing reagent. The reaction was stopped by immersing the membranes in distilled water. FIG. 13 demonstrates that the purified recombinant human FLAG IL-9 fusion proteins (Met117 and Thr117) are the correct size and in the correct reading frame because they are recognized by the Anti-FLAG™ M1 monoclonal antibody.

Analytical Methods

The molecular mass of the purified proteins was confirmed by matrix assisted laser desorption mass spectrometry using Perceptive Biosystems voyager Biospectrometry workstation. Amino acid analyses were performed after hydrolysis of the sample in 6N HCl at 110-C for 24h in evacuated sealed glass bulbs.

Automated Edman Degradation

The partial amino acid sequence of the purified proteins is determined by automated step-wise sequencing on an Applied Biosystems model 477A gas-phase sequencer with an on-line model 20A PTH analyzer.

EXAMPLE 8

Deletion of Exon 2 and/or Exon 3: Mutagenesis and Sequencing of Constructs

Human exon 2 and exon 3 deletions are created using ExSite PCR-based site-directed mutagenesis kit as suggested by the manufacturer (Stratagene, La Jolla, Calif.). The PCR primers are as follows: h9CD1U forward 5'-GTG ACC AGT TGT CTC TGT TTG-3' (SEQ ID NO: 5); h9CD1L reverse 5'-CTG CAT CTT GTT GAT GAG GAA-3' (SEQ ID NO: 6); h9CD2U forward 5'-GAC AAC TGC ACC AGA CCA TGC-3' (SEQ ID NO: 7); h9CD2L reverse 5'-ATT AGC ACT GCA GTG GCA CTT-3' (SEQ ID NO: 8). Exon 2 deletions are created by using the primer pair h9CD1L forward and h9CD1L reverse. Exon 3 deletions are created by using h9CD2U forward and h9CD2L reverse. Deletions that included exon 2 and exon 3 use the primer pair h9CD2U forward h9CD1L reverse.

Mouse exon 2 and exon 3 deletions are created using ExSite PCR-based site-directed mutagenesis kit as suggested by the manufacturer (Stratagene, La Jolla, Calif.). The PCR primers are as follows: m9CD1U forward 5'-GTG ACC AGC TGC TTG TGT CTC-3' (SEQ ID NO: 9); m9CD1L reverse 5'-CTT CAG ATT TTC AAT AAG GTA-3' (SEQ ID NO: 10); m9CD2U forward 5'-GAT GAT TGT ACC ACA CCG TGC-3' (SEQ ID NO: 11); m9CD2L reverse 5'-GTT GCC GCT GCA GCT ACA TTT-3' (SEQ ID NO: 12). Exon 2 deletions are created by using the primer pair m9CD1U forward and m9CD1L reverse. Exon 3 deletions are created by using m9CD2U forward and m9CD2L reverse. Deletions that included exon 2 and exon 3 use the primer pair m9CD2U forward m9CD1L reverse.

Mutagenized constructs of the hIL-9 and mIL-9 cDNA inserts are sequenced by the dideoxy-mediated chain termination method (Sanger et al. (1977) Proc. Natl. Acad. Sci. USA 74:5463) (incorporated herein by reference in its entirety), using the M13 (−20) forward primer (5'-GTAAAACGACGGCCAGT-3') (SEQ ID NO: 18) and Sequenase™ (USB), with analysis by gel electrophoresis (Sambrook, J. et al. (1989) *Molecular cloning: a laboratory manual* Cold Spring Harbor Laboratory Press, New York). Mutants that lack exon 2, exon 3, or both exon 2 and exon 3, and are without Taq polymerase-induced sequence errors can be used to create expression vectors.

EXAMPLE 9

Cell Lines, Cellular Proliferation Assays and Inhibition of IL-9 Activity

Cell lines were used to assess the function of peptides, aminosterols, tyrophostins, rhIL-9, rmIL-9, and recombinant mutant forms of these proteins as well as all other compounds that block IL-9 function. A proliferative response was measured and compared to each of the other cytokines, variant or mutant forms of Il-9, or IL-9 antagonists. In addition, compounds were tested for their ability to antagonize the baseline proliferative response. Once a baseline proliferative response was established for a cytokine a statistically significant loss of response in assays repeated three times in triplicate was considered evidence for antagonism. A true antagonistic response was differentiated from cellular toxicity by direct observation, trypan blue staining (a technique well known to one of normal skill in the art), and loss of acid phosphatase activity. Specificity was assessed for the antagonist by evaluating whether the activity was substantially expressed against other proliferative agents such as steel factor, interleukin 3, or interleukin 4.

The MO7e line is a human megakaryoblastic cell line, cultured in RPMI 1640 (GIBCO/BRL, Gaithersburg, Md.), 20% Fetal Bovine Serum (Hyclone) and 10 ng/ml IL-3 (R&D Systems, Minneapolis, Minn.). The MJ line is a cytokine independent human lymphoblastoid cell line grown in RPMI 1640 (GIBCO/BRL) K562 is a human erthroleukemia cell line, cultured in RPMI 1640 (GIBCO/BRL) and 10% fetal bovine serum (Hyclone). C8166-45 is a IL-9 receptor bearing line, cultured in RPMI 1640 GIBCO/BRL) and 10% Fetal bovine serum (Hyclone). All the cell lines respond to cytokines including IL-9. The cell lines are fed and reseeded at $2 \times 10^5$ cells/ml every 72 hours.

The cells were centrifuged for 10 minutes at 2000 rpm and resuspended in RPMI 1640 with 0.5% Bovine Serum Albumin (GIBCO/BRL, Gaithersburg, Md.) and insulin-transferrin -selenium (ITS) cofactors (GIBCO/BRL, Gaithersburg, Md.). Cells were counted using a hemocytometer and diluted to a concentration of $1 \times 10^5$ cells/ml and plated in a 96-well microtiter plate. Each well contained 0.15 or 0.2 ml giving a final concentration of $2 \times 10^4$ cells per well.

MO7e cells were stimulated with 50 ng/ml Stem Cell Factor (SCF) (R&D Systems, Minneapolis, Minn.) alone, 50 ng/ml SCF plus 50 ng/ml IL-3 (R&D Systems, Minneapolis, Minn.), or 50 ng/ml SCF plus 50 ng/ml IL-9. A control was included which contains cells and basal media only. Serial dilutions of test compounds (i.e, recombinant IL-9 proteins, peptides, small molecules) were added to each test condition in triplicate. The MJ cell line was used as an independent control for nonspecific cytotoxicity. Cultures were incubated for 72–96 hours at 37° C. in 5% $CO_2$.

Cell proliferation was assayed using the Abacus Cell Proliferation Kit (Clontech, Palo Alto, Calif.) which determines the amount of intracellular acid phosphatase present as an indication of cell number. The substrate p-nitrophenyl phosphate (pNPP) was converted by acid phosphatase to p-nitrophenol which was measured as an indicator of enzyme concentration. pNPP was added to each well and incubated at 37° C. for one hour. 1N sodium hydroxide was then added to stop the enzymatic reaction, and the amount of p-nitrophenol was quantified using a Dynatech 2000 plate reader (Dynatech Laboratories, Chantilly, Va.) at 410 nm wavelength. Standard curves that compare cell number with optical absorbance were used to determine the linear range of the assay. Assay results were only used when absorbance measurements are within the linear range of the assay.

Figure 15:
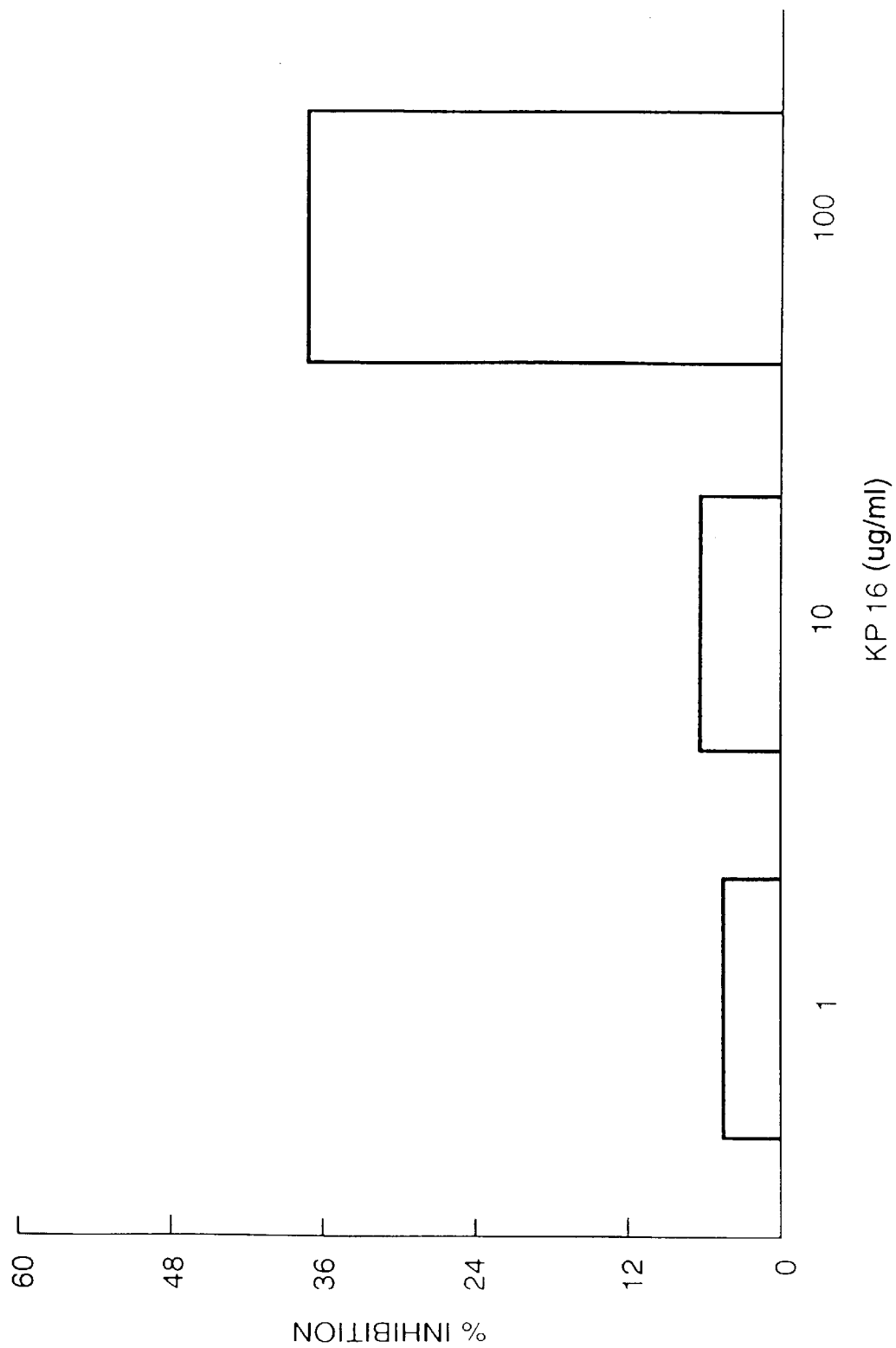
FIG. 15: Inhibition by KP-16 of IL-9 mediated MO7e proliferation.
Figure 16:
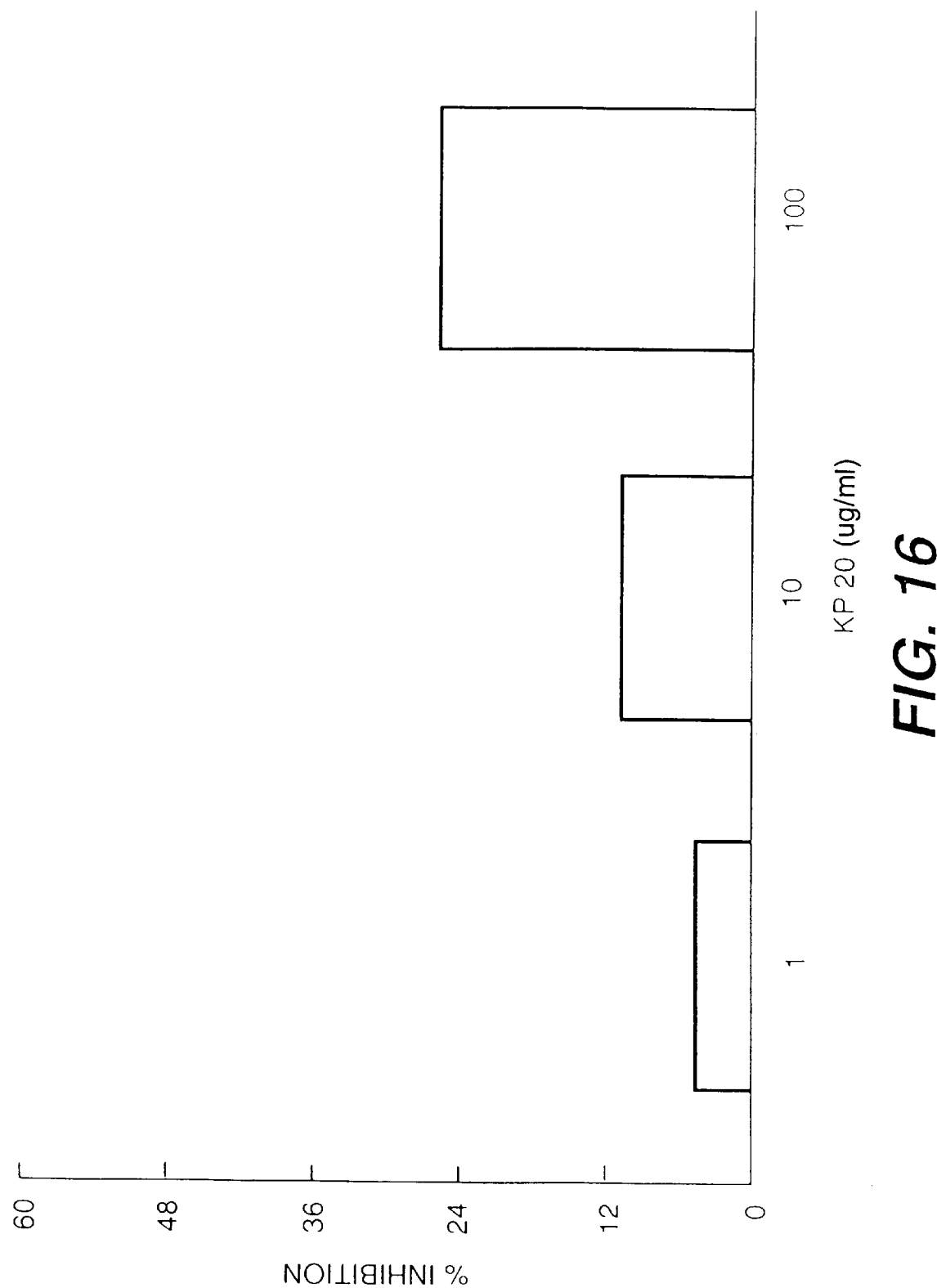
FIG. 16: Inhibition by KP-20 of IL-9 mediated MO7e proliferation.
Figure 17:
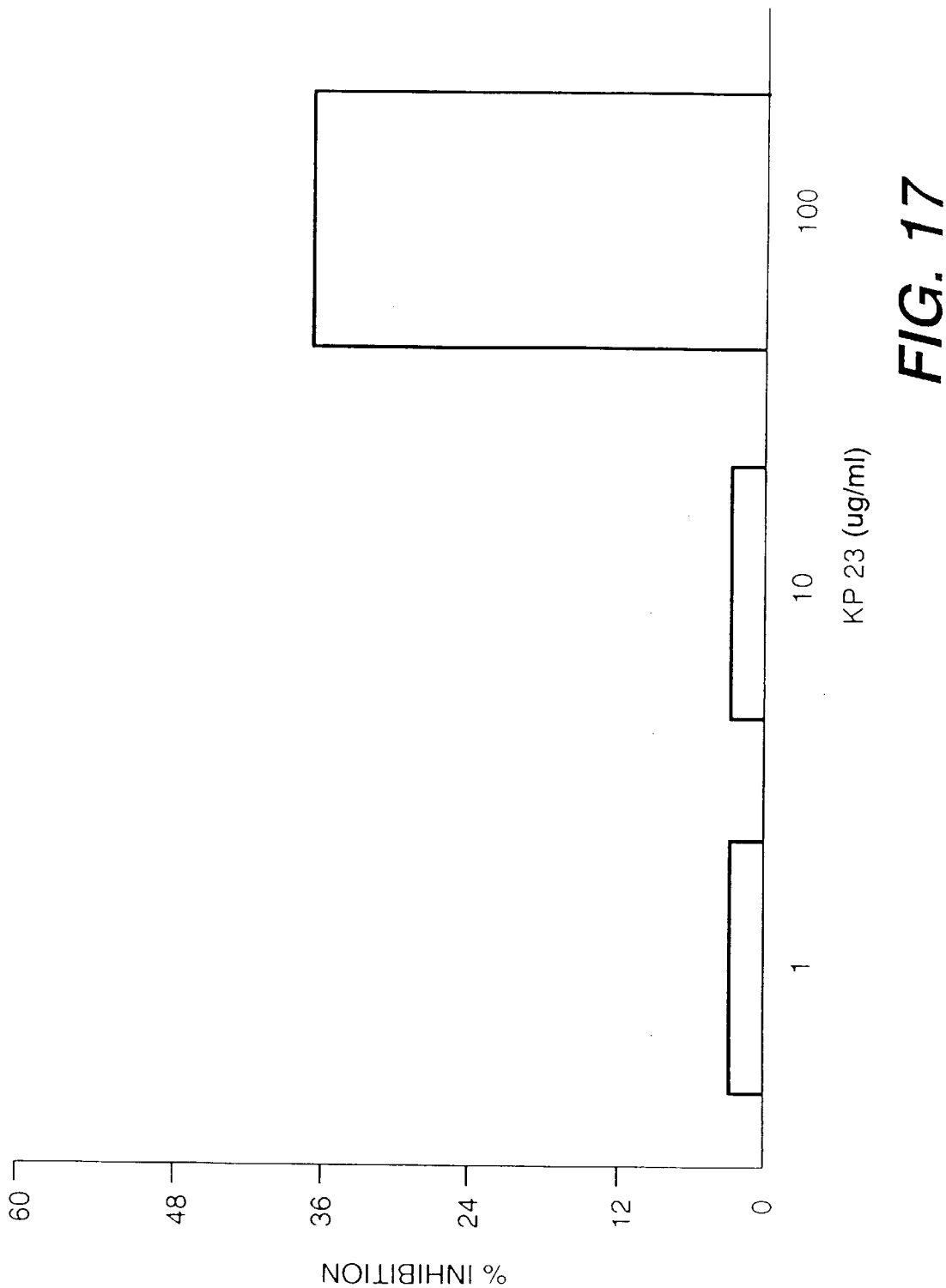
FIG. 17: Inhibition by KP-23 of IL-9 mediated MO7e proliferation.

FIG. 14 illustrates the amino acid sequence of three peptide antagonists of IL-9 function. Each peptide was incubated with MO7e cells and inhibition of cellular growth induced by IL-9 was determined by comparison with control conditions (no peptide)(see FIGS. 15–17). There was no evidence for cytotoxicity with any of the peptides. Peptides KP-16 and KP-20 are predicted to lie within two anti-parallel alpha-helicies and define a critical IL-9 receptor binding domain for the IL-9 ligand. The protein polymorphism at codon 117 lies within KP-23 and KP-24 which also exhibited antagonistic properties, further demonstrating the importance of this region surrounding the site of genetic variation.

Figure 18:
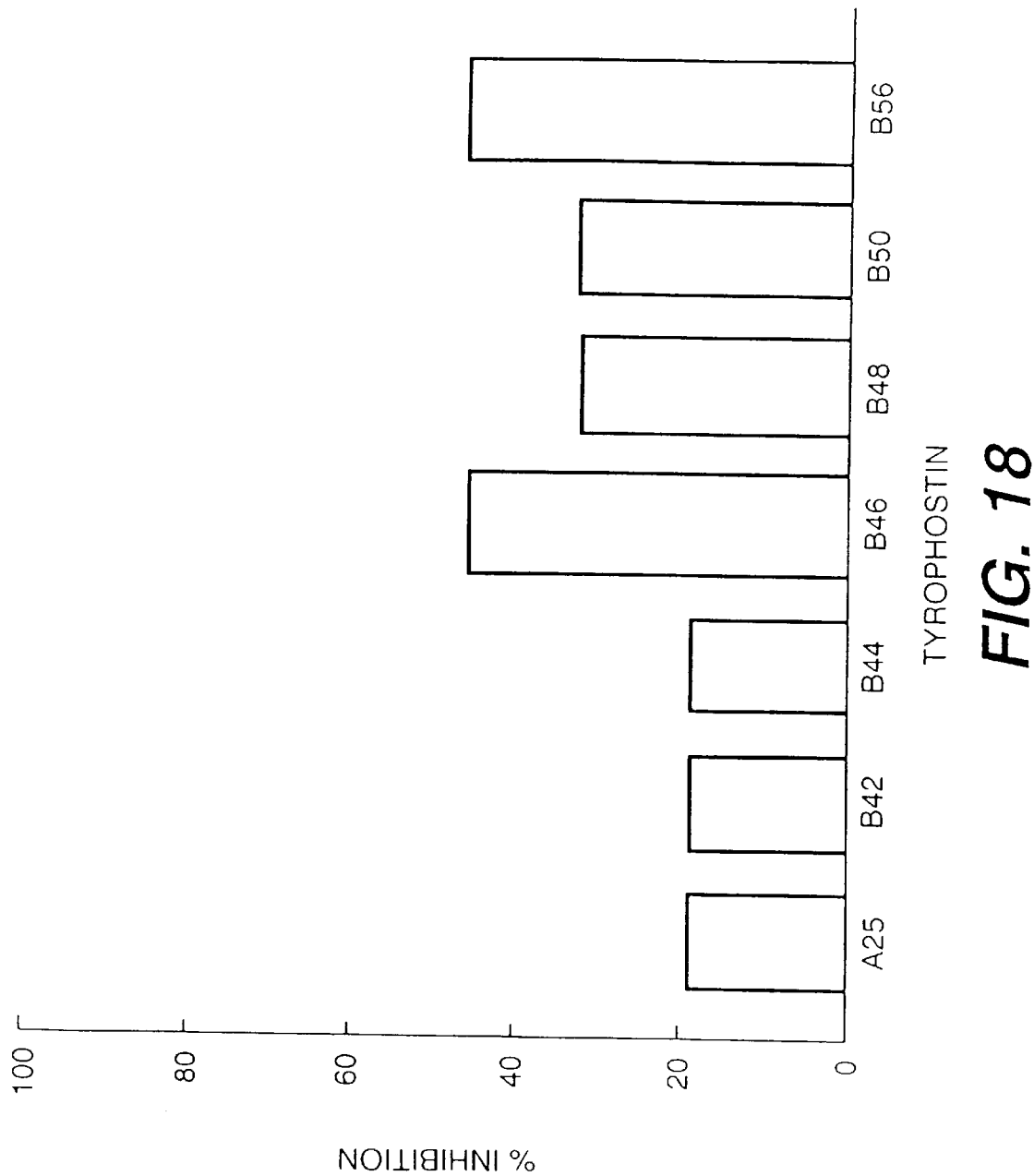
FIG. 18: Inhibition by various tyrophostins of IL-9 mediated MO7e proliferation.

FIG. 18 illustrates the effect of tyrophostins (obtained from Calbiochem) on the IL-9 dependent growth of MO7e cell in vitro. Each tyrophostin was incubated with MO7e cells and inhibition of cellular growth induced by IL-9 was determined by comparison with control conditions (no treatment). There was no evidence for cytotoxicity with any of the treatments. Tyrophostins B46 and B56 provided the greatest inhibition suggesting a common structure activity relationship.

Figure 19:
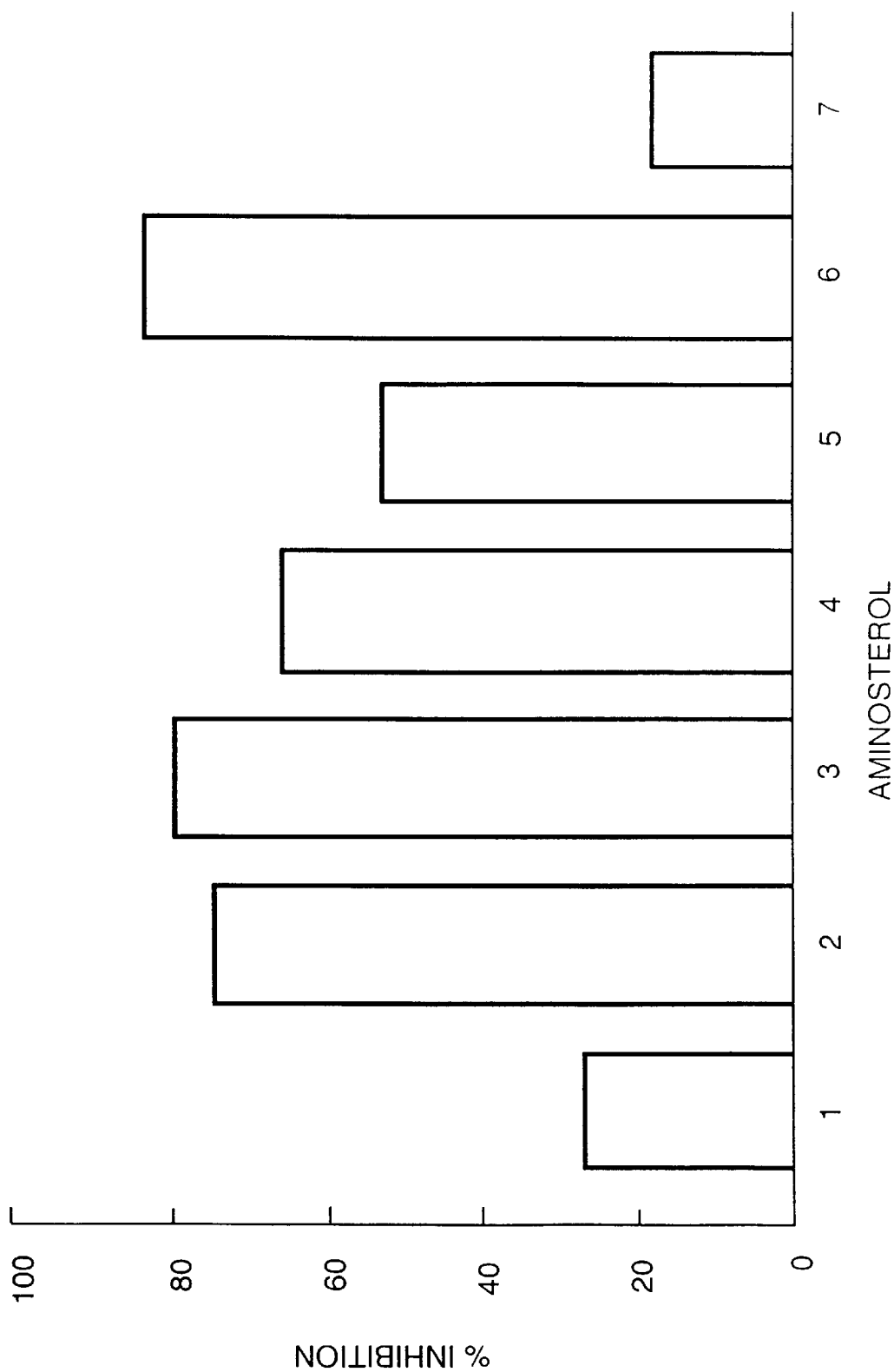
FIG. 19: Inhibition by various aminosterols of IL-9 mediated MO7e proliferation.

FIG. 19 illustrates the effect of aminosterols isolated from the shark liver as set forth in U.S. Ser. Nos. 08/290,826, 08/416,883, 08/478,763, and/or 08/483,059, incorporated herein by reference on the IL-9 dependent growth of MO7e cell in vitro. Each aminosterol was incubated with MO7e cells at 20 μg/ml of the culture media and inhibition of cellular growth induced by IL-9 was determined by comparison with control conditions (no treatment). There was no evidence for cytotoxicity with any of the treatments. Aminosterols 3 and 6 consistently provided the greatest inhibition of growth.

EXAMPLE 10

Assay for Proliferation of IgE Secreting Cells

B cell lines can be used to assess the function of rIL-9 and recombinant mutant forms of these proteins as well as other IL-9 antagonists. The proliferation of IgE secreting cells is measured for rIL-9 and compared to other cytokines or variant forms of rIL-9. In addition, compounds are tested for their ability to antagonize the baseline proliferative response of IgE secreting cells to rIL-9. Once a baseline IgE response is established for a cytokine, a statistically significant ($P<0.05$) loss of response in assays repeated three times in triplicate is considered evidence for antagonism. A true antagonistic response is differentiated from cellular toxicity by trypan blue staining (a technique well known to one of normal skill in the art).

Cell Preparation and Cultures

Peripheral blood lymphocytes (PBL) are isolated from heparinized blood of healthy donors or by mincing the spleens of mice. Mononuclear cells are separated by centrifugation on Ficoll/Hypaque (Pharmacia, Uppsala, Sweden) gradients. Semi-purified human B lymphocytes are obtained by resetting with neuraminidase (Behring, Marburg, FRG)—treated sheep red blood cells and plastic adherence for 1 hour at 37° C. B cells are also purified using paramagnetic separation with anti-CD20 coated magnetic beads (DYNAL) according to the manufacturer's recommendations.

The relative proportion of B cells, T cells and monocytes is determined by flow cytometry using monoclonal antibodies specific for CD23, CD3 and CD14, respectively (Becton Dickinson, Mountain View, Calif.). Briefly, $10^6$ cells/ml are incubated with a 1:1000 dilution of phycoerythrin conjugated anti-CD23 and fluorescein-conjugated anti-CD3 and anti-CD14 antibodies for 30 minutes at 4° C. After 3 spin washes with sterile PBS and 1% bovine serum albumin (Sigma) fluorescence is measured with a cytofluorograph (FACSTAR Plus, Becton Dickinson, Grenoble, France). Typically, there are 45% CD20+, 35% CD3+ and 10% CD14+ cells in a count of 5000 cells per sample.

Cells are cultured at a density of $2\times10^6$ cells/ml RPM1 1640 supplemented with 10% heat-inactivated fetal calf serum (FCS), 2 mM glutamine, 100 U/ml penicillin, 100 μg/ml streptomycin and 20 mM HEPES (RPM1-FCS) at 37° C. under a 5% CO2/95% air humidified atmosphere. Cultures are incubated with increasing concentrations of IL-4, rhIL-9, rmIL-9, or recombinant mutant forms of these proteins, alone, or in combination. Competition experiments are run with mixtures of one or more of these recombinant molecules or other IL-9 antagonists. The cultures are maintained for 9–13 days.

Frequency of IgE-Secreting B Cells

The frequency of IgE-secreting human B cells in response to human or murine IL-9 is determined using an ELISA-spot assay (Dugas et al., 1993, Eur J Immunol 23:1687–1692; Renz, H. et al., 1990. J. Immunology. 145:3641. Nitrocellulose flat-bottomed 96-well plates are coated overnight at 4° C. with purified goat antihuman IgE mAb diluted in 0.1 M NaHCO3 buffer (2.5 μg/ml). After one PBS-Tween 20 wash, plates are incubated for 1 hour with RPMI-FCS to saturate nonspecific binding sites. B cells obtained after 9–13 days of culture are collected, washed thrice and resuspended at $10^5$ cells/ml RPMI-FCS, then transferred onto the anti-IgE-coated plates followed by an 18 hour incubation at 37° C. A peroxidase-conjugated mouse anti-human IgE mab at various dilutions is added for 2 hours at 37° C. after washing. Spots are visualized after addition of diamino-benzidine diluted in 0.1 M Tris-HCl containing 0.03% $H_2O_2$. After 24 hours spots are counted with an inverted microscope at 25× magnification. Data are expressed as the number of IgE-secreting cells per $10^6$ cells.

EXAMPLE 11

ELISA for IgE Secreted by Cells Co-Stimulated with IL-9

Cells are isolated, prepared and stimulated as described above in Example 10. Flat bottom microtiter plates (Nunc)

are coated with rabbit anti-human IgE (1:2000, final dilution; Serotec, Oxford, GB), in 200 µl of 10 mM bicarbonate buffer (pH 9.6). After overnight incubation at 4° C., the plates are washed four times with phosphate-buffered saline (PBS) containing 0.05% Tween (PBS-Tween; Merck, Hohenbrunn, FRG) and are incubated for 1 h at room temperature with RPMI-FCS to saturate nonspecific protein-binding sites. After washing, 200 µl serial dilutions of human IgE (Eurobio, Les Ulis, France), standards in PBS-Tween are added to the respective plates to establish calibration curves. Dilutions of culture supernatants to be tested are then added and, after 2 h at room temperature, the plates are washed and 200 µl of diluted specific alkaline phosphatase-conjugated anti-IgE (1:250; Serotec), anti-IgG or anti-IgM (Behring) is added in the appropriate plates. After 2 h at room temperature, the plates are washed and 200 µl (0.5 mg/ml) p-nitrophenylphosphate (Sigma) in citrate buffer is added. Plates are incubated at 37° C., and absorbance (A) is measured at 405 nm using an autoreader (Dynatech Laboratories Inc, Chantilly, Va.). The threshold sensitivities of the assays are 100 pg/ml for IgE, 1 ng/ml for IgG, and 2 ng/ml for IgM and the variation between duplicate determinations of samples typically does not exceed 10%.

EXAMPLE 12

The Role of IL-9 in Murine Models of Asthma:

The Airway Response of Unsensitized Animals

Animals

Certified virus-free male mice ranging in age from 5 to 6 weeks were obtained from the Jackson Laboratory (Bar Harbor, Me.). Animals were housed in high-efficiency particulate filtered air (HEPA) laminar flow hoods in a virus and antigen free facility and allowed free access to pelleted rodent chow and water for 3 to 7 days prior to experimental manipulation. The animal facilities were maintained at 22° C. and the light:dark cycle was automatically controlled (10:14 h light:dark). Male and female DBA/2 (D2), C57BL/6 (B6), and (B6D2)F1 (F1) mice 5 to 6 weeks of age were purchased from the Jackson Laboratory, Bar Harbor, Me., or the National Cancer Institute, Frederick, Md. B×D mice were purchased from the Jackson Laboratory, Bar Harbor, Me. Food and water were present ad libitum.

Phenotyping and Efficacy of Pretreatment

To determine the bronchoconstrictor response, respiratory system pressure was measured at the trachea and recorded before and during exposure to the drug. Mice were anesthetized and instrumented as previously described. (Levitt R C, and Mitzner W, FASEB J 2:2605–2608 (1988); Levitt R C, and Mitzner W, J Appl Physiol 67(3): 1125–1132 (1989); Kleeberger S, Bassett D, Jakab G J, and Levitt R C, Am J Physiol 258(2)L313–320 (1990); Levitt R C; Pharmacogenetics 1:94–97 (1991); Levitt R C, and Ewart S L; Am J of Respir Crit Care Med 151:1537–1542(1995); Ewart S, Levitt R C, and Mitzner W, In press, J Appl Phys (1995). Airway responsiveness was measured to one or more of the following: 5-hydroxytryptamine (5HT) (sigma). An additional branch construction that can be used is acetylcholine (sigma), atracurium (Glaxo welcome). A simple and repeatable measure of the change in Ppi following bronchoconstrictor challenge was used and which has been termed the Airway Pressure Time Index (APTI) (Levitt R C, and Mitzner W, FASEB J 2:2605–2608 (1988); Levitt R C, and Mitzner W, J Appl Physiol 67(3): 1125–1132 (1989). The APTI was assessed by the change in peak inspiratory pressure (Ppi) integrated from the time of injection till the peak pressure returned to baseline or plateaued. The APTI was comparable to airway resistance (Rrs), however, the APTI includes an additional component related to the recovery from bronchoconstriction.

The strain distribution of bronchial responsiveness was identified in multiple inbred mouse strains in previous studies (Levitt R C, and Mitzner W, FASEB J 2:2605–2608 (1988); Levitt R C, and Mitzner W, J Appl Physiol 67(3): 1125–1132 (1989). The Rrs and/or APTI was determined in A/J, C3H/HeJ, DBA/2J, C57BL/6J mice.

Prior to sacrifice whole blood was collected for serum IgE measurements by needle puncture of the inferior vena cava in completely anesthetized animals. The samples were spun to separate cells and serum was collected and used to measure total IgE levels. Samples not measured immediately were frozen at −20° C.

Bronchoalveolar lavage and cellular analyses was preformed as described elsewhere (Kleeberger et al., 1990).

All IgE serum samples were measured using an ELISA antibody-sandwich assay. Microtiter plates (Corning #2585096, Corning, N.Y.) were coated, 50 µl per well, with rat anti-mouse IgE antibody (Southern Biotechnology #1130-01, Birmingham, Ala.) at a concentration of 2.5 µg/ml in coating buffer of sodium carbonate-sodium bicarbonate with sodium azide (Sigma #S-7795, #S-6014 and #S-8032, St Louis, Mo.). Plates were covered with plastic wrap and incubated at 4° C. for 16 hours. The plates were washed three times with a wash buffer of 0.05% Tween-20 (Sigma #P-7949) in phosphate-buffered saline (BioFluids #313, Rockville, Md.), incubating for five minutes for each wash. Blocking of nonspecific binding sites was accomplished by adding 200 µl per well 5% bovine serum albumin (Sigma #A-7888) in PBS, covering with plastic wrap and incubating for 2 hours at 37° C. After washing three times with wash buffer, duplicate 50 µl test samples were added to the wells. Test samples were assayed after being diluted 1:10, 1:50, and 1:100 with 5% BSA in wash buffer. In addition to the test samples a set of IgE standards (PharMingen #03121D, San Diego, Calif.) at concentrations from 0.8 ng/ml to 200 ng/ml in 5% BSA in wash buffer were assayed to generate a standard curve. A blank of no sample or standard was used to zero the plate reader (background). After adding samples and standards, the plate was covered with plastic wrap and incubated for 2 hours at room temperature. After washing three times with wash buffer, 50 ul of second antibody rat anti-mouse IgE-horseradish peroxidase conjugate (PharMingen #02137E) was added at a concentration of 250 ng/ml in 5% BSA in wash buffer. The plate was covered with plastic wrap and incubated 2 hours at room temperature. After washing three times with wash buffer, 100 ul of the substrate 0.5 mg/ml O-phenylaminediamine (Sigma #P-1526) in 0.1 M citrate buffer (Sigma #C-8532) was added to every well. After 5–10 minutes the reaction was stopped with 50 µl of 12.5% $H_2SO_4$, (VWR #3370-4, Bridgeport, N.J.) and absorbance was measured at 490 nm on a Dynatech MR-5000 plate reader (Chantilly, Va.). A standard curve was constructed from the standard IgE concentrations with antigen concentration on the x axis (log scale) and absorbance on the y-axis (linear scale). The concentration of IgE in the samples was interpolated from the standard curve.

EXAMPLE 13

The Role of IL-9 in Murine Models of Asthma:

The Airway Response of Sensitized Animals

Animals, Phenotyping, and Optimization of Antigen Sensitization

Animals and handling were essentially as described in Example 12. Sensitization with turkey egg albumin (OVA)

and aerosol challenge was carried out to assess the effect on BHR, BAL, and serum IgE. OVA was injected I.P. (25 µg) day 0 prior to OVA or saline aerosolization. Mice were challenged with OVA or saline aerosolization which was given once daily for 5 to 7 days starting on either day 13 or 14. Phenotypic measurements of serum IgE, BAL, and BHR was carried out on day 21. The effect of a 7 day OVA aerosol exposure on bronchoconstrictor challenge with 5-HT and acetylcholine were evaluated along with serum total IgE, BAL total cell counts and differential cell counts, and bronchial responsiveness. The effect of antibody (Ab) or saline pretreatment on saline aerosol or OVA aerosol induced lung inflammation was examined by measuring BHR, BAL, and serum IgE. Ab were administered I.P. 2–3 days prior to aerosolization of saline or OVA.

Lung histology was carried out after the lungs are removed during deep anesthesia. Since prior instrumentation may introduce artifact, separate animals were used for these studies. Thus, a small group of animals was treated in parallel exactly the same as the cohort undergoing various pretreatments except these animals were not used for other tests aside from bronchial responsiveness testing. After bronchial responsiveness testing, the lungs were removed and submersed in liquid nitrogen. Cryosectioning and histologic examination were carried out in a routine fashion.

Polyclonal neutralizing antibodies for murine IL-9 were purchased from R & D systems, Minneapolis, Minn. and blocking antibodies for murine IL-9 receptor were produced for Magainin Pharmaceuticals Inc. by Lampine Biological Labatories, Ottsville, Pa. using peptide conjugates produced at Magainin. The polyclonal antisera were prepared in rabbits against peptide sequences from the murine IL-9 receptor. The peptides used to produce the antisera were: GGQKAGAFTC (residues 1–10)(SEQ ID NO:19); LSN-SIYRIDCHWSAPELGQESR (residues 11–32)(SEQ ID NO:20); and CESYEDKTEGEYYKSHWSEWS (residues 184–203 with a Cys residue added to the N-terminus for coupling the peptide to the carrier protein)(SEQ ID NO:21). The antisera were generated using techniques described in *Protocols in Immunology*, Chapter 9, Wiley. Briefly, the peptides were coupled to the carrier protein, Keyhole Limpet, hemocyanin,(Sigma) through the side chain of the Cys residue using the bifunctional cross-linking agent MBS (Pierce). Peptide conjugates were used to immunize rabbits with appropriate adjuvents and useful antisera was obtained after several booster injections of the peptide conjugate. The antibodies were used therapeutically to down regulate the functions of IL-9 and assess the importance of this pathway to baseline lung responsiveness, serum IgE, and BAL in the unsensitized mouse. After Ab pretreatment on baseline BHR, BAL, and serum IgE levels relative to controls was determined. In additional experiments, recombinant human and murine IL-9 were administered I.P. 1 day before and daily during antigen sensitization (days 13–18). The animals were then phenotyped as described.

Figure 20:
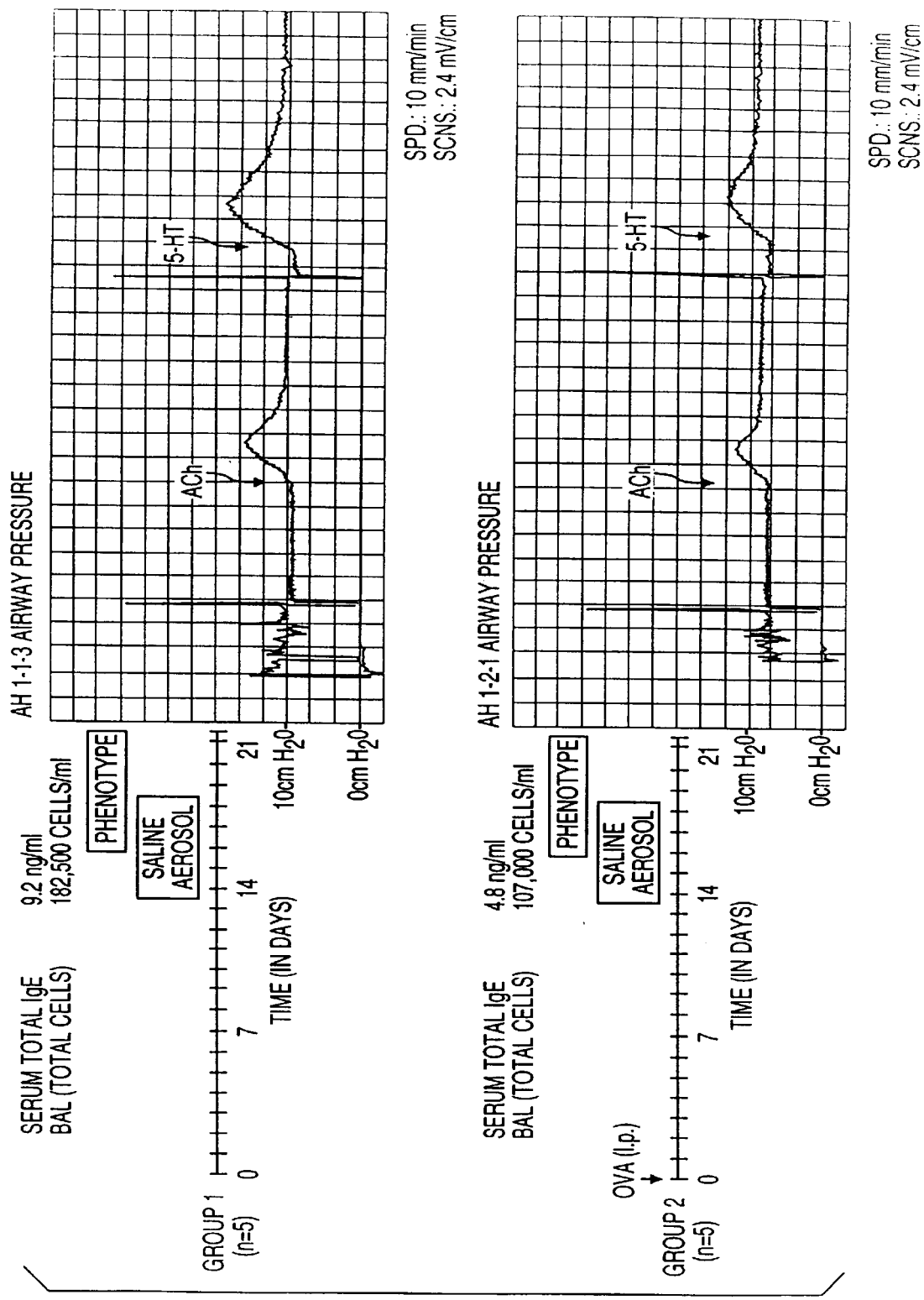
FIG. 20: Characterization of the role of IL-9 in the antigen response in vivo.
Figure 20:
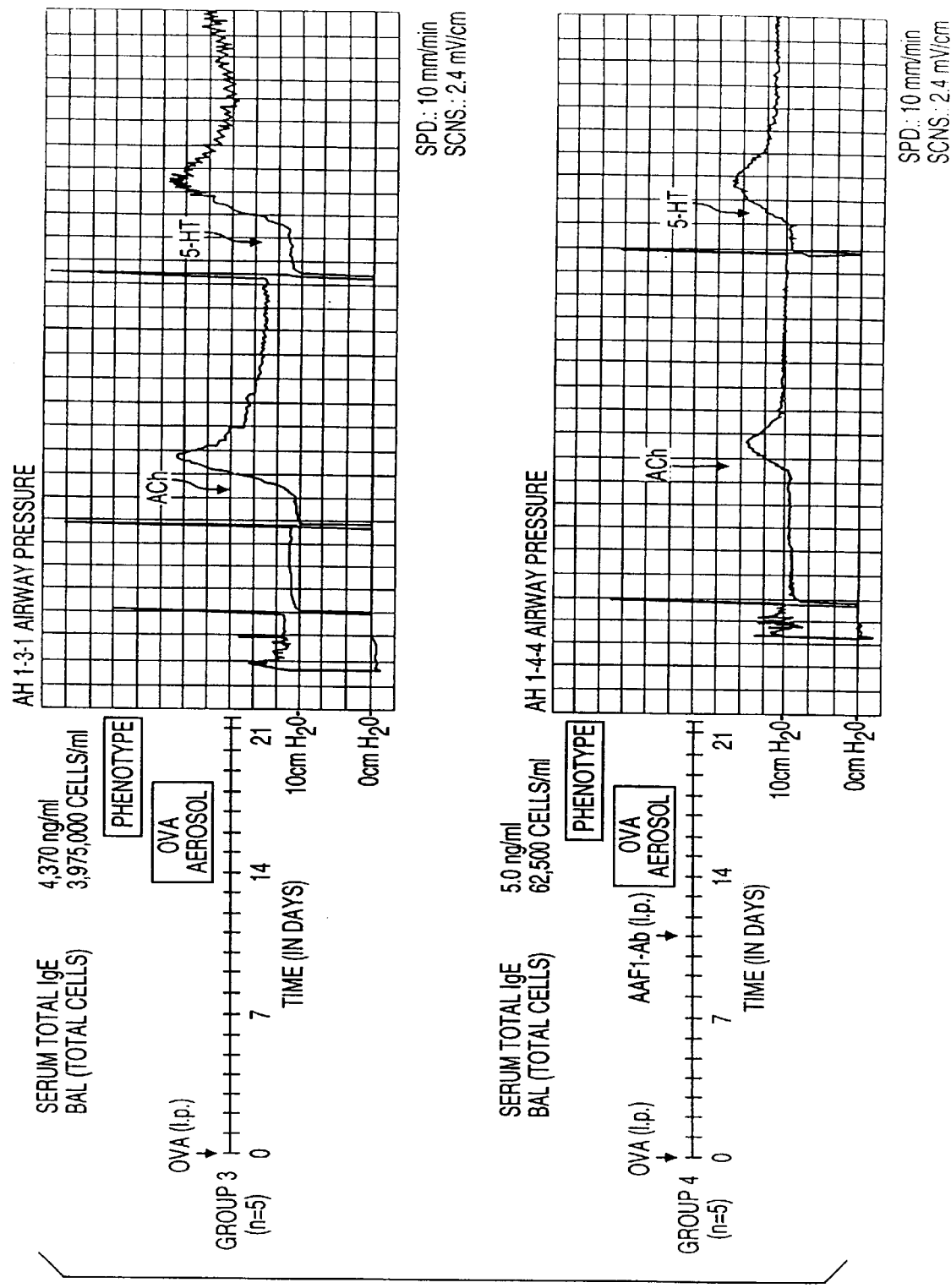

The phenotypic response of a representative animal treated with saline I.P. on day zero and challenged on days 14–20 with saline (as described in Example 12) is shown in FIG. 20 panel 1 (top). Baseline (control) serum total IgE was 9.2 ng/ml. Bronchoalveolar lavage (BAL) total cell counts showed 182,500 cells per milliliter of BAL. These animals did not demonstrate bronchial hyperresponsiveness when compared to historical controls (Levitt R C, and Mitzner W, J Appl Physiol 67(3): 1125–1132;1989).

FIG. 20 panel 2 (top middle) shows a representative animal from a group presensitized with OVA I.P on day zero and challenged with saline on days 14–20. These animals did not differ in their response to bronchoconstrictor, serum IgE, or BAL cell counts from the unsensitized mice (FIG. 7 top panel).

FIG. 20 panel 3 (bottom middle) shows a representative animal from those presensitized with OVA I.P on day zero and challenged with antigen (OVA) on days 14–20. These animals developed bronchial hyperresponsiveness (approximately two to three-fold over controls), elevated serum IgE (nearly one thousand-fold over controls), and increased numbers of inflammatory cells in the airway as demonstrated by elevated BAL cell counts (approximately thirty-fold) as compared to controls (FIG. 20 top 2 panels). Most of the cells recruited to the airway as a result of this antigen challenge were eosinophils.

FIG. 20 panel 4 (bottom) shows a representative animal from those presensitized with OVA I.P on day zero, pretreated with polyclonal neutralizing antibodies for murine IL-9 (approximately 200 µg/mouse I.P. in 0.5 ml of PBS), and challenged with antigen (OVA) on days 14–20. These animals were protected from the response to antigen. They did not differ significantly in their bronchial responsiveness, serum IgE, or BAL cell counts from controls (FIG. 20 top 2 panels).

Figure 21:
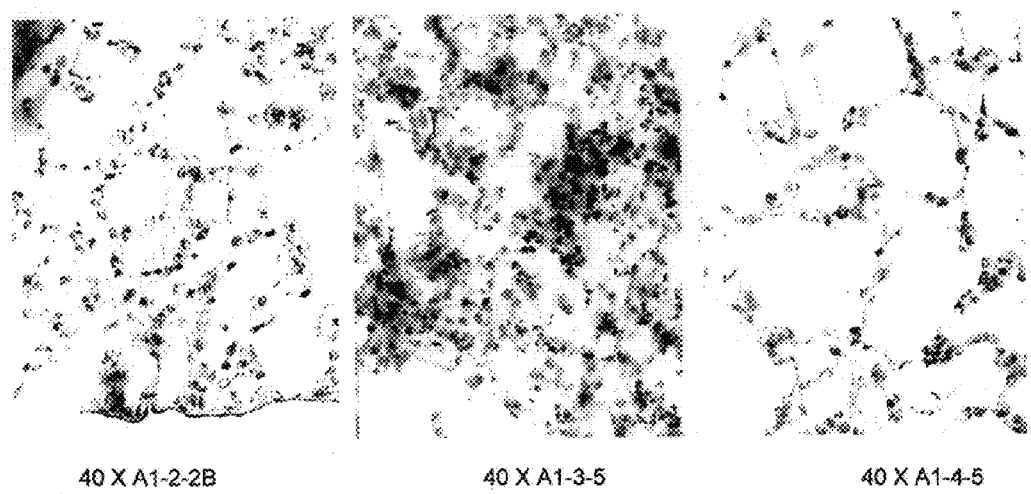
FIG. 21: Histologic examination of lungs from control, ova challenged, and anti-IL-9 pretreated animals.

FIG. 21 illustrates the effect of antigen challenge to OVA (as described above) with and without pretreatment with polyclonal neutralizing antibodies to murine IL-9 I.P. three days prior in representative animals. The left figure (A1-2-1B) is a histologic section from the lungs of control animals (sensitized to OVA but exposed only to a saline aerosol challenge). The middle figure (A1-3-5) is a histologic section from the lungs of animals sensitized to OVA and exposed to an OVA aerosol challenge. The right figure (A1-4-5) is a histologic section from the lungs of animals sensitized to OVA and exposed to an OVA aerosol challenge who were pretreated three days prior with polyclonal neutralizing antibodies to murine IL-9. Pretreatment with neutralizing antibody produced histological confirmation of complete protection from antigen challenge.

Figure 22:
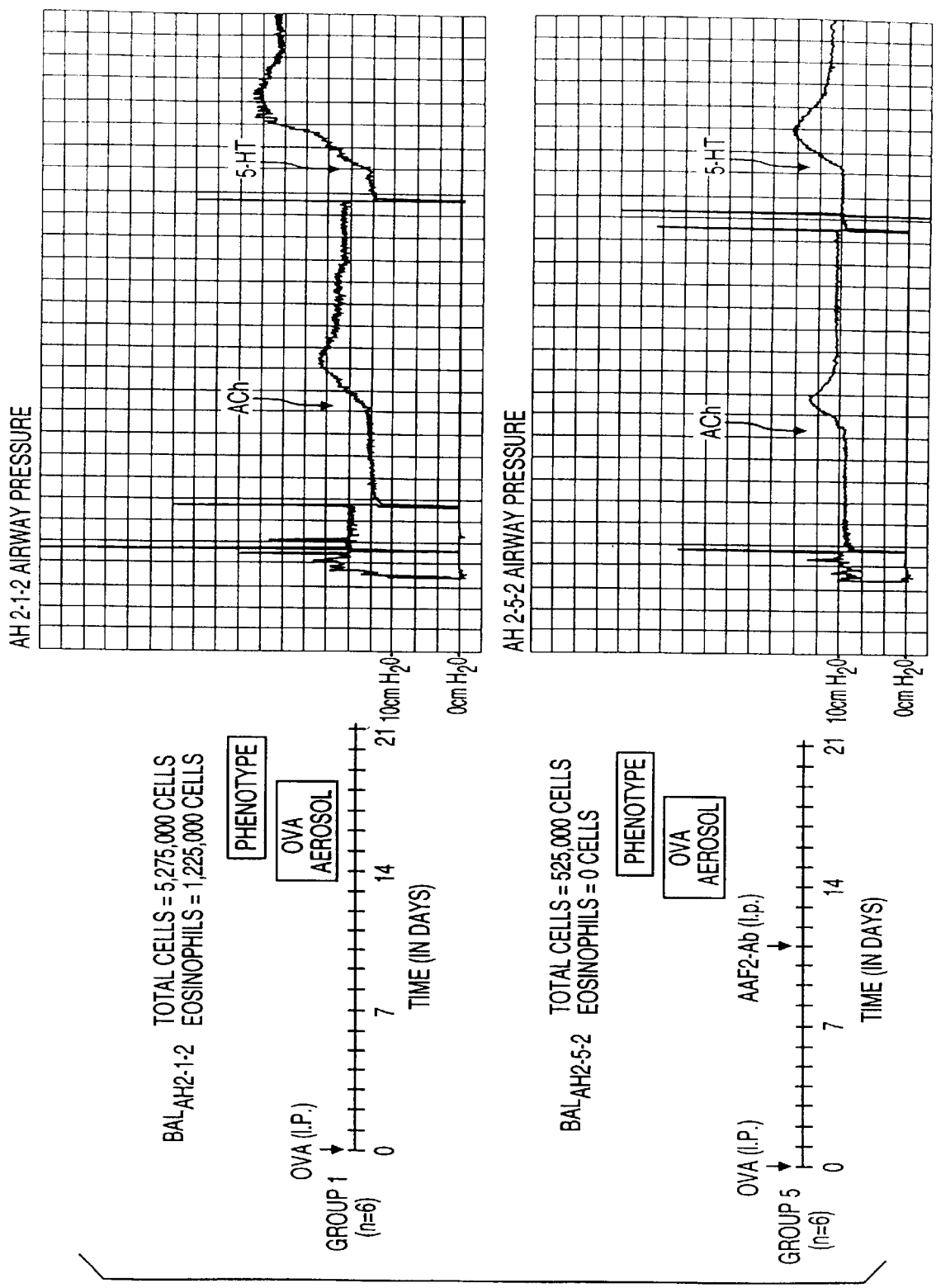
FIG. 22: Inhibition of the antigen response in vivo by blocking antibodies to the murine IL-9 receptor.
Figure 23:
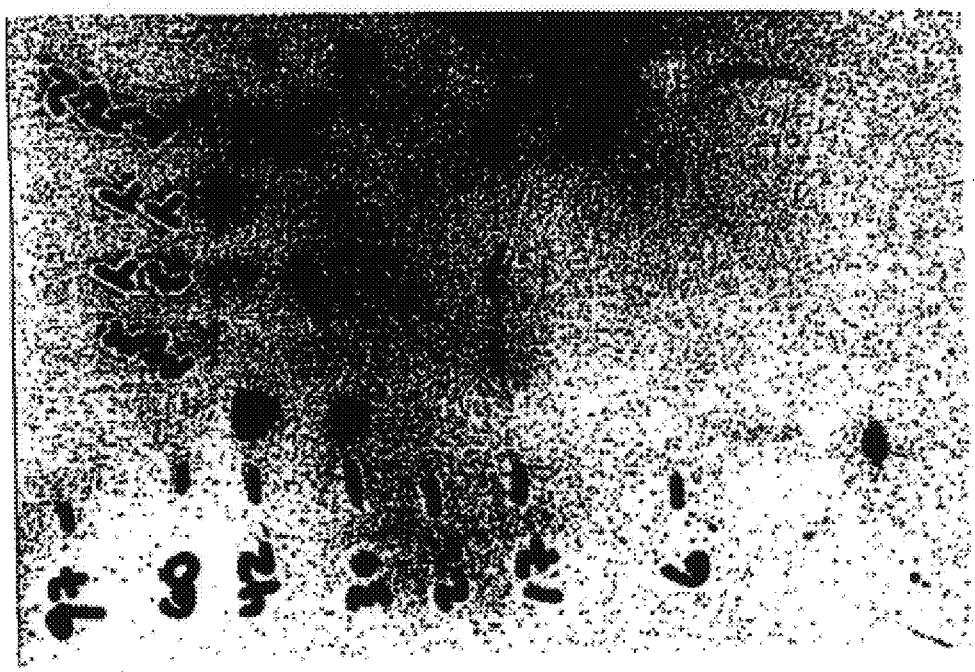
FIG. 23: Expression of human Met117 IL-9 and Thr117 IL-9.

FIG. 22 panel 1 (top) shows a representative animal from mice presensitized with OVA I.P on day zero and challenged with antigen (OVA) on days 13–18. These animals developed bronchial hyperresponsiveness (approximately two to three-fold over controls), and increased numbers of inflammatory cells including eosindhils in the airways as demonstrated by elevated BAL cell counts as compared to controls (FIG. 20 top 2 panels). Many of the cells recruited to the airway as a result of this antigen challenge were eosinophils.

FIG. 22 panel 2 (bottom) shows a representative animal from those presensitized with OVA I.P on day zero, pretreated with polyclonal neutralizing antibodies to the murine IL-9 receptor (approximately 1 mg/mouse I.P. in 0.5 ml of PBS), and challenged with antigen (OVA) on days 13–18. This representative animal was protected from the response to antigen. This response did not differ significantly bronchial responsiveness, BAL cell counts from controls (FIG. 20 top 2 panels). These data demonstrate the potential effectiveness of treating atopic allergy with antibodies to the IL-9 receptor.

EXAMPLE 14

Murine Spleen Isolation and Culture

Mice were anesthetized and spleens were removed aseptically. Spleens were minced with scissors and gently passed through a wire mesh (autoclaved) [#60 sieve]. Cells were resuspended in 40 mls of RPMI-1640 [GIBCO, BRL, Rockville, Md.], and spun for 5 min. at 250×G twice. The pellet was resuspended in 10 mls of lysing butter to remove RBCs [4.15 gm NH4Cl, 0.5 gm KHCO3; 019 g EDTA to 500 mls with ddH20]. Cells were incubated for about 5 minutes at 37° C. and 40 mls of [RPMI-FCS (RPMI-1640, 10% AFBS, 50 µM BME 2mM glutamine, containing penicillin and streptomycin]. These cells were spun again for 5 minutes at 250× G and resuspended in 20 mls RPMI-FCS with or without 5 µg/ml of concanavalin A [Sigma #C5275]. IL-9 was assessed at 48 hours in untreated splenocytes and after concanavalin A stimulation from DBA/2J (D2) and C57BL/6J (B6) mice. IL-9 was amplified by RT-PCR (as set forth in Example 6), and probed with an IL-9 specific murine probe after Southern transfer. Southern blots were performed by "standard" techniques. Briefly, RT-PCR products were electrophoresed in 2% agarose gels. Gels were stained with ethidium bromide and photographed with a ruler to determine molecular weight of DNA in southern blot. Gels were then soaked in 0.5 N NaOH for 30 minutes and neutralized in 0.5M Tris, pH 7.0 for 30 minutes. DNA was transferred to zetaprobe (BioRAD) nylon membrane by capillary transfer in 20× SSC overnight. The next day, the membrane was air dried, baked at 80° C. for 15 minutes and prehybridized in 6× SSC and 0.1w SDS for 1 hour at 42° C. A kinase end-labelled p32 oligonucleotide probe (5'-AATTACCTTATTGAAAATCTGAAG-3') was added to the hybridization solution plus 0.1 mg/ml sheared salmon sperm DNA and incubated overnight at 42° C. The next day, the filter was washed in 3× SSC and 0.1% SDS at 37° C. for 30 minutes, and the filter was exposed to film for 1 hour. FIG. 26 illustrates steady state levels of IL-9 after 48 hours from each strain of mice. IL-9 was observed in unstimulated D2 (D2−) splenocytes, whereas no IL-9 was detectable in B6 (B6−) mice. While there was a significant increase of IL-9 after concanavalin A stimulation in D2 (D2+) splenocytes, there was no detectable It-9 in B6 (B6+) mice despite concanavalin A treatment.

EXAMPLE 15

Expression of Human Met117 IL-9 and Thr117 IL-9 in PBMCs SDS-PAGE and Immunoblot Analysis After obtaining proteins isolated from human PBMC of healthy donors inhibiting either the wild type (Thr117) or Met117- IL-9 genotypes as set forth in Example 13, and SDS-PAGE was performed by the method of Laemmli (Laemmli U. K. (1970) Nature 227, 680–685) by using a 18% polyacrylamide gel in a mini-gel system (Xcell II vertical gel unit, Novex). For immunoblot analysis, the proteins separated by SDS-PAGE were transferred to nitrocellulose membranes by using the SD transblot transfer unit (Biorad) in 25 mM Tris-glycine buffer, pH 8.3, containing 15% methanol (Towbin H., et al., (1979) (Proc. Natl. Acad. Sci. U.S.A. 76, 4350–4354). The unoccupied binding cites on the membrane were blocked by incubating for 1 hour to overnight with 20 mM Tris-HCl buffer, pH 8.0, plus 0.05% tween 20 (TBST) containing 5% dry milk. The membranes were then incubated with 1:1000 dilution of goat anti-human IL-9 polyclonal antibody (R&D Systems) for 1 hour at room temperature. The membranes were washed with TBST and treated with 1:10,000 dilution of mouse anti-goat TgG conjugated with horseradish peroxidase for 1 hour. After washing with TBST, the bound antibodies were visualized by addition of the super signal substrate chemiluminescence system (Pierce).

Figure 24:
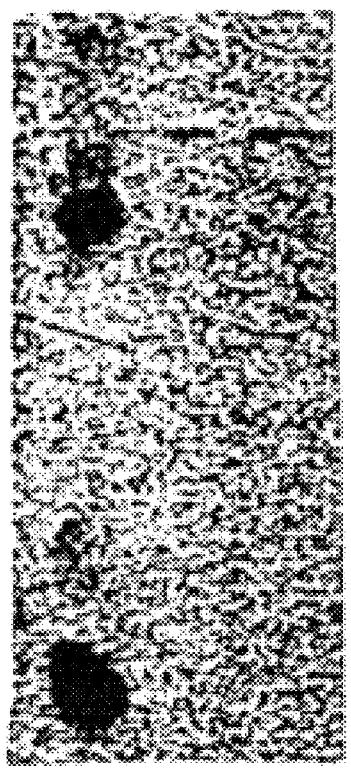
FIG. 24: Binding of the human recombinant Met117 and Thr117 forms of IL-9 to a soluble receptor.

FIG. 24 demonstrates the expression of human IL-9 proteins from cultured PBMCs 48 hours after mitogen stimulation in individuals whose genotypes have been determined by genomic analysis of the IL-9 gene. Lane 1 is molecular weight markers, lane 2 is a Met117 homozygote, lane 3 is a heterozygote Met117/Thr117, lane four is a Thr117 homozygote. A single product of the approximate expected size (14 kD) was seen in each individual PBMCs after mitogen stimulation. These data demonstrate that both forms of the IL-9 protein are expressed and stable at steady state.

While the invention has been described and illustrated herein by references to various specific materials, procedures and examples, it is understood that the invention is not restricted to the particular material combinations of material, and procedures selected for that purpose. Numerous variations of such details can be implied as will be appreciated by those skilled in the art.

REFERENCES

1. Gergen P J, and Weiss K B: The increasing problem of asthma in the United States. Am Rev Respir Dis 146:823–824, 1992.
2. Goodman and Gilman's The Pharmacologic Basis of Therapeutics, Seventh Edition, MacMillan Publishing Company, N.Y. USA, 1985.
3. Burrows B, Martinez F D, Halonen M, Barbee R A, and Cline M G: Association of asthma with serum IgE levels and skin-test reactivity to allergens. New Eng J Med 320:271–277, 1989.
4. Clifford R D, Pugsley A, Radford M, and Holgate S T: Symptoms, atopy, and bronchial response to methacholine in parents with asthma and their children. Arch Dis in Childhood 62:66–73, 1987.
5. Gergen P J: The association of allergen skin test reactivity and respiratory disease among whites in the U.S. population. Arch Intern Med 151:487–492, 1991.
6. Burrows B, Sears M R, Flannery E M, Herbison G P, and Holdaway M D: Relationship of bronchial responsiveness assessed by methacholine to serum IgE, lung function, symptoms, and diagnoses in 11-year-old New Zealand children. J Allergy Clin Immunol 90:376–385, 1992.
7. Johannson S G O, Bennich H H, and Berg T: The clinical significance of IgE. Prog Clin Immunol 1:1–25, 1972.
8. Sears M R, Burrows B, Flannery E M, Herbison G P, Hewitt C J, and Holdaway M D: Relation between airway responsiveness and serum IgE in children with asthma and in apparently normal children New Engl J Med 325(15):1067–1071, 1991.
9. Halonen M, Stern D, Taussig L M, Wright A, Ray C G, and Martinez F D: The predictive relationship between serum IgE levels at birth and subsequent incidences of lower respiratory illnesses and eczema in infants. Am Rev Respir Dis 146:666–670, 1992.
10. Marsh D G, Meyers D A, and Bias W B: The epidemiology and genetics of atopic allergy. New Eng J Med 305:1551–1559, 1982.
11. Hopp R J, Bewtra A K, Biven R, Nair N M, Townley R G. Bronchial reactivity pattern in nonasthmatic parents of asthmatics. Ann Allergy 1988;61:184–186.
12. Hopp R J, Townley R G, Biven R E, Bewtra A K, Nair N M. The presence of airway reactivity before the development of asthma. Am Rev Respir Dis 1990;141:2–8.
13. Ackerman V, Marini M, Vittori E, et al. Detection of cytokines and their cell sources in bronchial biopsy specimens from asthmatic patients: relationship to atopic status, symptoms, and level of airway hyperresponsiveness. Chest 1994;105:687–696.
14. Hamid G, Azzawi M, Ying S, et al. Expression of mRNA for interleukin-5 in mucosal bronchial biopsies from asthma. J Clin Invest 1991;87:1541–1546.

15. Djukanovic R, Roche W R, Wilson J W, et al. Mucosal inflammation in asthma. Am Rev Respir Dis 1990;142:434–57.
16. Robinson D S, Hamid Q, Ying S, et al. Predominant TH2-like bronchoalveolar T lymphocyte population in atopic asthma. N Engl J Med 1992;326:298–304.
17. Robinson D S, Hamid Q, Ying S, et al. Prednisolone treatment in asthma is associated with modulation of bronchoalveolar lavage cell interleukin-4, interleukin-5, and interferon-_cytokine gene expression. Am Rev Respir Dis 1993;148:401–406.
18. Robinson D S, Ying S, Bentley A, et al. Relationship among numbers of bronchoalveolar lavage cells expressing messenger ribonucleic acid for cytokines, asthma symptoms, and airway methacholine responsiveness in atopic asthma. J Allergy Clin Immunol 1993;92:397–403.
19. Sears M, Burrows B, Flannery E M, Herbison G P, Hewitt C J, Holdaway M D. Relation between airway responsiveness and serum IgE in children with asthma and in apparently normal children. N Engl J Med 1991;325:1067–1071.
20. Burrows B, Sears M R, Flannery E M, Herbison G P, Holdaway M D. Relationship of bronchial responsiveness assessed by methacholine to serum IgE, lung function, symptoms, and diagnoses in 11-year-old New Zealand children. J Allergy Clin Immunol 1992;90:376–385.
21. Clifford R D, Pugsley A, Radford M, Holgate S T. Symptoms, atopy, and bronchial response to methacholine in parents with asthma and their children. Arch Dis Childhood 1987;62:66–73.
22. O'Connor G T, Sparrow D, and Weiss S T: The role of allergy and nonspecific BHR in the pathogenesis of COPD. Am Rev Respir Dis 140:225–252, 1989.
23. Cogswell J J, Halliday D F, and Alexander J R: Respiratory infections in the first year of life in children at the risk of developing atopy. Brit Med J 284:1011–1013, 1982.
24. Boushey H A, Holtzman M J, Sheller J R, and Nadel J A: BHR. Am Rev Respir Dis 121:389–413, 1980.
25. Cookson W O C M, and Hopkin J M: Linkage between immunoglobin E responses underlying asthma and rhinitis and chromosome 11q. Lancet 1292–1295,1989.
26. Moffatt M F, Sharp P A, Faux J A, Young R P, Cookson W O C M, and Hopkins J M; Factors confounding genetic linkage between atopy and chromosome 11q. Clin Exp Allergy 22:1046–1051, 1992.
27. Amelung P, Panhuysen C, Postma D S, Levitt R C, Koeter G H, Francomano C, Bleeker E R, and Meyers D A: Atopy, asthma and bronchial hyperresponsiveness: Exclusion of linkage to markers on chromosome 11q and 6p. Clin Exper Allergy 22:1077–1084, 1992.
28. Rich S S, Roitman-Johnson B, Greenberg B, Roberts S, and Blumenthal M N: Genetic evidence of atopy in three large kindreds: no evidence of linkage to D11S97. Clin Exp Allergy 22:1070–1076, 1992.
29. Lympany P, Welsh K, MacCochrane G, Kemeny D M, and Lee T H: Genetic analysis using DNA polymorphism of the linkage between chromosome 11q13 and atopy and BHR to methacholine. J Allergy Clin Immunol 89:619–628, 1992a.
30. Lympany P, Welsh K I, Cochrane G M, Kemeny D M, and Lee T H: Genetic analysis of the linkage between chromosome 11q and atopy. Clin Exp Allergy 22:1085–1092, 1992b.
31. Hizawa N, Yamagushi E, Ohe M, Itoh A, Furuya K, Ohnuma N, and Kawakami Y: Lack of linkage between atopy and locus 11q13. Clinical and Experimental Allergy 22:1065–1069, 1992.
32. Sanford A J, Shirakawa T, Moffatt M F, Daniels S E, Ra C, Faux J A, Young R P, Nakamura Y, Lathrop G M, Cookson W O C M, and Hopkin J M: Localization of atopy and b subunit of high-affinity IgE receptor (FceR1) on chromosome 11q. Lancet 341:332–334, 1993.
33. Shirakawa T, Airong L, Dubowitz M, Dekker J W, Shaw A E, Faux J A, Ra C, Cookson W O C M, and Hopkin J M: Association between atopy and variants of the β subunit of the high-affinity immunoglobulin E receptor. Nature Genetics 7:125–130, 1994.
34. Marsh D G, Bias W B, and Ishizaka K: Genetic control of basal serum immunoglobulin E level and its effect on specific reaginic sensitivity. Proc Natl Acad Sci USA 71:3588–3592, 1974.
35. Gerrard J W, Rao D C, and Morton N E: A genetic study of IgE. Am J Hum Genet 30:46–58, 1978.
36. Meyers D A, Beaty T H, Freidhoff L R, and Marsh D G: Inheritance of serum IgE (basal levels) in man. Am J Hum Genet 41:51–62, 1987.
37. Meyers D A, Bias W B, and Marsh D G: A genetic study of total IgE levels in the Amish. Hum Hered 32:15–23, 1982.
38. Martinez F D, Holberg C J, Halonen M, Morgan W J, Wright A L, and Taussig L M: Evidence for mendelian inheritance of serum IgE levels in Hispanic and Non-hispanic white families. Am J Hum Genet 55:555–565, 1994.
39. Blumenthal M N, Namboordiri K K, Mendell N, Gleich G, Elston R C, and Yunis E: Genetic transmission of serum IgE levels. Am J Med Genet 10:219–228, 1981.
40. The Genome Data Base. The Welch Library, The Johns Hopkins Medical Institutions, Baltimore, Md., USA.
41. Marsh D G, Neely J D, Breazeale D R, et al. Linkage analysis of IL4 and other chromosome 5q31.1 markers and total serum immunoglobulin E concentrations. Science 1994;264:1152–1156.
42. Meyers D A, Postma D S, Panhuysen C I M, et al. Evidence for a locus regulating total serum IgE levels mapping to chromosome 5. Genomics 1994;23:464 470.41.
43. Doull, I., Lawrence, S., Watson, M., Begishvili, T., Beasley, R., Lampe, F., Holgate, S. T., Morton, N. E. Allelic association of makers on chromosome Sq and 11q with atopy and bronchial hyperresponsiveness. Am J Respir Crit Care Med, 1996;153:1280–1284.
44. Ott J. Analysis of human genetic linkage. Baltimore, Md.: The Johns Hopkins University Press, 1991.
45. Renauld, J-C, Houssiau, F, Druez, C. Interleukin-9. Int Rev Exp Pathology 1993;34A: 99–109.
46. Renauld, J-C, Kermouni, A, Vink, A, Louahed, J, Van Snick, J. Interleukin-9 and its receptor: involvement in mast cell differentiation and T cell oncogenesis. J Leukoc Biol 1995;57:353–360.
47. Hultner, L, Moeller, J, Schmitt, E, Jager, G, Reisbach, G, Ring, J. Dormer, P. Thiol-sensitive mast cell lines derived from mouse bone marrow respond to a mast cell growth-enhancing activity different from both IL-3 and IL-4. J Immunol 1989;142:3440–3446.
48. Dugas, B, Renauld, J-C, Pene, J, Bonnefoy, J, Peti-Frere, C, Braquet, P, Bousquet, J, Van Snick, J, Mencia-Huerta, J M. Interleukin-9 potentiates the interleukin-4-induced immunoglobulin [IgG, IgM and IgE] production by normal human B lymphocytes. Eur J Immunol 1993;23:1687–1692.
49. Petit-Frere, C, Dugas, B, Braquet, P, Mencia-Huerta, J M. Interleukin-9 potentiates the interleukin-4-induced IgE and IgG1 release from murine B lymphocytes. Immunology 1993;79:146–151.

50. Behnke, J M, Wahid, F N, Grencis, R K, Else, K J, Ben-Smith, A W, Goyal, P K. Immunological relationships during primary infection with Heligmosomoides polygyrus [Nematospiroides dubius]: downregulation of specific cytokine secretion [IL-9 and IL-10] correlates with poor mastocytosis and chronic survival of adult worms. Parasite Immunol 1993;15:415–421.

51. Gessner, A, Blum, H, Rollinghoff, M. Differential regulation of IL-9 expression after infection with Leischmania major in susceptible and resistant mice. Immunobiology 1993;189:419–435.

52. Renauld J-C, Druez C, Kermouni A, et al. Expression cloning of the murine and human interleukin 9 receptor cDNAs. Proc Natl Acad Sci 89:5690–5694(1992).

53. Chang M-S, Engel G, Benedict C et al. Isolation and characterization of the Human interleukin-9 receptor gene. Blood 83:3199–3205(1994).

54. Renauld J-C, Goethals A, Houssiau F, et al. Human P40/IL-9. Expression in activated CD4+T cells, Genomic Organization, and Comparison with the Mouse Gene. J Immunol 144:4235–4241(1990).

55. Kelleher K, Bean K, Clark S C, et al. Human interleukin-9: genomic sequence, chromosomal location, and sequences essential for its expression in human T-cell leukemia virus (HTLV-I-transformed human T cells. Blood 77:1436–1441(1991).

56. Houssiau F A, Schandene L, Stevens M, et al. A cascade of cytokines is responsible for IL-9 expression in human T cells. Involvement of IL-2, IL-4, and IL-10. J of Immunol. 154:2624–2630(1995).

57. Miyazawa K, Hendrie P C, Kim Y-J, et al. Recombinant human interleukin-9 induces protein tyrosine phosphorylation and synergizes with steel factor to stimulate proliferation of the human factor-dependent cell line, MO7e. Blood 80:1685–1692(1992).

58. Yin T, Tsang M L-S, Yang Y-C. JAK1 kinase forms complexes with interleukin-4 receptor and 4PS/insulin receptor substrate-1-like protein and is activated by interleukin-4 and interleukin-9 in T lymphocytes. J Biol Chem 269:26614–26617(1994).

59. Renauld J-C, Druez C, Kermouni A, et al. Expression cloning of the murine and human interleukin 9 receptor cDNAs. Proc Natl Acad Sci 89:5690–5694(1992).

60. Chang M-S, Engel G, Benedict C et al. Isolation and characterization of the Human interleukin-9 receptor gene. Blood 83:3199–3205(1994).

61. Kreitman R J, Puri R K, Leland P, et al. Site-specific conjugation to interleukin4 containing mutated cysteine residues produces interleukin 4-toxin conjugates with improved binding and activity. Biochemistry 33:11637–11644(1994)

62. Simoncsits A, Bristulf J, Tjornhammar M L, et al. Deletion mutants of human interleukin 1 beta significantly reduced agonist properties: search for the agonist/antagonist swi.tch in ligands to the interleukin 1 receptors. Cytokine 6:206–214(1994).

63. Zav'yalov V P, Navolotskaya E V, Isaev I S, et al. Nonapeptide corresponding to the sequence 27–35 of the mature human IL-2 efficiently competes with rIL-2 for binding to thymocyte receptors. Immunol Lett 31:285–288(1992).

64. Chu J W, and Sharom F J. Glycophorin A interacts with interleukin-2 and inhibits interleukin-2-dependent T-lymphocyte proliferation. Cell Immunol 145:223–239 (1992).

65. Alexander A G, Barnes N C, Kay A B. Trial of cyclosporin in corticosteroid-dependent chronic severe asthma. Lancet 339:324–328(1992).

66. Morely J. Cyclosporin A in asthma therapy: a pharmacological rationale. J Autoimmun 5 Suppl A:265–269 (1992).

67. Lander, E. S., Botstein, D. Mapping Mendelian factors underlying quantitative traits using RFLP linkage maps. Genetics 121, 185–199(1989).

68. Soller , M., Brody, T. On the power of experimental designs for the detection of linkage between maker loci and quantitative loci in crosses between inbred lines. Theor Appl Genet 47:35–39(1976).

69. Kvaloy K, Galvagni F, and Brown W R A. The sequence organization of the long arm pseudoautosomal region of the human sex chromosomes. Hum Mol Genet 3:771–778 (1994).

70. Freije D, Helms C, Watson M S, et al. Science 258:1784–1787(1992).

71. Weber J L, May P E. Abundant class of human DNA polymorphisms which can be typed using the polymerase chain reaction. Am J Human Genet 1989;44:388–396.

72. Saiki K K, Gelfand D H, Stoffel S, et al. Primer-directed enzymatic amplification of DNA with a thermostable DNA polymerase. Science 1988;239:487–491.

73. Sheffield V C, Beck J S, Kwitek A E, Sandstrom D W, and Stone E M: The sensitivity of single-strand conformation polymorphism analysis for the detection of single base substitutions. Genomics 16:325–332, 1993.

74. Orita M, Suzuki Y, Sekiya T, and Hayashi K: Rapid and sensitive detection of point mutations and DNA polymorphisms using the polymerase chain reaction. Genomics 5:874–9, 1989.

75. Sarkar G, Yoon H-S, and Sommer S S: Dideoxy fingeringprint (ddF): A rapid and efficient screen for the presence of mutations. Genomics 13:441–443, 1992.

76. Cotton R G: Detection of single base changes in nucleic acids. Biochemical Journal 263(1):1–10, 1989.

77. Schwengel D, Nouri N, Meyers D, and Levitt R C: Linkage mapping of the human thromboxane A2 receptor (TBXA2R) to chromosome 19p13.3 using transcribed 3' untranslated DNA sequence polymorphisms. Genomics 18:212–215, 1993.

78. SAGE, Statistical Analysis for Genetic Epidemiology (1992). Release 2.1. Computer program package available from the Department of Biometry and Genetics, LSU Medical Center, New Orleans, La.

79. Postma D S, Bleecker E R, Holroyd K J, Amelung P J, Panhuysen C I M, Xu J, Meyers D A, Levitt R C: Genetic Susceptibility to Asthma: Bronchial Hyperresponsiveness Coinherited with a Major Gene for Atopy. N Engl J Med 333:894–900 (1995).

80. Xu J, Levitt R C, Panhuysen C I M, Postma D S, Taylor E W, Amelung P J, Holroyd K J, Bleecker E R, Meyers D A: Evidence for two-unlinked loci regulating serum total IgE levels. Am J Hum Genet 57:425–430 (1995).

81. Meyers D A, Xu J, Holroyd K J, Panhuysen C I M, Amelung P J, Postma D S, Levitt R C, Bleecker E R. Two locus segregation and linkage analysis for total serum IgE levels. Clin Exp Allergy 25:113–11S (1995).

82. Bleecker E R, Amelung P J, Levitt R C, Postma D S, Meyers D A. Evidence for linkage of total serum IgE and bronchial hyperresponsiveness to chromosome Sq: a major regulatory locus important in asthma. Clin Exp Allergy 25:84–88 (1995).

83. Panhuysen C I M, Levitt R C, Postma D S, et al., Evidence for a susceptibility locus for asthma mapping to chromosome 5q. Journal of Investigative Medicine 43:281A (1995).

84. Levitt R C, Eleff S M, Zhang L-Y, Kleeberger S R, and Ewart S L. Linkage homology for bronchial hyperresponsiveness between DNA markers on human chromosome 5q31-q33 and mouse chromosome 13. Clin Exp Allergy 25:61–63 (1995).
85. Yang et al., U.S. Pat. No. 5,414,071 Human cytokine IL-9 (May 9, 1995).
86. Alms W and White B. Human interleukin variants generated by alternative splicing PCT/US95/04094 (WO 95/27052).
87. Cytokine handbook, Angus Thomson (1994).
88. Martinati L C, Trabetti E, Casartelli A, Boner A L, Pignatti P F. Affected sib-pair and mutation analyses of the high affinity IgE receptor beta chain locus in Italian families with atopic asthmatic children. Am J Respir Crit Care Med, 1996;153:1682–1685.
89. Kauvar, M. Lawrence, Peptide mimetic drugs: A comment on progress and prospects, Nature Biotechnology Volume 14, June 1996.

Other embodiments of the invention described above and will be apparent to those skilled in the art from consideration of the specification and practice of the invention disclosed within. It is intended that the specification and examples considered as exemplary only, with true scope and spirit of the invention being indicated by the following claims.

What is claimed is:

1. A method of treating a patient suffering from asthmatic symptoms comprising administering an amount of an antibody specific for human interleukin-9 effective to reduce the asthmatic symptoms.

2. A method of claim 1 wherein the antibody neutralizes interleukin-9 in the patient.

3. A method of claim 1 wherein the antibody down-regulates the activity of interleukin-9 in the patient.

4. A method of claim 1 wherein the antibody reduces bronchial hyperresponsiveness in the patient.

5. A method of claim 1 wherein the antibody reduces eosinophilia in the lungs of the patient.

6. A method according to claim 1 wherein the antibody is administered by one or more of the routes selected from the group consisting of intravenous, intraperitoneal, inhalation, intramuscular, subcutaneous and oral.

7. A method of any one of claims 1–6 wherein the antibody is a monoclonal antibody.

8. A method of any one of claims 1–6 wherein the antibody is administered by inhalation.

9. A method of claim 7 wherein the antibody is administered by inhalation.

10. A method of treating asthma in a patient comprising administering by inhalation an effective amount of an antibody that specifically binds to human interleukin-9.

11. A method of claim 10 wherein the antibody is a monoclonal antibody.

12. An inhalation device that delivers to a patient a therapeutically effective amount of an antibody that specifically binds to human interleukin-9.

13. An inhalation device of claim 12 wherein the antibody neutralizes interleukin-9 in the patient.

14. An inhalation device of claim 12 wherein the antibody down-regulates the activity of interleukin-9 in the patient.

15. An inhalation device of claim 14 wherein the antibody reduces bronchial hyperresponsiveness in the patient.

16. An inhalation device of claim 14 wherein the antibody reduces eosinophilia in the lungs of the patient.

17. An inhalation device of any one of claims 12–16 wherein the antibody is a monoclonal antibody.

* * * * *

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

TCTCGAGCAG GGGTGTCCAA CCTTGGCG                            28

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GCAGCTGGGA TAAATAATAT TTCATCTTCA T                       31

(2) INFORMATION FOR SEQ ID NO:3:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

TCTCGAGCAG AGATGCAGCA CCACATGGGG C                       31

(2) INFORMATION FOR SEQ ID NO:4:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

GCAGCTGGTA ACAGTTATGG AGGGGAGGTT T                                31

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTGACCAGTT GTCTCTGTTT G                                           21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CTGCATCTTG TTGATGAGGA A                                           21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GACAACTGCA CCAGACCATG C                                           21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATTAGCACTG CAGTGGCACT T                                           21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTGACCAGCT GCTTGTGTCT C                                           21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTTCAGATTT TCAATAAGGT A                                         21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GATGATTGTA CCACACCGTG C                                         21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GTTGCCGCTG CAGCTACATT T                                         21

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Ser Asp Asn Ala Thr Arg Pro Ala Phe Ser Glu Arg Leu Ser Gln Met
1             5                   10               15

Thr Asn (2) INFORMATION FOR SEQ ID NO:14:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Phe Ser Arg Val Lys Lys Ser Val Glu Val Leu Lys Asn Asn Lys Ala
1             5                   10               15

```
Pro Tyr (2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Glu Gln Pro Ala Asn Gln Thr Thr Ala Gly Asn Ala Leu Thr Phe Leu
1               5                   10                  15

Lys Ser (2) INFORMATION FOR SEQ ID NO:16:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Thr Ala Gly Asn Ala Leu Thr Phe Leu Lys Ser Leu Leu Glu Ile Phe
1               5                   10                  15

Gln Lys (2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GTAAAACGAC GGCCAGT                                              17

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GTAAAACGAC GGCCAGT                                              17

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide
```

```
    (xi) SEQUENCE DESCRIPTION: SEQ ID NO:19:

Gly Gly Gln Lys Ala Gly Ala Phe Thr Cys
1               5                   10

(2) INFORMATION FOR SEQ ID NO:20:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Leu Ser Asn Ser Ile Tyr Arg Ile Asp Cys His Trp Ser Ala Pro Glu
1               5                   10                  15

Leu Gly Gln Glu Ser Arg
            20

(2) INFORMATION FOR SEQ ID NO:21:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Cys Glu Ser Tyr Glu Asp Lys Thr Glu Gly Glu Tyr Tyr Lys Ser His
1               5                   10                  15

Trp Ser Glu Trp Ser
            20

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Thr Cys Leu Thr Asn Asn Ile
1               5

(2) INFORMATION FOR SEQ ID NO:23:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Cys Phe Ser Glu Arg Leu Ser Gln Met Thr Asn Thr Thr Met Gln Thr
1               5                   10                  15

Arg Tyr (2) INFORMATION FOR SEQ ID NO:24:
```

(i) SEQUENCE CHARACTERISTICS:
     (A) LENGTH: 415 base pairs
     (B) TYPE: nucleic acid
     (C) STRANDEDNESS: single
     (D) TOPOLOGY: linear (ii) MOLECULE TYPE: DNA (genomic)

(xi) SEQUENCE DESCRIPTION: SEQ ID NO:24:

```
TCTCGAGCAG GGGTGTCCAA CCTTGGCGGG GATCCTGGAC ATCAACTTCC TCATCAACAA      60
GATGCAGGAA GATCCAGCTT CCAAGTGCCA CTGCAGTGCT AATGTGACCA GTTGTCTCTG     120
TTTGGGCATT CCCTCTGACA ACTGCACCAG ACCATGCTTC AGTGAGAGAC TGTCTCAGAT     180
GACCAATACC ACCATGCAAA CAAGATACCC ACTGATTTTC AGTCGGGTGA AAAAATCAGT     240
TGAAGTACTA AAGAACAACA AGTGTCCATA TTTTTCCTGT GAACAGCCAT GCAACCAAAC     300
CACGGCAGGC AACGCGCTGA CATTTCTGAA GAGTCTTCTG GAAATTTTCC AGAAAGAAAA     360
GATGAGAGGG ATGAGAGGCA AGATATGAAG ATGAAATATT ATTTATCCCA GCTGC          415
```

(2) INFORMATION FOR SEQ ID NO:25:

(i) SEQUENCE CHARACTERISTICS:
       (A) LENGTH: 127 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:25:

```
Gln Gly Cys Pro Thr Leu Ala Gly Ile Leu Asp Ile Asn Phe Leu Ile
1               5                   10                  15

Asn Lys Met Gln Glu Asp Pro Ala Ser Lys Cys His Cys Ser Ala Asn
            20                  25                  30

Val Thr Ser Cys Leu Cys Leu Gly Ile Pro Ser Asp Asn Cys Thr Arg
        35                  40                  45

Pro Cys Phe Ser Glu Arg Leu Ser Gln Met Thr Asn Thr Thr Met Gln
    50                  55                  60

Thr Arg Tyr Pro Leu Ile Phe Ser Arg Val Lys Lys Ser Val Glu Val
65                  70                  75                  80

Leu Lys Asn Asn Lys Cys Pro Tyr Phe Phe Ser Cys Glu Gln Pro Cys
                85                  90                  95

Asn Gln Thr Thr Ala Gly Asn Ala Leu Thr Phe Leu Lys Ser Leu Leu
            100                 105                 110

Glu Ile Phe Gln Lys Glu Lys Met Arg Gly Met Arg Gly Lys Ile
        115                 120                 125
```

(2) INFORMATION FOR SEQ ID NO:26:

(i) SEQUENCE CHARACTERISTICS:
       (A) LENGTH: 415 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:26:

```
TCTCGAGCAG GGGTGTCCAA CCTTGGCGGG GATCCTGGAC ATCAACTTCC TCATCAACAA      60
GATGCAGGAA GATCCAGCTT CCAAGTGCCA CTGCAGTGCT AATGTGACCA GTTGTCTCTG     120
```

```
TTTGGGCATT CCCTCTGACA ACTGCACCAG ACCATGCTTC AGTGAGAGAC TGTCTCAGAT      180

GACCAATACC ACCATGCAAA CAAGATACCC ACTGATTTTC AGTCGGGTGA AAAAATCAGT      240

TGAAGTACTA AGAACAACA AGTGTCCATA TTTTTCCTGT GAACAGCCAT GCAACCAAAC       300

CATGGCAGGC AACGCGCTGA CATTTCTGAA GAGTCTTCTG GAAATTTTCC AGAAAGAAAA      360

GATGAGAGGG ATGAGAGGCA AGATATGAAG ATGAAATATT ATTTATCCCA GCTGC           415
```

(2) INFORMATION FOR SEQ ID NO:27:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Gln Gly Cys Pro Thr Leu Ala Gly Ile Leu Asp Ile Asn Phe Leu Ile
 1               5                  10                  15

Asn Lys Met Gln Glu Asp Pro Ala Ser Lys Cys His Cys Ser Ala Asn
             20                  25                  30

Val Thr Ser Cys Leu Cys Leu Gly Ile Pro Ser Asp Asn Cys Thr Arg
         35                  40                  45

Pro Cys Phe Ser Glu Arg Leu Ser Gln Met Thr Asn Thr Thr Met Gln
     50                  55                  60

Thr Arg Tyr Pro Leu Ile Phe Ser Arg Val Lys Lys Ser Val Glu Val
 65                  70                  75                  80

Leu Lys Asn Asn Lys Cys Pro Tyr Phe Ser Cys Glu Gln Pro Cys Asn
                 85                  90                  95

Gln Thr Met Ala Gly Asn Ala Leu Thr Phe Leu Lys Ser Leu Leu Glu
            100                 105                 110

Ile Phe Gln Lys Glu Lys Met Arg Gly Met Arg Gly Lys Ile
            115                 120                 125
```

(2) INFORMATION FOR SEQ ID NO:28:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
ATGAAAAAGA CAGCTATCGC GATTGCAGTG GCACTGGCTG GTTTCGCTAC CGTTGCGCAA       60

GCTGACTACA AGGACGACGA TGACAAGCTT GAATTCTCTA GAGATATCGT CGACAGATCT      120

CTCGAGCAGG GGTGTCCAAC CTTGGCGGGG ATCCTGGACA TCAACTTCCT CATCAACAAG      180

ATGCAGGAAG ATCCAGCTTC CAAGTGCCAC TGCAGTGCTA ATGTGACCAG TTGTCTCTGT      240

TTGGGCATTC CCTCTGACAA CTGCACCAGA CCATGCTTCA GTGAGAGACT GTCTCAGATG      300

ACCAATACCA CCATGCAAAC AAGATACCCA CTGATTTTCA GTCGGGTGAA AAAATCAGTT      360

GAAGTACTAA AGAACAACAA GTGTCCATAT TTTTCCTGTG AACAGCCATG CAACCAAACC      420

ACGGCAGGCA ACGCGCTGAC ATTTCTGAAG AGTCTTCTGG AAATTTTCCA GAAAGAAAAG      480

ATGAGAGGGA TGAGAGGCAA GATATGAAGA TGAAATATTA TTTATCCCAG CTGCCAACGG      540

TAGCGAAACC AGCCAGTGCC ACTGCAATCG CGATAGCTGT CTTTT                     585
```

(2) INFORMATION FOR SEQ ID NO:29:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Leu Glu Phe
            20                  25                  30

Ser Arg Asp Ile Val Asp Arg Ser Leu Glu Gln Gly Cys Pro Thr Leu
            35                  40                  45

Ala Gly Ile Leu Asp Ile Asn Phe Leu Ile Asn Lys Met Gln Glu Asp
50                  55                  60

Pro Ala Ser Lys Cys His Cys Ser Ala Asn Val Thr Ser Cys Leu Cys
65                  70                  75                  80

Leu Gly Ile Pro Ser Asp Asn Cys Thr Arg Pro Cys Phe Ser Glu Arg
                85                  90                  95

Leu Ser Gln Met Thr Asn Thr Thr Met Gln Thr Arg Tyr Pro Leu Ile
                100                 105                 110

Phe Ser Arg Val Lys Lys Ser Val Glu Val Leu Lys Asn Asn Lys Cys
                115                 120                 125

Pro Tyr Phe Ser Cys Glu Gln Pro Cys Asn Gln Thr Thr Ala Gly Asn
            130                 135                 140

Ala Leu Thr Phe Leu Lys Ser Leu Leu Glu Ile Phe Gln Lys Glu Lys
145                 150                 155                 160

Met Arg Gly Met Arg Gly Lys Ile
                165
```

(2) INFORMATION FOR SEQ ID NO:30:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
ATGAAAAAGA CAGCTATCGC GATTGCAGTG GCACTGGCTG GTTTCGCTAC CGTTGCGCAA      60
GCTGACTACA AGGACGACGA TGACAAGCTT GAATTCTCTA GAGATATCGT CGACAGATCT     120
CTCGAGCAGG GGTGTCCAAC CTTGGCGGGG ATCCTGGACA TCAACTTCCT CATCAACAAG     180
ATGCAGGAAG ATCCAGCTTC CAAGTGCCAC TGCAGTGCTA ATGTGACCAG TTGTCTCTGT     240
TTGGGCATTC CCTCTGACAA CTGCACCAGA CCATGCTTCA GTGAGAGACT GTCTCAGATG     300
ACCAATACCA CCATGCAAAC AAGATACCCA CTGATTTTCA GTCGGGTGAA AAAATCAGTT     360
GAAGTACTAA AGAACAACAA GTGTCCATAT TTTTCCTGTG AACAGCCATG CAACCAAACC     420
ATGGCAGGCA ACGCGCTGAC ATTTCTGAAG AGTCTTCTGG AAATTTTCCA GAAAGAAAAG     480
ATGAGAGGGA TGAGAGGCAA GATATGAAGA TGAAATATTA TTTATCCCAG CTGCCAACGG     540
TAGCGAAACC AGCCAGTGCC ACTGCAATCG CGATAGCTGT CTTTT                     585
```

(2) INFORMATION FOR SEQ ID NO:31:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE:

(xi) SEQUENCE DESCRIPTION: SEQ ID NO:31:

```
Met Lys Lys Thr Ala Ile Ala Ile Ala Val Ala Leu Ala Gly Phe Ala
1               5                  10                  15

Thr Val Ala Gln Ala Asp Tyr Lys Asp Asp Asp Lys Leu Glu Phe
            20                  25                  30

Ser Arg Asp Ile Val Asp Arg Ser Leu Glu Gln Gly Cys Pro Thr Leu
            35                  40                  45

Ala Gly Ile Leu Asp Ile Asn Phe Leu Ile Asn Lys Met Gln Glu Asp
50                  55                  60

Pro Ala Ser Lys Cys His Cys Ser Ala Asn Val Thr Ser Cys Leu Cys
65                  70                  75                  80

Leu Gly Ile Pro Ser Asp Asn Cys Thr Arg Pro Cys Phe Ser Glu Arg
                85                  90                  95

Leu Ser Gln Met Thr Asn Thr Thr Met Gln Thr Arg Tyr Pro Leu Ile
                100                 105                 110

Phe Ser Arg Val Lys Lys Ser Val Glu Val Leu Lys Asn Asn Lys Cys
            115                 120                 125

Pro Tyr Phe Ser Cys Glu Gln Pro Cys Asn Gln Thr Met Ala Gly Asn
130                 135                 140

Ala Leu Thr Phe Leu Lys Ser Leu Leu Glu Ile Phe Gln Lys Glu Lys
145                 150                 155                 160

Met Arg Gly Met Arg Gly Lys Ile
                165
```

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GCTCCAGTCC GCTGTCAA                                        18

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

CTCCCCCTGC AGCCTACC                                        18

(2) INFORMATION FOR SEQ ID NO:34:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:34:

CGGGGCTGAC TAAAGGTTCT                                           20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GTTCTTAAAG AGCATTCACT                                           20

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

ATTTTCACAT CTGGAATCTT CACT                                      24

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

AATCCAAGGT CAACATTATG                                           20

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

TTTCTTTGAA TAAATCCTTA C                                         21

(2) INFORMATION FOR SEQ ID NO:39:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:39:

GAAATCACCA ACAGGAACAT A                                            21

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

ATCAACTTTC ATCCCCACAG T                                            21

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

GGATAAATAA TATTTCATCT TCAT                                         24
```